(12) United States Patent
Allawi et al.

(10) Patent No.: US 8,354,232 B2
(45) Date of Patent: Jan. 15, 2013

(54) T-STRUCTURE INVASIVE CLEAVAGE ASSAYS, CONSISTENT NUCLEIC ACID DISPENSING, AND LOW LEVEL TARGET NUCLEIC ACID DETECTION

(75) Inventors: Hatim Taysir Allawi, Madison, WI (US); Vecheslav A. Elagin, Waunakee, WI (US); Victor I. Lyamichev, Madison, WI (US); Kwok Wu, San Diego, CA (US); Walter Iszczyszyn, Verona, WI (US); Chris Fleming, Lodi, WI (US); LuAnne Chehak, Janesville, WI (US); Scott M. Law, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 217 days.

(21) Appl. No.: 12/840,015

(22) Filed: Jul. 20, 2010

(65) Prior Publication Data
US 2010/0285488 A1 Nov. 11, 2010

Related U.S. Application Data

(63) Continuation of application No. 11/811,544, filed on Jun. 11, 2007, now Pat. No. 7,759,062.

(60) Provisional application No. 60/812,465, filed on Jun. 9, 2006.

(51) Int. Cl.
*C12Q 1/68* (2006.01)
*C12P 19/34* (2006.01)

(52) U.S. Cl. ...................................... 435/6.12; 435/91.2
(58) Field of Classification Search ........................ None
See application file for complete search history.

(56) References Cited

U.S. PATENT DOCUMENTS

| | | |
|---|---|---|
| 5,001,050 A | 3/1991 | Blanco |
| 5,198,543 A | 3/1993 | Blanco |
| 5,210,015 A | 5/1993 | Gelfand |
| 5,424,186 A | 6/1995 | Fodor |
| 5,424,413 A | 6/1995 | Hogan |
| 5,451,503 A | 9/1995 | Hogan |
| 5,472,881 A | 12/1995 | Beebe |
| 5,474,796 A | 12/1995 | Brennan |
| 5,487,972 A | 1/1996 | Gelfand |
| 5,514,543 A | 5/1996 | Grossman |
| 5,521,065 A | 5/1996 | Whiteley |
| 5,538,848 A | 7/1996 | Livak |
| 5,587,128 A | 12/1996 | Wilding |
| 5,614,402 A | 3/1997 | Dahlberg |
| 5,744,305 A | 4/1998 | Fodor |
| 5,795,763 A | 8/1998 | Dahlberg |
| 5,843,669 A | 12/1998 | Kaiser |
| 5,846,717 A | 12/1998 | Brow |
| 5,858,659 A | 1/1999 | Sapolsky |
| 5,912,148 A | 6/1999 | Eggerding |
| 5,919,626 A | 7/1999 | Shi |
| 5,925,525 A | 7/1999 | Fodor |
| 5,952,174 A | 9/1999 | Nikiforov |
| 5,985,551 A | 11/1999 | Brennan |
| 5,985,557 A | 11/1999 | Prudent |
| 5,994,069 A | 11/1999 | Hall |
| 6,001,311 A | 12/1999 | Brennan |
| 6,001,567 A | 12/1999 | Brow |
| 6,001,983 A | 12/1999 | Benner |
| 6,017,696 A | 1/2000 | Heller |
| 6,045,996 A | 4/2000 | Cronin |
| 6,051,380 A | 4/2000 | Sosnowski |
| 6,063,339 A | 5/2000 | Tisone |
| 6,068,818 A | 5/2000 | Ackley |
| 6,090,543 A | 7/2000 | Prudent |
| 6,117,634 A | 9/2000 | Langmore |
| 6,126,899 A | 10/2000 | Woudenberg |
| 6,130,073 A | 10/2000 | Eggerding |
| 6,183,960 B1 | 2/2001 | Lizardi |
| 6,194,149 B1 | 2/2001 | Neri |
| 6,197,557 B1 | 3/2001 | Makarov |
| 6,210,884 B1 | 4/2001 | Lizardi |
| 6,235,502 B1 | 5/2001 | Weissman |
| 6,258,103 B1 | 7/2001 | Saracione |
| 6,319,469 B1 | 11/2001 | Mian |
| 6,323,009 B1 | 11/2001 | Lasken |
| 6,344,316 B1 | 2/2002 | Lockhart |
| 6,375,903 B1 | 4/2002 | Cerrina |
| 6,399,397 B1 | 6/2002 | Zarling |
| 6,410,229 B1 | 6/2002 | Lockhart |

(Continued)

FOREIGN PATENT DOCUMENTS
EP 332435 9/1989
(Continued)

OTHER PUBLICATIONS

Shalon "A DNA microarray system for analyzing complex DNA samples using two-color fluorescent probe hybridization" Genome Methods, 6:639-45 (1996).
Shchepinov, et al. "Steric factors influencing hybridisation of nucleic acids to oligonucleotide arrays" Nucleic Acids Research 25: 1155-61 (1997).
Stryer, et al. "Fluorescence energy transfer as a spectroscopic ruler" 1978, Ann. Rev. Biochem., 47:819-46.
Suter, et al. "The immunochemistry of sandwich ELISAs. II. A novel system prevents the denaturation of capture antibodies" Immunol. Lett. 13:313-6 (1986).
Tyagi, et al. "Molecular beacons: probes that fluoresce upon hybridization" 1996 Nature Biotech, 14, 303-8.
Tyagi, et al. "Wavelength-shifting molecular beacons" Nature Biotechnology 18:1191-6 (2000).

(Continued)

*Primary Examiner* — Gary Benzion
*Assistant Examiner* — David Thomas
(74) *Attorney, Agent, or Firm* — Casimir Jones, S.C.

(57) ABSTRACT

The present invention relates to systems, methods and kits for low-level detection of nucleic acids, detecting at least two different viral sequences in a single reaction vessel, and increasing the dynamic range of detection of a viral target nucleic acid in a sample. The present invention also relates to T-structure invasive cleavage assays, as well as T-structure related target dependent non-target amplification methods and compositions. The present invention further relates to methods, compositions, devices and systems for consistent nucleic acid dispensing onto surfaces.

11 Claims, 15 Drawing Sheets

U.S. PATENT DOCUMENTS

| | | | |
|---|---|---|---|
| 6,528,254 | B1 | 3/2003 | Sorge |
| 6,613,787 | B2 | 9/2003 | Wilson |
| 6,627,159 | B1 | 9/2003 | Bedingham |
| 6,660,517 | B1 | 12/2003 | Wilding |
| 6,709,869 | B2 | 3/2004 | Mian |
| 6,720,187 | B2 | 4/2004 | Bedingham |
| 6,734,401 | B2 | 5/2004 | Bedingham |
| 6,780,982 | B2 | 8/2004 | Lyamichev |
| 6,814,935 | B2 | 11/2004 | Harms |
| 6,913,881 | B1 | 7/2005 | Aizenstein |
| 6,932,110 | B2 | 8/2005 | Mijers |
| 6,977,161 | B2 | 12/2005 | Grenier |
| 7,026,168 | B2 | 4/2006 | Bedingham |
| 7,211,443 | B2 | 5/2007 | Woudenberg |
| 7,303,869 | B2 | 12/2007 | Stevens |
| 7,432,048 | B2 | 10/2008 | Neri |
| 2003/0228703 | A1 | 12/2003 | Hoppe |
| 2004/0014067 | A1 | 1/2004 | Lyamichev |
| 2004/0018489 | A1 | 1/2004 | Ma |
| 2004/0203035 | A1 | 10/2004 | Mast |
| 2005/0014163 | A1 | 1/2005 | Dong |
| 2005/0074788 | A1 | 4/2005 | Dahlberg |
| 2005/0186588 | A1 | 8/2005 | Lyamichev |
| 2005/0191660 | A1 | 9/2005 | Vinayak |
| 2006/0147955 | A1 | 7/2006 | Allawi |

FOREIGN PATENT DOCUMENTS

| | | |
|---|---|---|
| WO | WO95/11995 | 5/1995 |
| WO | WO95/13399 | 5/1995 |
| WO | WO97/27214 | 7/1997 |
| WO | WO98/23774 | 6/1998 |
| WO | WO98/39485 | 9/1998 |
| WO | WO98/42873 | 10/1998 |
| WO | WO98/50403 | 11/1998 |
| WO | WO99/42804 | 8/1999 |
| WO | WO99/42813 | 8/1999 |
| WO | WO99/67641 | 12/1999 |
| WO | WO00/01798 | 1/2000 |
| WO | WO00/39587 | 7/2000 |
| WO | WO00/49959 | 8/2000 |
| WO | WO01/57254 | 8/2001 |
| WO | WO01/88190 | 11/2001 |
| WO | WO01/90337 | 11/2001 |
| WO | WO01/98537 | 12/2001 |
| WO | WO02/00934 | 1/2002 |
| WO | WO02/04597 | 1/2002 |
| WO | WO02/070755 | 9/2002 |
| WO | WO2004/065550 | 8/2004 |

OTHER PUBLICATIONS

Van De Rijke, et al. "Up-converting phosphor reporters for nucleic acid microarrays" Nature Biotechnol. 19(3):273-6 (2001).

Vinogradov, et al. "Block Polycationic Oligonucleotide Derivative: Synthesis and Inhibition of Herpes Virus Reproduction" Bioconjugate Chem. 7:3-6 (1996).

Walsh, et al. "Preferential PCR amplification of alleles: mechanisms and solutions" PCR Methods and Applications, 1: 241-50 (1992).

Wu, et al. "The Ligation Amplification Reaction (LAR)—Amplification of Specific DNA Sequences Using Sequential Rounds of Template-Dependent Ligation" Genomics 4:560-9 (1989).

Young, et al. (1985) "Quantitative Analysis of Solution Hybridisation" Nucleic Acid Hybridisation: A Practical Approach (Hames & Higgins, Eds.) pp. 47-71, IRL Press, Oxford.

Zarlenga, et al. "PCR as a diagnostic and quantitative technique in veterinary parasitology" Vet Parasitol. 101: 215-30 (2001).

Zuker "On finding all suboptimal foldings of an RNA molecule" Science, 244: 48-52 (1989).

Agrawal, et al. "Oligodeoxynucleoside phosphoramidates and phosphorothioates as inhibitors of human immunodeficiency virus" Proc. Natl. Acad. Sci USA , 85:7079-83 (1988).

Agrawal, et al. "Site specific functionalization of oligonucleotides for attaching two different reporter groups" Nucl. Acid Res. 18:5419-23 (1990).

Allawi, et al. "Thermodynamics and NMR of internal G.T mismatches in DNA" Biochemistry, 36:10581-94 (1997).

Bauer, et al. "Paternity testing after pregnancy termination using laser microdissection of chorionic villi" Int. J. Legal Med. 116: 39-42 (2002).

Bilkova, et al. "Oriented immobilization of chymotrypsin by use of suitable antibodies coupled to a nonporous solid support" J. Chromatogr. A, 852:141-9 (1999).

Boger "Design, Synthesis, and evaluation of DNA minor groove binding agents: the duocarmycins" Pure & Appl. Chem., vol. 66, No. 4, pp. 837-844.

Cargill, et al. "Characterization of single-nucleotide polymorphisms in coding regions of human genes" Nature Genetics, 22: 231-8 (1999).

Chamberlain, et al. "Deletion screening of the Duchenne muscular dystrophy locus via multiplex DNA amplification" Nucleic Acids Res., 16:11141-56 (1988).

Chamberlin, et al. "New RNA polymerase from *Escherichia coli* infected with bacteriophage T7" Nature 228:227-31 (1970).

Chernukhin, et al. "A method of immobilization on the solid support of complex and simple enzymes retaining their activity" Anal. Biochem., vol. 280, pp. 178-181 (2000).

Corstjens, et al. "Infrared up-converting phosphors for bioassays" IEE Proc. Nanobiotechnol. 152(2):64-72 (2005).

Elnifro, et al. "Multiplex PCR: optimization and application in diagnostic virology" Clinical Microbiology Reviews, 13: 559-70 (2000).

Frey, et al. "Covalent Attachment and Derivatization of Poly(L-lysine) Monolayers on Gold Surfaces As Characterized by Polarization—Modulation FT-IR Spectroscopy" Analytical Chem, 68:3187-93 (1996).

Froehler "Deoxynucleoside H-Phosphonate Diester Intermediates in the Synthesis of Internucleotide Phosphate Analogues" Tetrahedron Lett. 27:5575-8 (1986).

Froehler, et al. "Phosphoramidate analogues of DNA: synthesis and thermal stability of heteroduplexes" Nucl. Acids Res. 16:4831-9 (1988).

Frutos, et al. "Demonstration of a word design strategy for DNA computing on surfaces" Nucl. Acid. Res., 25:4748-57 (1997).

Gibbs et al. "Detection of single DNA base differences by competitive oligonucleotide priming" 1989 Nucleic Acids Research 17, 2347-8.

Guo, et al. "Direct fluorescence analysis of genetic polymorphisms by hybridization with oligonucleotide arrays on glass supports" Nucleic Acids Res., 22:5456-65 (1994).

Hagmann "Human genome. A good SNP may be hard to find" Science, 285: 21-2 (1999).

Hall, et al. "Sensitive detection of DNA polymorphisms by the serial invasive signal amplification reaction" PNAS, USA, 97:8272-7 (2000).

Halushka, et al. "Patterns of single-nucleotide polymorphisms in candidate genes for blood-pressure homeostasis" Nature Genetics, 22: 239-47 (1999).

Hidding, et al. "Haplotype frequencies and population data of nine Y-chromosomal STR polymorphisms in a German and a Chinese population" Forensic Sci. Int., 113: 47-53 (2000).

Jordan, et al. "Surface Plasmon Resonance Imaging Measurements of DNA Hybridization Adsorption and Streptavidin/DNA Multilayer Formation at Chemically Modified Gold Surfaces" Analytical Chem, 69, 4939-47 (1997).

Kacian, et al. "A replicating RNA molecule suitable for a detailed analysis of extracellular evolution and replication" Proc. Natl. Acad. Sci. USA 69:3038-42 (1972).

Kong, et al. "Synthesis and duplex stability of oligonucleotides containing cytosine-thymine analogues" Nucleic Acids Res., 1989, 17, 10373-10383.

Kong, et al. "Synthesis of oligodeoxyribonucleotides containing degenerate bases and their use as primers in the polymerase chain reaction" Nucleic Acids Res., 1992, 20, 5149-5152.

Kwok "Approaches to allele frequency determination" Pharmacogenomics, 1: 231-5 (2000).

Kwok "Single nucleotide polymorphism libraries: why and how are we building them?" Molecular Medicine Today, 5: 538-543 (1999).

Letsinger, et al. "Cationic Oligonucleotides" J. Am. Chem. Soc., 110:4470-1 (1988).

Li, et al. "Site-Specific Photomodification of DNA by Porphyrin-Oligonucleotide Conjugates Synthesized via a Solid Phase H-Phosphonate Approach" Bioconjugate Chem. 8:49-56 (1997).

Lindblad-Toh, et al. "Large-scale discovery and genotyping of single-nucleotide polymorphisms in the mouse" Nature Genet. 4: 381-6 (2000).

Lyamichev, et al. "Polymorphism identification and quantitative detection of genomic DNA by invasive cleavage of oligonucleotide probes" Nat. Biotech., 17:292-6 (1999).

Maskos, et al. "Oligonucleotide hybridizations on glass supports: a novel linker for oligonucleotide synthesis and hybridization properties of oligonucleotides synthesised in situ" Nucleic Acids Res., 20:1679-84 (1992).

Mathews, et al. "Predicting oligonucleotide affinity to nucleic acid targets" RNA 5:1458-69 (1999).

Mhlanga, et al. "Using molecular beacons to detect single-nucleotide polymorphisms with real-time PCR" 2001 Methods 25, 463-471.

Nuzzo, et al. "Adsorption of Bifunctional Organic Disulfides on Gold Surfaces" JACS, 105:4481-3 (1983).

O'Donnelly-Maloney, et al. Genetic Analysis: Biomolecular Engineering, 13:151 (1996).

Olivier "The Invader assay for SNP genotyping" 2005 Mutant Res 573, 103-110.

Orpana "Fluorescence resonance energy transfer (FRET) using ssDNA binding fluorescent dye" 2004 Biomol Eng 21, 45-50.

Ostermayer "Preparation and properties of infrared-to-visible conversion phosphors" Metall. Trans. 752, 747-755 (1971).

Polz, et al. "Bias in template-to-product ratios in multitemplate PCR" Applied and Environmental Microbiology, 64: 3724-30 (1998).

Reynaldo, et al. "The kinetics of oligonucleotide replacements" J. Mol. Biol. 97: 511-520 (2000).

Risch, et al. "The future of genetic studies of complex human diseases" Science, 273: 1516-7 (1996).

Rudi, et al., "Development and application of new nucleic acid-based technologies for microbial community analyses in foods" Int J Food Microbiology, 78: 171-80 (2002).

Rychlik, et al. "A computer program for choosing optimal oligonucleotides for filter hybridization, sequencing and in vitro amplification of DNA" Nucleic Acids Res, 17: 8543-51 (1989).

Santalucia "A unified view of polymer, dumbbell, and oligonucleotide DNA nearest-neighbor thermodynamics" Proc Natl Acad Sci U S A, 95:1460-5 (1998).

Schutz, et al. "Synthesis of Oligonucleotides Labelled with a Novel Type of Chemically Stable Acridine Dye" Tetrachedron Lett. 36:8407-10 (1995).

Schweitzer, et al. "Aromatic Nonpolar Nucleosides as Hydrophobic Isosteres of Pyrimidine and Purine Nucleosides" J. Org. Chem., 1994, 59, 7238-7242.

Schweitzer, et al. "Hydrophobic, Non-Hydrogen-Bonding Bases and Base Pairs in DNA" J. Am. Chem. Soc., 1995, 117, 1863-1872.

Selvin "Fluorescence resonance energy transfer" 1995, Methods Enzymol., 246:300-34.

FIGURE 1

| DATA | | | | | | | | | | | | | |
|---|---|---|---|---|---|---|---|---|---|---|---|---|---|
| | | 1st target | Raw Data | | | | | | 1st target | Analysis | | | |
| Fam | IC c/r | | | 1 | 2 | 3 | 4 | Fam | IC c/r | | | Ave | %CV | FOZ |
| | 150 | 500.00 | A | 11,388 | 11,670 | 11,397 | 10,925 | | 150 | 500.00 | A | 11,345 | 3% | 19.85 |
| | 150 | 166.67 | B | 10,647 | 10,998 | 10,165 | 10,622 | | 150 | 166.67 | B | 10,608 | 3% | 18.56 |
| | 150 | 55.56 | C | 10,268 | 10,406 | 10,365 | 10,281 | | 150 | 55.56 | C | 10,330 | 1% | 18.08 |
| | 150 | 18.52 | D | 7,274 | 10,233 | 10,342 | 9,976 | | 150 | 18.52 | D | 9,456 | 15% | 16.55 |
| | 150 | 6.17 | E | 2,631 | 10,178 | 1,145 | 7,920 | | 150 | 6.17 | E | 5,469 | 78% | 9.57 |
| | 150 | 2.06 | F | 6,701 | 2,471 | 2,220 | 6,626 | | 150 | 2.06 | F | 4,505 | 55% | 7.88 |
| | 0 | 0 | G | 539 | 579 | 577 | 591 | | 0 | 0 | G | 572 | 4% | - |
| | 0 | 0 | H | 520 | 582 | 583 | 600 | | 0 | 0 | H | 571 | 6% | - |
| | | 2nd target | Raw Data | | | | | | 2nd target | Analysis | | | |
| Yellow | IC c/r | | | 1 | 2 | 3 | 4 | Yellow | IC c/r | | | Ave | %CV | FOZ |
| | 150 | 500.00 | A | 3,530 | 3,634 | 3,585 | 3,395 | | 150 | 500.00 | A | 3,536 | 3% | 5.398 |
| | 150 | 166.67 | B | 3,356 | 3,495 | 3,034 | 3,343 | | 150 | 166.67 | B | 3,307 | 6% | 5.049 |
| | 150 | 55.56 | C | 3,294 | 3,429 | 3,441 | 3,324 | | 150 | 55.56 | C | 3,372 | 2% | 5.148 |
| | 150 | 18.52 | D | 3,271 | 3,412 | 3,350 | 3,252 | | 150 | 18.52 | D | 3,321 | 2% | 5.071 |
| | 150 | 6.17 | E | 3,116 | 3,342 | 3,334 | 3,230 | | 150 | 6.17 | E | 3,256 | 3% | 4.970 |
| | 150 | 2.06 | F | 2,885 | 3,082 | 3,197 | 3,138 | | 150 | 2.06 | F | 3,076 | 4% | 4.695 |
| | 0 | 0 | G | 645 | 659 | 662 | 661 | | 0 | 0 | G | 657 | 1% | - |
| | 0 | 0 | H | 592 | 660 | 665 | 697 | | 0 | 0 | H | 654 | 7% | - |

```
                        SEQUENCE LISTING

<160> NUMBER OF SEQ ID NOS: 13

<210> SEQ ID NO 1
<211> LENGTH: 10
<212> TYPE: DNA
<213> ORGANISM: Artificial sequence
<220> FEATURE:
<223> OTHER INFORMATION: Arm sequence

<400> SEQUENCE: 1
cgcgccgagg                                                          10

<210> SEQ ID NO 2
<211> LENGTH: 14
<212> TYPE: DNA
<213> ORGANISM: Artificial sequence
<220> FEATURE:
<223> OTHER INFORMATION: Arm sequence

<400> SEQUENCE: 2
atgacgtggc agac                                                     14

<210> SEQ ID NO 3
<211> LENGTH: 12
<212> TYPE: DNA
<213> ORGANISM: Artificial sequence
<220> FEATURE:
<223> OTHER INFORMATION: Arm sequence

<400> SEQUENCE: 3
acggacgcgg ag                                                       12

<210> SEQ ID NO 4
<211> LENGTH: 11
<212> TYPE: DNA
<213> ORGANISM: Artificial sequence
<220> FEATURE:
<223> OTHER INFORMATION: Arm sequence

<400> SEQUENCE: 4
tccgcgcgtc c                                                        11

<210> SEQ ID NO 5
<211> LENGTH: 88
<212> TYPE: DNA
<213> ORGANISM: Artificial Sequence
<220> FEATURE:
<223> OTHER INFORMATION: synthetic

<400> SEQUENCE: 5
cccugcaacg cgagugcuga ggcuggugua cgacccaucg cucgcccgcu accgcgacgu   60
ccugccgcac ucuagguacg ugguccac                                      88
```

```
<210> SEQ ID NO 6
<211> LENGTH: 45
<212> TYPE: DNA
<213> ORGANISM: Artificial sequence
<220> FEATURE:
<223> OTHER INFORMATION: stem oligonucleotide

<400> SEQUENCE: 6
gtgtcggacg agcagtgaat caccggttaa ccggttaacc ggtta          45

<210> SEQ ID NO 7
<211> LENGTH: 74
<212> TYPE: DNA
<213> ORGANISM: Artificial sequence
<220> FEATURE:
<223> OTHER INFORMATION: Hypothetical Target Sequence

<400> SEQUENCE: 7
aaccggttaa ccggttaacc ggttaaccgg taaaaggggt tttccccaaa aggggttttc          60
cccaaaaggg gttt                                                           74

<210> SEQ ID NO 8
<211> LENGTH: 44
<212> TYPE: DNA
<213> ORGANISM: Artificial sequence
<220> FEATURE:
<223> OTHER INFORMATION: Upstream oligonucleotide
<220> FEATURE:
<221> NAME/KEY: misc_feature
<222> LOCATION: (44)..(44)
<223> OTHER INFORMATION: n is a, c, g, or t

<400> SEQUENCE: 8
tttggggaaa acccctttg gggaaaaccc cttttgattc actn          44

<210> SEQ ID NO 9
<211> LENGTH: 23
<212> TYPE: DNA
<213> ORGANISM: Artificial sequence
<220> FEATURE:
<223> OTHER INFORMATION: downstream probe

<400> SEQUENCE: 9
cgcgccgagg gctcgtccga cac          23

<210> SEQ ID NO 10
<211> LENGTH: 11
<212> TYPE: DNA
<213> ORGANISM: Artificial sequence
<220> FEATURE:
<223> OTHER INFORMATION: Cleaved Portion

<400> SEQUENCE: 10
cgcgccgagg g          11

<210> SEQ ID NO 11
<211> LENGTH: 12
<212> TYPE: DNA
<213> ORGANISM: Artificial sequence
<220> FEATURE:
<223> OTHER INFORMATION: Remainder of Downstream Probe

<400> SEQUENCE: 11
ctcgtccgac ac          12

<210> SEQ ID NO 12
<211> LENGTH: 55
```

-continued

```
<212> TYPE: DNA
<213> ORGANISM: Artificial sequence
<220> FEATURE:
<223> OTHER INFORMATION: stem oligonucleotide

<400> SEQUENCE: 12
tgtatcgacc gtgtcggacg agcagtgaat caccggttaa ccggttaacc ggtta      55

<210> SEQ ID NO 13
<211> LENGTH: 66
<212> TYPE: DNA
<213> ORGANISM: Artificial sequence
<220> FEATURE:
<223> OTHER INFORMATION: extended upstream oligonucleotide

<400> SEQUENCE: 13
tttggggaaa acccctttg gggaaaaccc cttttgattc actgctcgtc cgacacggtc    60
gataca                                                              66
```

T-STRUCTURE INVASIVE CLEAVAGE ASSAYS, CONSISTENT NUCLEIC ACID DISPENSING, AND LOW LEVEL TARGET NUCLEIC ACID DETECTION

The present application is a continuation of pending U.S. patent application Ser. No. 11/811,544, filed Jun. 11, 2007, which will issue on Jul. 20, 2010 as U.S. Pat. No. 7,759,062, which claims priority to expired U.S. Provisional Application Ser. No. 60/812,465, filed Jun. 9, 2006, all of which is herein incorporated by reference.

FIELD OF THE INVENTION

The present invention relates to systems, methods and kits for low-level detection of nucleic acids, detecting at least two different viral sequences in a single reaction vessel, and increasing the dynamic range of detection of a viral target nucleic acid in a sample. The present invention also relates to T-structure invasive cleavage assays, as well as T-structure related target dependent non-target amplification methods and compositions. The present invention further relates to methods, compositions, devices and systems for consistent nucleic acid dispensing onto surfaces.

BACKGROUND

All nucleic acid detection systems that rely on amplification of either the target being detected or the signal being generated inherently possess a dynamic range that limits their usefulness. At low concentrations of the target being detected, the signal generated is too low to detect or to low to be scored above background levels, and therefore is below the limit of detection, i.e., outside the dynamic range of the detection system. By contrast, at very high levels of the target being generated, the components of the detection system are exhausted such that the signal is said to be saturated, i.e. addition of still more target results in no increase in signal. In these cases, the quantity of target is said to be above the limit of detection, i.e. outside the dynamic range of the detection system.

In the real-world case of detection systems being used to detect targets from biological specimens, the range of target present in the sample being detected can be quite large, and is often either below or above the limit of detection of the system in use. Therefore, previous attempts to cover larger ranges of target concentration have required the generation of more than one detection system, to be used separately, that are optimized for a given dynamic range. Because the quantity of target nucleic acid in the specimen is by definition an unknown quantity, this very frequently requires the use of multiple detection systems sequentially to finally use the appropriate detection system that possesses the appropriate dynamic range for the specimen under examination.

As such, a single detection system with a broader dynamic range, if it was available, would significantly reduce costs, decrease labor time, and decrease expenditure of the specimen being examined. Even more, a method of increasing the dynamic range of an existing detection system would greatly aid the field of detection of targets within biological specimens generally.

SUMMARY OF THE INVENTION

The present invention provides systems, methods and kits for low-level detection of nucleic acids, detecting at least two different viral sequences in a single reaction vessel, and increasing the dynamic range of detection of a viral target nucleic acid in a sample. The present invention also provides T-structure invasive cleavage assays, as well as T-structure related target dependent non-target amplification methods and compositions. The present invention further provides methods, compositions, devices and systems for consistent nucleic acid dispensing onto surfaces (e.g., through hydrophobic polymer dispensing components using non-ionic detergents.

In some embodiments, the present invention provides methods for detecting target nucleic acid in a sample, wherein the number of copies of the target nucleic acid initially present in the sample is at low copy number (e.g., between about 2 and about 2000 copies or between 2 and 100 copies), wherein the method comprises; a) incubating the sample with a plurality of first and second probes, a plurality of reporter sequences, and a cleavage agent under conditions such that: i) the first probes hybridize to first regions of the target nucleic and are cleaved by the cleavage agent thereby generating first 5' cleaved portions, and ii) the second probes hybridize to second regions of the target nucleic acid and are cleaved by the cleavage agent thereby generating second 5' cleaved portions; and b) detecting a signal from the reporter sequences generated by hybridization of the first and second 5' cleaved portions to the reporter sequences thereby detecting the presence of the target nucleic acid in the sample. In certain embodiments, the first and second regions of the target nucleic acid are amplified prior to step a). In other embodiments, the first and second regions of the target nucleic acid are amplified with at least 30 rounds of PCR prior to step a).

In particular embodiments, the present invention provides methods for detecting target nucleic acid in a sample comprising; a) treating the sample with amplification reagents such that first and second regions of the target nucleic acids are amplified with at least 30 rounds of PCR thereby generating first and second amplified regions; b) incubating the sample with a plurality of first and second probes, a plurality of reporter sequences, and a cleavage agent under conditions such that: i) the first probes hybridize to the first regions or the first amplified regions of the target nucleic and are cleaved by the cleavage agent thereby generating first 5' cleaved portions, and ii) the second probes hybridize to the second regions or second amplified regions of the target nucleic acid and are cleaved by the cleavage agent thereby generating second 5' cleaved portions; and c) detecting any signal from the reporter sequences generated by hybridization of the first and second 5' cleaved portions to the reporter sequences thereby detecting the presence or absence of the target nucleic acid in the sample.

In some embodiments, the number of copies of the target nucleic acid initially present in the sample is between about 2 and about 100 copies, and the presence of the target nucleic acid is detected in the sample. In further embodiments, the number of copies of the target nucleic acid initially present in the sample is between about 2 and about 10 copies, and the presence of the target nucleic acid is detected in the sample. In certain embodiments, the amplification reagents comprise a first primer pair for the first region of the target nucleic acid and a second primer pair for the second region of the target nucleic acid. In other embodiments, the first primer pair comprises a first forward primer and a first reverse primer, and wherein either the first forward primer or the first reverse primer is configured to also serve as an upstream probe such that it can form an invasive cleavage structure with the first probe and the first amplified region. In further embodiments, the second primer pair comprises a second forward primer and a second reverse primer, and wherein either the second forward primer or the second reverse primer is configured to also serve as an upstream probe such that it can form an invasive cleavage structure with the second probe and the second amplified region.

In particular embodiments, the target nucleic acid is viral nucleic acid. In other embodiments, the viral nucleic acid comprises at least a portion of a RNA viral genome. In further embodiments, the viral nucleic acid is from hepatitis C virus. In some embodiments, the signal is generated by cleavage of the reporter sequences. In other embodiments, the first and second probes are cleaved as part of an invasive cleavage reaction.

In some embodiments, the incubating further comprises incubating the sample with first upstream oligonucleotides configured to form invasive cleavage structures with the first probes and the first amplified regions. In certain embodiments, the incubating further comprises incubating the sample with second upstream oligonucleotides configured to form invasive cleavage structures with the second probes and the second amplified regions.

In particular embodiments, the first and second regions of the target nucleic acid are non-overlapping. In other embodiments, the reporter sequences comprise a dye and a quencher. In some embodiments, the first and second 5' cleaved portions are identical to each other.

In additional embodiments, the methods further comprise incubating the sample with a plurality control target sequences and a plurality of third probes designed to detect the presence of the control sequences. In other embodiments, the first and second 5' cleaved portions are configured to not hybridize to the first and second regions, or the first and second amplified regions, of the target nucleic acid.

In some embodiments, the present invention provides compositions, kits, and methods of quantitating viral nucleic acid targets using multiple probes that bind to a viral target nucleic acid at different strengths. In some embodiments, groups of probes are used in which each probe exhibits different binding affinities to the viral target sequence (e.g., by altering complementarity, length, concentration, additives, etc.). The use of multiple probes with different properties allows for an increase in the dynamic range of detection assays. In some embodiments, the multiple probes are used in invasive cleavage assays.

Accordingly, in some embodiments, the present invention provides a method for detecting the presence of, absence of, or amount of a viral target nucleic acid in a sample, comprising: incubating a sample suspected of containing a viral target nucleic acid with a plurality of first probe oligonucleotides and a plurality of second probe oligonucleotides, wherein each of the first and second probe oligonucleotides comprises an analyte specific region, wherein the plurality of second probe oligonucleotides are configured to occupy a probe hybridization site on the viral target nucleic acid at a different frequency than the plurality of first probe oligonucleotides; and measuring hybridization of the first and said second probe oligonucleotides over time, thereby measuring the amount of the viral target nucleic acid. In some embodiments a plurality of third, fourth, fifth, etc. probe oligonucleotides are used. These additional oligonucleotides may be configured to bind to the same analyte-specific region of a viral target nucleic acid or may bind to different analyte-specific regions of the same or different target nucleic acids (e.g., the third and fourth probes are configured to hybridize to a second analyte-specific region of the same viral target nucleic acid such that the third probe occupies the hybridization site at a different frequency than the fourth probe).

In some embodiments, the analyte specific regions of the first probe oligonucleotides are completely complementary to the viral target nucleic acid. In some embodiments, the analyte specific regions of the second probe oligonucleotides are partially complementary to the viral target nucleic acid (e.g., contain a single mismatch). In some embodiments, the second probe oligonucleotide is shorter in length than the first probe oligonucleotide (e.g., by one, two, three, or four or more nucleotides). In some embodiments, the second probe oligonucleotides are present at least a 5 fold, and preferably at least a 10 fold lower concentration than the first probe oligonucleotides. In some embodiments, the second probe oligonucleotides are present at least a 20 fold (e.g., 100 fold, 500 fold, 1000 fold, 10,000 fold, etc. lower concentration than the first probe oligonucleotide). Where three or more probes of different concentrations are used, each probe may be separated by at least 5 fold (10 fold, 20 fold, 100 fold, etc.) concentration from one another (e.g., a third probe 10000 fold more than a first probe and a second probe 100 fold more than a first probe). In some embodiments, one of the mixtures comprises an agent known to increase or decrease hybridization efficiency (e.g., a charge tag, minor groove binding agent, or an intercalating agent). In other embodiments, one of the probes comprises one or more modified bases (e.g., amino T, indole, or nitropyrrole). In some embodiments, the analyte specific region of second probe oligonucleotide is shorter than the analyte specific region of the first probe oligonucleotide (e.g., by one or more nucleotides). In other embodiments, the analyte specific region of the second probe oligonucleotide comprises increased secondary structure relative to the analyte specific region of the first probe oligonucleotide. In certain embodiments, the first probe oligonucleotides further comprise a non-analyte specific region, wherein the non-analyte specific region comprises one or more nucleotides that are not complementary to the viral target nucleic acid. In some embodiments, each of the second probe oligonucleotides further comprises a non-analyte specific region, wherein the non-analyte specific region comprises one or more nucleotides that are not complementary to the viral target nucleic acid. In some embodiments, incubating the sample with the second probe oligonucleotides comprises incubating the sample with competitor oligonucleotides, wherein the competitor oligonucleotides each comprise a region that is complementary to the non-analyte specific regions of the second probe oligonucleotides. The present invention is not limited by the nature of the competitor. The competitor may be a second viral target nucleic acid or a different region of the first oligonucleotide where, for example, hybridization of the non-analyte specific region of the second probe to the competitor does not generate a detectable event or generates a detectable event that is distinguishable from the detectable event generated by the first and/or second probes hybridizing to the analyte-specific region.

In some embodiments, incubating the sample with the second probe oligonucleotides comprises incubating the sample with competitor oligonucleotides, wherein the competitor oligonucleotides each comprise a region that is complementary to the non-analyte specific regions of the second probe oligonucleotides. In certain embodiments, one of the mixtures comprises altered reaction conditions that alter hybridization efficiency of a probe (e.g., altered pH, buffer, ionic strength or additional compositions (e.g., crowding agents)).

In some embodiments, the sample is a sample from an animal (e.g., a human) comprising blood, serum, stool, urine, or lymph known to or suspected of comprising a target nucleic acid (e.g., a virus or a bacterium). In some embodiments, the sample comprises a purified sample of nucleic acid (e.g., total DNA or RNA from a tissue, fluid or cell; genomic DNA; etc.). In some embodiments, the viral target nucleic acid is from human immunodeficiency virus (HIV) and other retroviruses, hepatitis C virus (HCV), hepatitis B virus (HBV), hepatitis A virus (HAV), human cytomegalovirus, (CMV), herpes simplex virus (HSV), Epstein bar virus (EBV), varicella zoster virus (VZV), human papilloma virus (HPV), bacteriophages (e.g., phage lambda), influenzaviruses, adenoviruses, or lentiviruses) or a bacterium (e.g., *Chlamydia* sp., *N. gonorrhea*, or group B *streptococcus*). In other embodiments, the sample is from a plant. For example, in some embodiments, the plant is infected with or suspected of being infected with a virus.

In some embodiments, the methods of incubating the sample with the first and second probe oligonucleotides occur in the same reaction vessel (e.g., the first and second probe oligonucleotides are mixed in solution in the same reaction vessel). In some embodiments, the first an second probe oligonucleotides comprise labels. In some embodiments, the first and second labels are different from each other. In some embodiments, the first and second labels are the same label. In some embodiments, measuring the hybridization of the first and second probe oligonucleotides comprises performing an invasive cleavage structure type assay (e.g., an INVADER assay). In some such embodiments, the probes are unlabeled, but comprise a flap sequence that is removed from the probe upon cleavage during the invasive cleavage assay. In some embodiments, the removed flaps are configured to hybridize to a FRET cassette to trigger a detection reaction. In some embodiments, the first and second probes report to the same FRET cassette (e.g., the first and second probe generate identical flaps upon cleavage in the primary invasive cleavage reaction). In other embodiments, determining the amount of the target nucleic acid comprises performing a detection assay including, but not limited to, a hybridization assay, any real-time amplification assay that involves hybridization, a TAQMAN assay, SNP-IT assay, a Southern blot, a ligase assay, a microarray assay, a FULLVELOCITY assay, a cycling probe assay, NASBA, branched DNA assay, TMA, methods employing molecular beacons, capillary electrophoresis detection methods, microfluidic detection methods, and the like.

In other embodiments, the present invention provides a method for detecting the presence of, absence of, or amount of a viral target nucleic acid in a sample, comprising: providing a sample containing or suspected of containing a viral target nucleic acid; a first probe oligonucleotide comprising an analyte specific region and a first label, wherein the analyte specific region of the first probe oligonucleotide is completely complementary to the viral target nucleic acid; and a second probe oligonucleotide comprising an analyte specific region and a second label, wherein the analyte specific region of the second probe oligonucleotide is partially complementary to the viral target nucleic acid; and exposing the sample to the first and second probe oligonucleotides; and, in some embodiments, determining the amount of the viral target nucleic acid in the sample.

The present invention further provides a kit comprising reagents and, in some embodiments, instructions, for performing the detection assays of the present invention. For example, in some embodiments, the present invention provide a kit for detecting the presence of, absence of, or quantitation of viral target nucleic acids in a sample, comprising: a plurality of first probe oligonucleotides comprising a first analyte specific region and, optionally, a first label, and a plurality of second probe oligonucleotides comprising a second analyte specific region and, optionally, a second label, wherein the second probe oligonucleotides are configured to occupy a probe hybridization site on the viral target nucleic acid at a different frequency than the first mixture of probe oligonucleotides; and reagents for performing an INVADER assay using the first and second probe oligonucleotides. In some embodiments, the analyte specific regions of the first probe oligonucleotides are completely complementary to the viral target nucleic acid. In other embodiments, the analyte specific regions of the second probe oligonucleotides are partially complementary to the viral target nucleic acid (e.g., contain one or more mismatches with the viral target nucleic acid). In still further embodiments, the second probe oligonucleotides are present at a lower concentration than the first probe oligonucleotides. In some embodiments, the kit further comprises instructions for using the kit for performing a nucleic acid detection assay. In some embodiments, the kit comprises reagents and/or instructions for use of the methods of the present invention with a one or more different detection assay technologies (e.g., an invasive cleavage assay (e.g., INVADER assay), a TAQMAN assay, SNP-IT assay, etc.)).

In some embodiments, the present invention provides methods for detecting a viral target nucleic acid, comprising: a) amplifying a viral target nucleic acid at two different levels of amplification to generate amplification products; b) hybridizing the amplification products to a first probe and second probe, wherein the first probe hybridizes to the amplification products at a different frequency than the second probe. In certain embodiments, the second probe is present at a 10-fold lower concentration than the first probe. In other embodiments, the at least two probes bind to the same sequence.

In additional embodiments, the present invention provides methods for detecting a viral target nucleic acid in a plurality of samples over a broad dynamic range, comprising: exposing a first sample having less than $10^3$ copies of viral target nucleic acid and a second sample having greater than $10^5$ copies of viral target nucleic acid to a set of reagents under conditions such that the viral target nucleic acid in the first and second samples is detected, wherein method comprises exposing each of the first and second samples to a first probe and a second probe, wherein the second probe hybridizes to the viral target nucleic acids at a different frequency than the first probe. In particular embodiments, the viral target nucleic acid in the first and second samples is quantitated. In further embodiments, the second probe is present at a 10-fold lower concentration than the first probe. In some embodiments, the viral target nucleic acids are treated under two or more different amplification conditions prior to detection. In other embodiments, the method is conducted without any amplification of the viral target nucleic acid.

In some embodiments, the present invention provides methods for detecting a viral target nucleic acid, comprising: a) amplifying a viral target nucleic acid to generate amplification products; b) contacting the amplification products with first and second probes, wherein the second probe hybridizes to the amplification products at a different frequency that the first probe; c) cleaving the first and second probes; and d) detecting the cleavage of the first and second probes.

In other embodiments, the present invention provides kits comprising: a polymerase, a 5' nuclease, and two probes configured to hybridize to an analyte-specific region of a viral target nucleic acid, wherein the second probe hybridizes to the analyte-specific region at a different frequency than the first probe oligonucleotide, and wherein the first and second probes are configured to both directly or indirectly generate a detectable signal in the presence of the viral target nucleic acid. In some embodiments, the first and second probes generate the same type of detectable signal. In certain embodiments, the first and second probes each comprise a flap sequence that is complementary to a FRET cassette. In other embodiments, the flap of the first probe is identical to the flap of the second probe.

In some embodiments, the present invention provides methods for detecting a viral target nucleic acid in a sample comprising; a) contacting a sample suspected of containing a viral target nucleic acid with amplification reagents such that, if the viral target nucleic acid is present: i) a first region of the viral target nucleic acid is either not amplified, or is amplified at a first level to generate plurality of first product sequences; and ii) a second region of the viral target nucleic acid is amplified at a second level to generate a plurality of second product sequences, wherein the second level of amplification is greater than the first level of amplification (e.g. such that the second product sequences are present at a level of at least 10-fold . . . 100-fold . . . 1000-fold . . . 10,000-fold . . . or 100,000-fold higher concentration after amplification that the target nucleic acid, or first product sequences if produced); and b) incubating the sample with a plurality of first and second probe oligonucleotides, wherein: i) the first and second probe oligonucleotides hybridize to the first region of the target nucleic acid, and the first product sequences is produced, at different frequencies, or ii) the first and second probe oligonucleotides hybridize to the second product sequences at a different frequency; and c) measuring hybridization of the first and second probe oligonucleotides thereby detecting the target nucleic acid in the sample. In particular embodiments, the second product sequences are present at a level between 100-fold and 100,000 fold higher concentration after amplification than the target nucleic acid, or first product sequences if produced.

In certain embodiments, the present invention provides methods for detecting a viral target nucleic acid in a plurality of samples over a broad dynamic range, comprising: exposing a first sample having less than $10^3$ copies of viral target nucleic acid and a second sample having greater than $10^5$ copies of viral target nucleic acid to a set of reagents under conditions such that the viral target nucleic acid in the first and second samples is detected, wherein the method comprises exposing each of the first and second samples to a first probe and a second probe, wherein the second probe hybridize to the viral target at different frequencies.

In particular embodiments, the present invention provides methods for detecting a viral target nucleic acid, comprising: a) linearly amplifying a first region of the viral target nucleic acid to generate linearly amplified amplification products; b) exponentially amplifying a second region of the viral target nucleic acid to generate exponentially amplified amplification products; c) hybridizing the linearly amplified amplification products with a first set of probes and the exponentially amplified amplification products with a second set of probes, wherein either the first or the second set of probes comprises a first plurality of probes that hybridize to amplified viral target nucleic acid and a second plurality of probes that hybridize to amplified viral target nucleic acid at a different frequency than the first plurality of probes. In certain embodiments, both the first set and the second set of probes comprises a first plurality of probes that hybridize to amplified viral target nucleic acid and a second plurality of probes that hybridize to amplified viral target nucleic acid at a different frequency than the first plurality of probes.

In some embodiments, the present invention provides methods for detecting a viral target nucleic acid, comprising: a) amplifying a viral target nucleic acid both linearly and exponentially to generate amplification products; b) hybridizing the amplification products to at least two probes, wherein the first probe hybridizes to amplified viral target nucleic acid at a different frequency than the second probe. In certain embodiments, the first and second probes both hybridize to the same probe binding site on the viral target nucleic acid.

In certain embodiments, the present invention provides methods for detecting a viral target nucleic acid in a sample comprising; a) contacting a sample suspected of containing a viral target nucleic acid with amplification reagents such that, if the viral target nucleic acid is present: i) a first region of the viral target nucleic acid comprising a first probe hybridization site is either not amplified, or is amplified at a first level to generate plurality of first product sequences that comprise the first probe hybridization site; and ii) a second region of the viral target nucleic acid is amplified at a second level to generate a plurality of second product sequences that comprise a second probe hybridization site, wherein the second level of amplification is greater than the first level of amplification (e.g. such that the second product sequences are present at a level of at least 10-fold . . . 100-fold . . . 1000-fold . . . 10,000-fold . . . or 100,000-fold higher concentration after amplification that the viral target nucleic acid, or first product sequences if produced); and b) incubating the sample with a plurality of first and second probe oligonucleotides, wherein: i) the first and second probe oligonucleotides occupy the first probe hybridization site on the first region of the viral target nucleic acid, and the first product sequences if produced, at different frequencies, or ii) the first and second probe oligonucleotides occupy the second probe hybridization site on the second product sequences at a different frequency; and c) measuring hybridization of the first and second probe oligonucleotides thereby detecting the viral target nucleic acid in the sample. In particular embodiments, the second product sequences are present at a level between 100-fold and 100,000 fold higher concentration after amplification than the viral target nucleic acid, or first product sequences if produced.

In other embodiments, the methods further comprise incubating the sample with a third probe oligonucleotide that occupies the first probe hybridization site on the first region of the viral target nucleic acid, and the first product sequences if produced, at a first frequency, and measuring the hybridization of the third probe oligonucleotide. In some embodiments, the methods further comprise incubating the sample with a fourth probe oligonucleotide that occupies the first probe hybridization site on the first region of the viral target nucleic acid, and the first product sequences if produced, at a second frequency, wherein the second frequency is different from the first frequency, and measuring the hybridization of the fourth probe oligonucleotide.

In certain embodiments, the methods further comprise incubating the sample with a third probe oligonucleotide that occupies the second probe hybridization site on the second product sequences at a first frequency, and measuring the hybridization of the third probe oligonucleotide. In particular embodiments, the methods further comprise incubating the sample with a fourth probe oligonucleotide that occupies the second probe hybridization site on the second product sequences at a second frequency, wherein the second frequency is different from the first frequency, and measuring the hybridization of the fourth probe oligonucleotide.

In some embodiments, the first level of amplification is achieved by linear amplification, and the second level is achieved is achieved with logarithmic amplification (e.g., polymerase chain reaction). In further embodiments, the first level of amplification is achieved with compromised amplification (e.g. using inefficient primers and/or inefficient polymerases). In other embodiments, the second level of amplification is at least 10-fold greater than no amplification or the first level of amplification.

In some embodiments, the present invention provides methods for detecting a viral target nucleic acid in a sample, comprising; a) contacting a sample suspected of containing a viral target nucleic acid with amplification reagents such that, if the viral target nucleic acid is present: i) a first region of the viral target nucleic acid is amplified non-logarithmically to generate a plurality of non-logarithmically amplified sequences that comprise a first probe hybridization site, and ii) a second region of the viral target nucleic acid is amplified logarithmically to generate a plurality of logarithmically amplified sequences that comprise a second probe hybridization site; b) incubating the sample with a plurality of first probe oligonucleotides, a plurality of second probe oligonucleotides, and a plurality of third probe oligonucleotides, wherein each of the first, second, and third probe oligonucleotides comprises an analyte specific region, wherein the plurality of second probe oligonucleotides are configured to occupy the second probe hybridization site on the logarithmically amplified sequences at a different frequency than the plurality of first probe oligonucleotides, and wherein the third probe oligonucleotides are configured to occupy the first probe hybridization site on the non-logarithmically amplified sequences at a first frequency; and c) measuring hybridization of the first, second, and third probe oligonucleotides, thereby detecting the viral target nucleic acid in the sample. In other embodiments, the viral target nucleic acid is initially present in the sample in an amount between about $10^1$ and about $10^8$ molecules (e.g. the dynamic range of the methods extend over at least about seven orders of magnitude).

In certain embodiments, the measuring detects the amount of the viral target nucleic acid in the sample. In other embodiments, the measuring is conduced over time. In further embodiments, the plurality of logarithmically amplified sequences do not contain the first probe hybridization site.

In particular embodiments, the analyte specific regions of the first probe oligonucleotides are completely complementary to the second probe hybridization site of the second product sequence (e.g. logarithmically amplified sequences). In other embodiments, the analyte specific regions of the second probe oligonucleotides are partially complementary to the second probe hybridization site of the second product sequences (e.g., logarithmically amplified sequences).

In certain embodiments, the methods further comprise incubating the sample with a plurality of fourth probe oligonucleotides comprising an analyte specific region, wherein the fourth probe oligonucleotides are configured to occupy the first probe hybridization site on the first product sequences (e.g., non-logarithmically amplified sequences) at a second frequency which is different from the first frequency of the third probe oligonucleotides. In further embodiments, the viral target nucleic acid is initially present in the sample in an amount between about $10^1$ and about $10^{10}$ molecules (e.g. the dynamic range of the methods extend over at least about nine orders of magnitude).

In further embodiments, the analyte specific regions of the third probe oligonucleotides are completely complementary to the first probe hybridization site of the first product sequences (e.g., non-logarithmically amplified sequences). In other embodiments, the analyte specific regions of the third probe oligonucleotides are partially complementary to the first probe hybridization site of the first product sequences (e.g, non-logarithmically amplified sequences). In additional embodiments, the analyte specific regions of the third oligonucleotides are identical to the analyte specific regions of the fourth oligonucleotides.

In some embodiments, the second probe oligonucleotides are present in at least a 5-fold lower concentration than the first probe oligonucleotides (e.g. 5-fold, 6-fold, 7-fold, 8-fold, or 9-fold lower concentration). In certain embodiments, the second probe oligonucleotides are present in at least a 10-fold lower concentration than the first probe oligonucleotides (e.g. 10-fold . . . 15-fold . . . 25-fold . . . 50-fold . . . 75-fold . . . or 95-fold lower concentration, or any range between 10-fold and 100-fold). In particular embodiments, the second probe oligonucleotides are present in at least a 100-fold lower concentration than the first probe oligonucleotides (e.g. 100-fold . . . 125-fold . . . 150-fold . . . 250-fold . . . 500-fold . . . 750-fold . . . or 900-fold lower concentration, or any range between 100-fold and 1000-fold). In further embodiments, the second probe oligonucleotides are present in at least a 1000-fold lower concentration than the first probe oligonucleotides (e.g., 1000-fold . . . 1100-fold . . . 1300-fold . . . 1500-fold . . . 10,000-fold . . . 15,000-fold . . . 25,000-fold . . . 100,000-fold . . . 500,000-fold . . . or 1,000,000-fold, or any range between 1000-fold and 1,000,000-fold).

In some embodiments, the third probe oligonucleotides are present in at least a 5-fold lower concentration than the fourth probe oligonucleotides (e.g. 5-fold, 6-fold, 7-fold, 8-fold, or 9-fold lower concentration). In certain embodiments, the third probe oligonucleotides are present in at least a 10-fold lower concentration than the fourth probe oligonucleotides (e.g. 10-fold . . . 15-fold . . . 25-fold . . . 50-fold . . . 75-fold . . . or 95-fold lower concentration, or any range between 10-fold and 100-fold). In particular embodiments, the third probe oligonucleotides are present in at least a 100-fold lower concentration than the fourth probe oligonucleotides (e.g. 100-fold . . . 125-fold . . . 150-fold . . . 250-fold . . . 500-fold . . . 750-fold . . . or 900-fold lower concentration, or any range between 100-fold and 1000-fold). In further embodiments, the third probe oligonucleotides are present in at least a 1000-fold lower concentration than the fourth probe oligonucleotides (e.g., 1000-fold . . . 1100-fold . . . 1300-fold . . . 1500-fold . . . 10,000-fold . . . 15,000-fold . . . 25,000-fold . . . 100,000-fold . . . 500,000-fold . . . or 1,000,000-fold, or any range between 1000-fold and 1,000,000-fold).

In certain embodiments, the viral target nucleic acid is initially present in the sample in an amount between about $10^1$ and about $10^3$ molecules, and the amount of the viral target nucleic acid is determined by the measuring hybridization of the first probe oligonucleotides. In other embodiments, the viral target nucleic acid is initially present in the sample in an amount between about $10^3$ and about $10^6$ molecules, and the amount of the viral target nucleic acid is determined by the measuring hybridization of the second probe oligonucleotides. In some embodiments, the viral target nucleic acid is initially present in the sample in an amount between about $10^6$ and about $10^8$ molecules, and the amount of the viral target nucleic acid is determined by the measuring hybridization of the third probe oligonucleotides.

In certain embodiments, the method is conducted on two samples, wherein the viral target nucleic acid is initially present in one sample in an amount less than $10^3$ and initially present in a second sample in an amount greater than $10^5$. In other embodiments, the method is conducted on two samples, wherein the viral target nucleic acid is initially present in one sample in an amount less than $10^2$ and initially present in a second sample in an amount greater than $10^6$. In further embodiments, the method is conducted on two samples, wherein the viral target nucleic acid is initially present in one sample in an amount less than $10^1$ and initially present in a second sample in an amount greater than $10^7$, or greater than $10^8$, or greater than $10^9$.

In particular embodiments, the plurality of first product sequences (e.g, non-logarithmically amplified sequences) further comprise the second probe hybridization site. In other embodiments, the plurality of second product sequences (e.g., non-logarithmically amplified sequences) do not contain the second probe hybridization site. In certain embodiments, the non-logarithmic amplification of the first region comprises single-stranded PCR or compromised PCR.

In some embodiments, the first probe oligonucleotides further comprise a non-analyte specific region, wherein the non-analyte specific region comprises one or more nucleotides that are not complementary to the second product sequences (e.g, logarithmically amplified sequences). In other embodiments, the second probe oligonucleotides further comprise a non-analyte specific region, wherein the non-analyte specific region comprises one or more nucleotides that are not complementary to the second product sequences (e.g., logarithmically amplified sequences). In other embodiments, the third probe oligonucleotides further comprise a non-analyte specific region, wherein the non-analyte specific region comprises one or more nucleotides that are not complementary to the first product sequences (e.g, non-logarithmically amplified sequences). In further embodiments, the fourth probe oligonucleotides further comprise a non-analyte specific region, wherein the non-analyte specific region comprises one or more nucleotides that are not complementary to the first product sequences (e.g, non-logarithmically amplified sequences).

In certain embodiments, the analyte specific region of second probe oligonucleotide is shorter than the analyte specific region of the first probe oligonucleotide. In other embodiments, the analyte specific region of the fourth probe oligonucleotide is shorter than the analyte specific region of the third probe oligonucleotide.

In some embodiments, the first probe oligonucleotides comprise first labels and wherein the second probe oligonucleotides comprise second labels. In other embodiments, the third probe oligonucleotides comprise third labels and the fourth probe oligonucleotides comprise fourth labels. In particular embodiments, at least one of the first, second, or third oligonucleotides is unlabeled. In additional embodiments, the first, second, and third probe oligonucleotides are unlabeled. In some embodiments, the fourth probe oligonucleotides are un-labeled. In certain embodiments, the fourth probe oligonucleotides comprises a label. In other embodiments, the first, the second, and the third labels are different from each other or are the same as each other. In certain embodiments, the amplification reagents comprise first and second primers, and a polymerase.

In some embodiments, the first and second probe oligonucleotides further comprise a non-analyte specific region configured to not hybridize to the second probe hybridization site of the second product sequences (e.g, logarithmically amplified sequences), wherein the non-analyte specific region is 5' of the analyte specific region. In certain embodiments, the first and second probe oligonucleotides form an invasive cleavage structure with an upstream oligonucleotide, wherein the upstream oligonucleotide comprise a 5' portion and a 3' portion, wherein the 5' portion is configured to hybridize to a region contiguous with the second probe hybridization site on the second product sequences (e.g., logarithmically amplified sequences), and wherein the 3' portion is configured to not hybridize to the second product sequences (e.g., logarithmically amplified sequences). In other embodiments, the methods further comprise incubating the sample with a plurality of additional probe oligonucleotides comprising an analyte specific region, wherein the additional probe oligonucleotide is configured to occupy the second probe hybridization site on the second product sequences (e.g., logarithmically amplified sequences) at a frequency different that the first and second probe oligonucleotides.

In particular embodiments, the present invention provides methods for detecting an amount of a viral target nucleic acid in a sample, comprising; a) incubating a sample suspected of containing a viral target nucleic acid with a plurality of first probe oligonucleotides and a plurality of second probe oligonucleotides, wherein each of the first and the second probe oligonucleotides comprises an analyte specific region, wherein the plurality of second probe oligonucleotides are configured to occupy a probe hybridization site on the viral target nucleic acid with the same affinity as the plurality of first probe oligonucleotides, and wherein the plurality of second probe oligonucleotides are present in at least 5-fold lower concentration than the first probe oligonucleotides; and b) measuring hybridization of the first and the second probe oligonucleotides over time, thereby detecting the amount of the viral target nucleic acid. In some embodiments, the first probe oligonucleotides further comprise a first non-analyte specific region, and the second probe oligonucleotides further comprise a second non-analyte specific region which is not identical to the first non-analyte specific region. In other embodiments, the analyte specific regions of the first and second oligonucleotides have an identical sequence.

In additional embodiments, the present invention provides methods for detecting an amount of a viral target nucleic acid in a sample, comprising; a) incubating a sample suspected of containing a viral target nucleic acid with a plurality of un-labeled first probe oligonucleotides and a plurality of un-labeled second probe oligonucleotides, wherein each of the first and the second probe oligonucleotides comprises an analyte specific region, wherein the plurality of second probe oligonucleotides are configured to occupy a probe hybridization site on the viral target nucleic acid at a different frequency than the plurality of first probe oligonucleotides; and b) measuring hybridization of the first and the second probe oligonucleotides over time, thereby detecting the amount of the viral target nucleic acid.

In further embodiments, the present invention provides methods for detecting an initial amount of a viral target nucleic acid in a sample without amplifying initial amount of the viral target nucleic acid, comprising; a) incubating a sample initially containing 300 copies or less of a viral target nucleic acid with a plurality of first probe oligonucleotides and a plurality of second probe oligonucleotides, wherein each of the first and the second probe oligonucleotides comprises an analyte specific region, wherein the plurality of second probe oligonucleotides are configured to occupy a probe hybridization site on the viral target nucleic acid at a different frequency than the plurality of first probe oligonucleotides; b) measuring hybridization of the first and the second probe oligonucleotides over time, thereby measuring the amount of the viral target nucleic acid, wherein the 300 copies or less of the viral target nucleic acid are not amplified prior to the measuring step. In particular embodiments, the 300 copies or less is between 100 and 300 copies or between 100 and 200 copies.

In some embodiments, the present invention provides methods for detecting an amount of a viral target nucleic acid in a sample, comprising; a) contacting a sample suspected of containing viral target nucleic acid with amplification reagents such that, if the viral target nucleic acid is present, a region of the viral target nucleic acid containing a probe hybridization site is amplified to generate a plurality of amplified sequences, b) incubating the sample with a plurality of first probe oligonucleotides and a plurality of second probe oligonucleotides, wherein each of the first and the second probe oligonucleotides comprises an analyte specific region, wherein the plurality of second probe oligonucleotides are configured to occupy the a probe hybridization site on the amplified sequence at a different frequency than the plurality of first probe oligonucleotides; c) measuring hybridization of the first and the second probe oligonucleotides over time, thereby measuring the amount of the viral target nucleic acid, wherein the measuring is possible when the viral target nucleic acid is initially present in the sample in an amount between about 1 molecule and about $10^7$ molecules.

In certain embodiments, the incubating and measuring steps are conducted in a single vessel. In other embodiments, the contacting, incubating, and measuring steps are conducted in a single vessel. In further embodiments, the analyte specific regions of the first oligonucleotides are identical to the analyte specific regions of the second oligonucleotides. In some embodiments, the analyte specific regions of the second probe oligonucleotides contain a single mismatch with the logarithmically amplified sequences.

In some embodiments, the second or fourth probe oligonucleotides contain a charge tag. In other embodiments, the second or fourth probe oligonucleotide contains at least one modified nucleotide. In further embodiments, the second probe oligonucleotide has a lower or higher affinity for the second probe hybridization site than the first probe oligonucleotide. In particular embodiments, the second probe oligonucleotide has a lower or higher Tm with the second probe hybridization site than the first probe oligonucleotide. In additional embodiments, the fourth probe oligonucleotide has a lower or higher affinity for the first probe hybridization site than the third probe oligonucleotide. In other embodiments, the fourth probe oligonucleotide has a lower or higher Tm with the first probe hybridization site than the third probe oligonucleotide.

In some embodiments, the measuring hybridization of the first, second, and/or third, and/or fourth probe oligonucleotides comprises performing a hybridization assay. In particular embodiments, the hybridization assay is selected from the group consisting of a TAQMAN assay, SNP-IT assay, an invasive cleavage assay, a Southern blot, and a microarray assay. In further embodiments, the invasive cleavage assay in an INVADER assay.

In certain embodiments, the present invention provides methods for genotyping a polymorphic locus in a viral target nucleic acid in a sample, comprising; a) contacting a sample suspected of containing the viral target nucleic acid with amplification reagents such that, if the viral target nucleic acid is present, a region of the viral target nucleic acid containing the polymorphic locus is amplified to generate a plurality of amplified sequences, wherein the amplification is conducted until saturation; b) incubating the sample with a plurality of first probe oligonucleotides and a plurality of second probe oligonucleotides, wherein each of the first probe oligonucleotides comprises: i) a first analyte specific region configured for detecting a first allele at the polymorphic locus, and ii) a label capable of generating a detectable signal or a cleavable portion configured to cause a detectable signal to be generated, and wherein the second probe oligonucleotides comprise: i) a second analyte specific region configured for detecting a second allele at the polymorphic locus, ii) a label capable of generating a detectable signal or a cleavable portion configured to cause a detectable signal to be generated, wherein the plurality of second probe oligonucleotides are configured to occupy a probe hybridization site on the amplified sequences at a different frequency than the plurality of first probe oligonucleotides, and wherein the type of detectable signal from the first and second probe oligonucleotides is the same; c) measuring the strength of the detectable signal generated, thereby determining the presence of the first allele, the second allele, or both the first and second alleles in the viral target nucleic acid. In certain embodiments, the polymorphic locus is a single nucleotide polymorphism. In other embodiments, the polymorphic locus is a repeat sequence.

In some embodiments, the present invention provides methods for detecting a viral target nucleic acid in a sample, comprising; a) incubating a sample suspected of containing a viral target nucleic acid with a plurality of first and second probe oligonucleotides, a plurality of upstream oligonucleotides, and a cleavage agent, wherein each of the first probe oligonucleotides comprise: i) a first analyte specific region configured to hybridize to a probe hybridization site on the viral target nucleic acid, and ii) a first non-analyte specific region configured to not hybridize to the viral target nucleic acid, wherein the first non-analyte specific region is 5' of the first analyte specific region, and wherein each of the second probe oligonucleotides comprises i) a second analyte specific region configured to hybridize to the probe hybridization site on the viral target nucleic acid, and ii) a second non-analyte specific region configured to not hybridize to the viral target nucleic acid, wherein the second non-analyte specific region is not identical to the first non-analyte specific region, and wherein the plurality of second probe oligonucleotides are configured to occupy the probe hybridization site on the viral target nucleic acid at a different frequency than the plurality of first probe oligonucleotides; wherein the incubating is under conditions such that invasive cleavage structures are formed resulting in the cleavage of both the first and second probe oligonucleotides by the cleavage agent to generate: i) first non-viral target cleavage products comprising the first non-analyte specific region, and ii) second non-viral target cleavage products comprising the second non-analyte specific region; and b) measuring hybridization of the first and the second probe oligonucleotides by detecting a signal generated by the first and second non-viral target cleavage products, thereby detecting the viral target nucleic acid. In some embodiments, the amount of the viral target is detected.

In certain embodiments, the present invention provides methods for detecting a viral target nucleic acid in a sample, comprising; a) incubating a sample suspected of containing a viral target nucleic acid with a plurality of first and second probe oligonucleotides, a plurality of first upstream oligonucleotides, a plurality of second upstream oligonucleotides, and a cleavage agent, wherein each of the first probe oligonucleotides comprise: i) a first analyte specific region configured to hybridize to a first probe hybridization site on the viral target nucleic acid, and ii) a first non-analyte specific region configured to not hybridize to the viral target nucleic acid, wherein the first non-analyte specific region is 5' of the first analyte specific region, and wherein each of the second probe oligonucleotides comprises i) a second analyte specific region configured to hybridize to a second probe hybridization site on the viral target nucleic acid, wherein the second probe hybridization site is not the same as the first probe hybridization site, and ii) a second non-analyte specific region configured to not hybridize to the viral target nucleic acid, wherein the second non-analyte specific region is not identical to the first non-analyte specific region, and wherein the plurality of second probe oligonucleotides are present in at least 5-fold lower concentration than the first probe oligonucleotides; wherein the incubating is under conditions such that invasive cleavage structures are formed resulting in the cleavage of both the first and second probe oligonucleotides by the cleavage agent to generate: i) first non-viral target cleavage products comprising the first non-analyte specific region, and ii) second non-viral target cleavage products comprising the second non-analyte specific region; and b) measuring hybridization of the first and the second probe oligonucleotides over time by detecting a signal generated by the first and second non-viral target cleavage products, thereby measuring the amount of the viral target nucleic acid. In some embodiments, the amount of the viral target is detected.

In certain embodiments, the second probe oligonucleotides are present in at least a 10-fold, 100-fold, or 1000-fold, lower concentration than the first probe oligonucleotides. In further embodiments, the signal generated by the first and second non-viral target cleavage products is the same. In other embodiments, the signal generated by the first and second non-viral target cleavage products is different. In some embodiments, the upstream oligonucleotides comprise a 5' portion and a 3' portion, wherein the 5' portion is configured to hybridize to a region contiguous with the probe hybridization site on the viral target nucleic acid, and wherein the 3' portion is configured to not hybridize to the viral target nucleic acid. In further embodiments, the methods further comprise incubating the sample with first and second labeled sequences, wherein the first labeled sequence is configured to generate a first detectable signal when hybridized to the first non-viral target cleavage product, and wherein the second labeled sequence is configured to generate a second detectable signal when hybridized to the second non-viral target cleavage product. In particular embodiments, the first and second detectable signals are the same. In additional embodiments, the first and second labeled sequences comprise FRET cassettes. In other embodiments, the plurality of upstream oligonucleotides are generated in the sample (e.g., by a polymerase). In some embodiments, the upstream oligonucleotides are supplied pre-synthesized.

In certain embodiments, the present invention provides kits for quantitation of viral target nucleic acids in a sample, comprising: a) a plurality of first probe oligonucleotides, wherein each of the first probe oligonucleotides comprises a first analyte specific region, wherein the first probe oligonucleotides are un-labeled, or comprise a label, b) a plurality of second probe oligonucleotides, wherein each of the second probe oligonucleotides comprises a second analyte specific region, wherein the second probe oligonucleotides are un-labeled, or comprise a label, wherein the plurality of second probe oligonucleotides are configured to occupy a probe hybridization site on the viral target nucleic acids at a different frequency than the plurality of first probe oligonucleotides; and c) reagents for performing an INVADER assay using the pluralities of the first and second probe oligonucleotides.

In certain embodiments, the present invention provides kits or compositions comprising: i) a plurality of first oligonucleotides, and ii) a plurality of second probe oligonucleotides, wherein the first probe oligonucleotides comprise a first 5' region and a first 3' region, and the second probe oligonucleotides comprises a second 5' region and a second 3' region, wherein both of the first and second probe oligonucleotides will form an invasive cleavage structure in the presence of the same upstream oligonucleotide and viral target sequence, and will both be cleaved by the same cleavage agent to form a first 5' region product and a second 5' region product, wherein the second 5' region product is not identical to the first 5' region product. In some embodiments, the kit or composition further comprises iii) first and second labeled sequences, wherein the first labeled sequence is configured to generate a first detectable signal when hybridized to the first 5' region product, and wherein the second labeled sequence is configured to generate a second detectable signal when hybridized to the second 5' region product. In some embodiments, the kits further comprise the viral target sequence as a control.

In particular embodiments, the first and second probe oligonucleotides are provides in a first vessel. In further embodiments, the, and kit further comprises a second vessel containing a polymerase and FEN enzyme. In additional embodiments, the kit further comprises a third vessel containing a buffer.

In some embodiments, the first 3' region and the second 3' region have the identical sequence. In other embodiments, the first 3' region and the second 3' region do not have identical sequences. In particular embodiments, the second probe oligonucleotides are present in at least a 5 fold lower concentration than the first probe oligonucleotides. In other embodiments, the second probe oligonucleotides are present in at least a 10 fold . . . 100-fold . . . 1000-fold . . . 10,000-fold . . . or 500,000 lower concentration than the first probe oligonucleotides. In some embodiments, the first and second probe oligonucleotides are un-labeled.

In further embodiments, the kits or compositions further comprise a third probe oligonucleotide comprising a third 5' region and a third 3' region, wherein the third probe oligonucleotide will not form an invasive cleavage structure with the viral target and the upstream oligonucleotide that is cleavable by the cleavage agent. In some embodiments, the first and second detectable signals are the same or they are different.

In some embodiments, the present invention provides kits comprising i) a plurality of un-labeled first probe oligonucleotides and ii) a plurality of un-labeled second probe oligonucleotides, wherein the first and second probe oligonucleotides comprises an analyte specific region, wherein the plurality of second probe oligonucleotides are configured to occupy a probe hybridization site on a viral target nucleic acid at a different frequency than the plurality of first probe oligonucleotides. In further embodiments, the kits further comprise a polymerase and/or a FEN enzyme. In other embodiments, the kits further comprise a buffer.

In some embodiments, the present invention provides kits comprising; a) a first vessel comprising a plurality of first probe oligonucleotides (e.g., unlabeled) and a plurality of second probe oligonucleotides (e.g., unlabeled), wherein the first and second probe oligonucleotides comprises an analyte specific region, wherein the plurality of second probe oligonucleotides are configured to occupy a probe hybridization site on a viral target nucleic acid at a different frequency than the plurality of first probe oligonucleotides; b) a second vessel comprising a polymerase and/or a FEN enzyme, and c) a third vessel comprising a buffer. In certain embodiments, the kits further comprise d) a control viral target sequence comprising the probe hybridization site.

In particular embodiments, the present invention provides kits and compositions comprising; a) a plurality of first and second probe oligonucleotides, wherein the first probe oligonucleotides comprise a first 5' region and a first 3' region, and the second probe oligonucleotides comprises a second 5' region and a second 3' region, wherein both of the first and second probe oligonucleotides will form an invasive cleavage structure in the presence of the same upstream oligonucleotide and viral target sequence, and will both be cleaved by the same cleavage agent to form a first 5' region product and a second 5' region product, wherein the second 5' region product is identical to the first 5' region product, and wherein the first 3' region is not identical to the second 3' region, and b) first labeled sequences, wherein the first labeled sequence is configured to generate a detectable signal when hybridized to the first or second 5' region product.

In some embodiments, the present invention provides methods for detecting at least two different viral, type or subtypes, species in a single reaction vessel comprising; a) providing a reaction vessel containing a sample, wherein the sample is suspected of containing first and second viral target nucleic acids, wherein the first viral target nucleic acids are from a viral species different from the second viral target nucleic acids; b) incubating the sample in the reaction vessel with a plurality of first and second probes, a plurality of first and second reporter sequences, and a cleavage agent under conditions such that: i) the first probes hybridize to first viral target nucleic acids and are cleaved by the cleavage agent thereby generating first 5' cleaved portions, and ii) the second probes hybridize to second viral target nucleic acids and are cleaved by the cleavage agent thereby generating second 5' cleaved portions; and c) detecting a signal from the sample in the reaction vessel, wherein the signal is from the first and second reporter sequences and is generated by hybridization of the first 5' cleaved portions to the first reporter sequences and hybridization of the second 5' cleaved portions to the second reporter sequences, thereby detecting the presence of both the first and second target nucleic acids in the sample.

In certain embodiments, the present invention provides methods for detecting at least two different viral species in a single reaction vessel comprising; a) providing a reaction vessel containing a sample, wherein the sample is suspected of containing first and second viral target nucleic acids, wherein the first viral target nucleic acids are from a viral species different from the second viral target nucleic acids; b) incubating the sample in the reaction vessel with a plurality of first and second probes, a plurality of reporter sequences, and a cleavage agent under conditions such that: i) the first probes hybridize to first viral target nucleic acids and are cleaved by the cleavage agent thereby generating first 5' cleaved portions, and ii) the second probes hybridize to second viral target nucleic acids and are cleaved by the cleavage agent thereby generating second 5' cleaved portions; and c) detecting a signal from the sample in the reaction vessel, wherein the signal is from the reporter sequences and is generated by hybridization of the first and second 5' cleaved portions to the reporter sequences thereby detecting the presence of both the first and second target nucleic acids in the sample. In particular embodiments, the first and second 5' cleaved portions are identical to each other.

In other embodiments, the first viral target nucleic acid comprises at least a portion of a first viral genome (e.g., hepatitis C virus) or an amplified portion of the first viral genome. In certain embodiments, the second viral target nucleic acid comprises at least a portion of a second viral genome or an amplified portion of the second viral genome. In particular embodiments, the first viral target nucleic acids comprise at least a portion of, or an amplified portion of, a RNA viral genome and the second viral target nucleic acids comprise at least a portion of, or an amplified portion of, a DNA viral genome. In some embodiments, the first viral target nucleic acids comprise cDNA copies of a portion of a first viral genome. In other embodiments, the first or second viral target nucleic acids are amplified prior to step b). In some embodiments, the first and second viral target nucleic acids are amplified prior to step b). In additional embodiments, the signal is generated by cleavage of the reporter sequences.

In certain embodiments, the first and second probes are cleaved as part of an invasive cleavage reaction. In certain embodiments, the incubating further comprises incubating the sample with first upstream oligonucleotides configured to form invasive cleavage structures with the first probes and the first viral target nucleic acids. In other embodiments, the incubating further comprises incubating the sample with second upstream oligonucleotides configured to form invasive cleavage structures with the second probes and the second target nucleic acids.

In particular embodiments, the reporter sequences comprise a dye and a quencher. In other embodiments, the first and second 5' cleaved portions are configured to not hybridize to the first and second viral target nucleic acids. In some embodiments, the first viral target nucleic acid comprises at least a portion of an HCV viral genome or an amplified portion of the HCV viral genome. In other embodiments, the second viral target nucleic acid comprises at least a portion of and HSV-1 viral genome or an amplified portion of the HSV-1 viral genome.

In some embodiments, the present invention provides methods for detecting the presence or absence of a target nucleic acid in a sample comprising; a) incubating the sample with a stem oligonucleotide, an upstream oligonucleotide, a downstream probe, and a cleavage agent under conditions such that, if the target nucleic acid is present: i) a 3' target specific region of the stem oligonucleotide hybridizes to the target nucleic acid, and a stem region of the stem oligonucleotide remains available for hybridization to a portion of the upstream oligonucleotide and the downstream probe, ii) a 5' target specific region of the upstream oligonucleotide hybridizes to the target nucleic acid, and a stem specific region of the upstream oligonucleotide hybridizes to a portion of the stem region of the stem oligonucleotide, iii) a 3' region of the downstream probe hybridizes to a portion of the stem region of the stem oligonucleotide, and a 5' region of the downstream probe does not hybridize to the stem region of the stem oligonucleotide, wherein the downstream probe forms an invasive cleavage structure with the upstream oligonucleotide and the stem region of the stem oligonucleotide, and iv) the cleavage agent cleaves the downstream probe in the invasive cleavage structure thereby generating a 5' cleaved portion; and b) detecting the presence or absence of the target nucleic acid in the sample.

In certain embodiments, the detecting comprises determining if the 5' cleaved portion has been generated. In other embodiments, the incubating further includes a reporter sequence, and the detecting the presence or absence of the target nucleic acid comprises detecting a signal from the reporter sequence generated by hybridization of the 5' cleaved portion to the reporter sequence. In particular embodiments, the hybridization of the 5' cleaved portion to the reporter sequence generates an invasive cleavage structure that is cleaved by the cleavage agent.

In certain embodiments, the target nucleic acid is composed of RNA and the reporter sequence is composed of DNA. In further embodiments, the target nucleic acid comprises RNA. In other embodiments, the target nucleic acid comprises viral RNA. In some embodiments, the upstream oligonucleotide comprises a 3' region configured to not hybridize to the stem region of the stem oligonucleotide. In further embodiments, the upstream oligonucleotide comprises a 3' region configured to hybridize to the stem region of the stem oligonucleotide. In other embodiments, the stem specific region of the upstream oligonucleotide is between 5 and 12 bases in length (e.g., 5, 6, 7, 8, 9, 10, 11, or 12 bases in length). In particular embodiments, the stem specific region of the upstream oligonucleotide is 8 or 9 bases in length.

In some embodiments, the 5' target specific region of the upstream oligonucleotide is partially or fully complementary to the target nucleic acid. In other embodiments, the 5' target specific region of the upstream oligonucleotide is between 20 and 60 bases in length (e.g., 20, 30, 40, 50, or 60 bases). In additional embodiments, the 5' target specific region of the upstream oligonucleotide has a Tm of about 20 degrees Celsius (e.g. 15, 16, 17, 18, 19, 20, 21, 22, 23, 24, or 25 degrees Celsius).

In other embodiments, the 3' target specific region of the stem oligonucleotide is partially or fully complementary to the target nucleic acid. In certain embodiments, the 3' target specific region of the stem oligonucleotide is between 15 and 50 bases in length (e.g., 15 . . . 25 . . . 35 . . . or 50 bases in length). In some embodiments, the stem and upstream oligonucleotides are present in step a) at a concentration of less than 10 nM. In other embodiments, the stem and upstream oligonucleotides are present in step a) at a concentration of about 100-300 pM (e.g., 100 pM . . . 150 pM . . . 200 pM . . . 250 pM . . . or 300 pM).

In certain embodiments, polymerization is employed to create at least a portion of one or more of the following sequences: the stem oligonucleotide, the upstream, or the downstream probe. In other embodiments, the stem oligonucleotide is blocked on the 3' end, the 5' end, or both the 3' and the 5' ends (e.g. with one or more 2'-O-methylated bases). In further embodiments, the upstream oligonucleotide is blocked on the 5' end. (e.g. with one or more 2'-O-methylated bases).

In some embodiments, the incubating further includes a polymerase, a primer, and dNTPs, and wherein the incubating is under conditions such that the polymerase extends the 3' end of the upstream oligonucleotide using the stem region of the stem oligonucleotide as a template to generate an extended upstream oligonucleotide that comprises an upstream oligonucleotide extended region. In other embodiments, the methods further comprise heating the sample in order to separate the extended upstream oligonucleotide from the stem oligonucleotide and the target nucleic acid. In particular embodiments, the methods further comprise cooling the sample under conditions such that the primer hybridizes to at least a portion of the upstream oligonucleotide extended region of the extended upstream oligonucleotide. In additional embodiments, the methods further comprise incubating the sample under conditions such that the primer is extended by the polymerase using the extended upstream oligonucleotide as a template such that a stem amplicon sequence is generated. In particular embodiments, the methods further comprise heating the sample in order to separate the stem amplicon sequence from the extended upstream oligonucleotide. In other embodiments, the methods further comprise incubating the sample with a downstream probe and upstream oligonucleotide such that an invasive cleavages structure is formed with the stem amplicon sequence, the downstream probe, and the upstream oligonucleotide.

In some embodiments, the present invention provides methods of target nucleic acid dependent amplification of a non-target sequence in a sample comprising; a) incubating the sample with stem oligonucleotides, upstream oligonucleotides, primers, dNTPs, and a polymerase under conditions such that, if the target nucleic acid is present: i) a 3' target specific region of the stem oligonucleotides hybridizes to the target nucleic acid, and a stem region of the stem oligonucleotides remains available for hybridization to the upstream oligonucleotides, ii) a 5' target specific region of the upstream oligonucleotides hybridizes to the target nucleic acid, and a stem specific region of the upstream oligonucleotides hybridizes to a portion of the stem region of the stem oligonucleotides, and iii) the polymerase extends the 3' end of the upstream oligonucleotides using the stem region of the stem oligonucleotides as a template to generate extended upstream oligonucleotides that comprise an upstream oligonucleotide extended region; b) heating the sample in order to separate the extended upstream oligonucleotides from the stem oligonucleotides and the target nucleic acid; c) cooling the sample under conditions such that the primers hybridize to at least a portion of the upstream oligonucleotide extended region of the extended upstream oligonucleotides; and d) incubating the sample under conditions such that the primers are extended by the polymerase using the extended upstream oligonucleotide as a template such that stem amplicon sequences are generated.

In certain embodiments, the methods further comprise the step of detecting the presence or absence of the target nucleic acid in the sample by determining if stem amplicon sequences are generated. In further embodiments, the methods further comprise the step of performing one or more rounds of PCR using the stem amplicon sequences and the extended upstream oligonucleotides as templates, wherein the upstream oligonucleotides prime polymerization from the stem amplicon sequences, and wherein the primers prime polymerization from the extended upstream oligonucleotides. In additional embodiments, the methods further comprise a step after step f) of detecting the presence or absence of the target nucleic acid in the sample by detecting any accumulated PCR products. In particular embodiments, the methods further comprise a step prior to step of heating the sample in order to separate the stem amplicon sequences from the extended upstream oligonucleotides. In some embodiments, the methods further comprise incubating the sample with downstream probes and upstream oligonucleotides such that invasive cleavage structure are formed with the stem amplicon sequences, the downstream probes, and the upstream oligonucleotides.

In particular embodiments, the present invention provides kits or compositions (e.g., reaction mixtures) comprising; a) a stem oligonucleotide, b) an upstream oligonucleotide, wherein the upstream oligonucleotide is configured to stably hybridize to the stem oligonucleotide only when both the stem and upstream oligonucleotides are hybridized to a target sequence, and c) a downstream probe, wherein the downstream probe comprises a 3' region configured to hybridize to a portion of the stem oligonucleotide and a 5' portion configured to not hybridize to the stem oligonucleotide, and wherein the downstream probe is configured to form an invasive cleavage structure with the upstream and stem oligonucleotides in the presence of the target sequence. In certain embodiments, the kits or compositions comprising a cleavage agent.

In some embodiments, the present invention provides kits and compositions (e.g., reaction mixtures) comprising; a) stem oligonucleotide, b) an upstream oligonucleotide, wherein the upstream oligonucleotide is configured to stably hybridize to the stem oligonucleotide only when both the stem and upstream oligonucleotides are hybridized to a target sequence, and c) a primer, wherein the primer is configured to hybridize to a region that is created by extending the 3' end of the upstream oligonucleotide with a polymerase and dNTPs when the stem and upstream oligonucleotides are hybridized together and hybridized to the target sequence. In other embodiments, the kits or compositions further comprise a polymerase.

In certain embodiments, the present invention provides methods, kits, compositions, and devices for nucleic dispensing, where the nucleic acid comprises a non-ionic detergent. In some embodiments, the present invention provides methods nucleic acid dispensing comprising; a) dispensing a nucleic acid mixture comprising a plurality of oligonucleotides onto a first surface region (e.g., a well) such that a first amount of the oligonucleotides are delivered to the first surface region, wherein the dispensing is through a hydrophobic polymer dispensing component (e.g. pipette tip) attached to, or integral with, a liquid dispensing device, and wherein the nucleic acid mixture further comprises a non-ionic detergent; and b) dispensing the nucleic acid mixture onto at least 15 additional surface regions (e.g., wells, which may or may not be part of the same device or component, such as a plate) through the hydrophobic polymer dispensing component attached to the liquid dispensing device such that the amount of the oligonucleotides delivered to each of the at least 15 additional surface regions is within about 15 percent of the first amount.

In particular embodiments, the first and/or additional surface regions are wells in the same plate. In other embodiments, the first and/or additional surface regions are wells in separate plates. In some embodiments, the first and/or additional surface regions are process chamber in the same or different microfluidic device components. In additional embodiments, the first and/or additional surface regions a test tubes, beakers, flasks, or other surface where it is desired to place a nucleic acid mixture.

In certain embodiments, the present invention provides liquid dispensing device comprising; a) a liquid holding reservoir, wherein the liquid holding reservoir contains a nucleic acid mixture comprising a plurality of oligonucleotides and a non-ionic detergent, wherein the non-ionic detergent makes up between about 0.005% and about 5.0% by volume of the nucleic acid mixture; b) at least one liquid dispensing channel operably linked to the liquid holding reservoir, c) a hydrophobic polymer dispensing component (e.g. pipette tip) attached to the at least one liquid dispensing channel.

In particular embodiments, the hydrophobic polymer dispensing component comprises a dispensing tip (e.g., Nano-Screen or Beckman pipette tip). In certain embodiments, the hydrophobic polymer dispensing component is composed of a material comprising polypropylene. In other embodiments, the hydrophobic polymer dispensing component is composed of a material selected from the group consisting of: polytetrafluoroethylene, polyethylene, or polypropylene.

In some embodiments, the amount of the oligonucleotides delivered to each of the additional surface regions is within about 10 percent of the first amount. In further embodiments, the amount of the oligonucleotides delivered to each of the additional surface regions is within about 7 percent of the first amount. In particular embodiments, the first amount delivered to the first surface region is the first contact of the hydrophobic polymer component with the nucleic acid mixture. In other embodiments, the first amount delivered to the first surface region is not the first contact of the hydrophobic polymer component with the nucleic acid mixture (e.g., the first amount is the tenth, or fifteenth, or thirty-first amount dispensed from the liquid dispensing device through the particular hydrophobic polymer component).

In certain embodiments, the non-ionic detergent makes up between about 0.005% and about 5.0% by volume of the nucleic acid mixture (e.g., 0.005% . . . 0.009% . . . 0.0015% . . . 0.09% . . . 0.55% . . . 1.0% . . . 2.5% . . . 4.0% . . . or 5%). In other embodiments, the non-ionic detergent makes up between about 0.005% and about 0.25% by volume of the nucleic acid mixture. In further embodiments, the non-ionic detergent makes up between about 0.005% and about 0.1% by volume of the nucleic acid mixture. In some embodiments, the non-ionic detergent makes up between about 0.005% and about 0.01% by volume of the nucleic acid mixture.

In certain embodiments, the at least 15 additional surface regions is at 16, at least 17, at least 18, at least 19, at least 20, at least 21, at least 22, at least 23, or at least 24 additional surface regions. In additional embodiments, the at least 15 additional surface regions is at least 25 additional surface regions (e.g., 25 . . . 35 . . . 45 . . . , or 50). In particular embodiments, the at least 15 additional surface regions is at least 50 surface regions (e.g. 50 wells . . . 65 wells . . . or 74 wells). In additional embodiments, the at least 15 additional surface regions is at least 75 wells (e.g., 75 wells . . . 85 wells . . . 95 wells . . . or 99 wells). In further embodiments, the at least 15 additional surface regions is at least 100 wells (e.g., 100 wells . . . 125 wells . . . 150 wells . . . 175 . . . 200 wells . . . 250 wells . . . 500 well . . . 1000 wells . . . or 10,000 wells).

In certain embodiments, the oligonucleotides are configured to produce a detectable signal in the presence of a target nucleic acid sequence. In further embodiments, the oligonucleotides are configured to participate in a nucleic acid detection assay selected from the group consisting of: a TAQMAN assay, an INVADER assay, a sequencing assay, a polymerase chain reaction assay, a hybridization assay, a hybridization assay employing a probe complementary to a mutation, a bead array assay, a primer extension assay, an enzyme mismatch cleavage assay, a branched hybridization assay, a rolling circle replication assay, a NASBA assay, a molecular beacon assay, a cycling probe assay, a ligase chain reaction assay, or a sandwich hybridization assay.

In some embodiments, the liquid dispensing device comprises an automated liquid dispensing device. In further embodiments, the liquid dispensing device comprises a hand-held liquid dispensing device. In other embodiments, the hydrophobic polymer dispensing component is one of 5 . . . 12 . . . 24 . . . 96 . . . 192 . . . 384 . . . 768 . . . 1,500 attached to the liquid dispensing device. In further embodiments, the volume of liquid dispensed into the first well is between about 10 and about 0.01 µL (e.g., 10 mL . . . 1 mL . . . 900 µL . . . 500 µL . . . 250 µL . . . 100 µL . . . 50 µL . . . 20 µL . . . 10 µL . . . 5 µL . . . 1 µL . . . 0.5 µL . . . 0.1 µL . . . or 0.01 Lµ). In some embodiments, the volume of liquid dispensed into each of the at least 15 additional wells is within about 5% of the volume of liquid dispensed into the first well (e.g. within about 0.1%, 1%, 2%, 3%, 4%, or 5% of the volume dispensed into the first well).

In certain embodiments, the first surface region and the at least 15 additional surface regions are formed in a microfluidic sample processing device component. In some embodiments, the microfluidic sample processing device component is configured to be combined with one or more additional components to generate a microfluidic sample processing device. In other embodiments, the at least 15 additional surface regions are process chambers for a microfluidic sample processing device. In further embodiments, the microfluidic sample processing device comprises: i) the process chambers, ii) a plurality of feeder conduits, wherein each of the plurality of feeder conduits is in fluid communication with at least one of the process chambers, iii) a main conduit which is in fluid communication with the plurality of feeder conduits, and iv) a loading chamber which is in fluid communication with the main conduit.

In certain embodiments, the nucleic acid mixture delivered to the at least 15 additional surface regions is dried down in the wells. In particular embodiments, the nucleic acid mixture contains a known concentration of a tracer dye. In further embodiments, the tracer dye comprises a free label. In other embodiments, the tracer dye comprises a fluorophore. In some embodiments, the tracer dye comprises a short oligonucleotide linked to a label (e.g. an oligonucleotide between 5 and 15 bases with a know sequence). In additional embodiments, the label comprises a fluorophore, chromophore, or radioactive label. In certain embodiments, the tracer dye comprises a mixture of both a free label and oligonucleotide linked label.

Other embodiments of the invention are described in the Detailed Description of the Invention and the Examples.

DEFINITIONS

To facilitate an understanding of the present invention, a number of terms and phrases are defined below:

As used herein, the term "dynamic range" refers to the quantitative range of usefulness in a detection assay (e.g., a nucleic acid detection assay). For example, the dynamic range of a viral detection assay is the range between the smallest number of viral particles (e.g., copy number) and the largest number of viral particles that the assay can distinguish between.

As used herein, the terms "subject" and "patient" refer to any organisms including plants, microorganisms and animals (e.g., mammals such as dogs, cats, livestock, and humans).

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases, which cleave nucleic acid molecules without regard to secondary structure (i.e., no formation of a duplexed structure is required).

The term "invasive cleavage structure" as used herein refers to a cleavage structure comprising i) a target nucleic acid, ii) an upstream nucleic acid (e.g., an INVADER oligonucleotide), and iii) a downstream nucleic acid (e.g., a probe), where the upstream and downstream nucleic acids anneal to contiguous regions of the target nucleic acid, and where an overlap forms between the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the CLEAVASE enzymes, the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; PCT Appln. Nos WO 98/23774; WO 02/070755A2; and WO0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher. In some embodiments the enzyme is functional or active at an elevated temperature of 65° C. or higher (e.g., 75° C., 85° C., 95° C., etc.).

The term "cleavage products" as used herein, refers to products generated by the reaction of a cleavage means with a cleavage structure (i.e., the treatment of a cleavage structure with a cleavage means).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]).

Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "analyte specific region" as used in reference to an oligonucleotide, such as a probe oligonucleotide or an INVADER oligonucleotide, refers to a region of an oligonucleotide selected to hybridize to a specific sequence in a target nucleic acid or set of target nucleic acids. In some embodiments, an analyte specific region may be completely complementary to the segment of a target nucleic acid to which it hybridizes, while in other embodiments, an analyte specific region may comprise one or more mismatches to the segment of a target nucleic acid to which it hybridizes. In yet other embodiments, an analyte specific region may comprise one or more base analogs, e.g., compounds that have altered hydrogen bonding, or that do not hydrogen bond, to the bases in the target strand. In some embodiments, the entire sequence of an oligonucleotide is an analyte specific region, while in other embodiments an oligonucleotide comprises an analyte specific region and one or more regions not complementary the target sequence (e.g., non-complementary flap regions).

The term "frequency" as used herein in reference to hybridization of nucleic acids refers to the probability that one particular nucleic acid (e.g., a probe oligonucleotide) will be base-paired to a complementary nucleic acid (e.g., a target nucleic acid) under particular hybridization conditions. The frequency of hybridization is influenced by many factors, including but not limited to the probability with which the complementary sequences will form a duplex under particular conditions (e.g., likelihood of encounter and of successful duplex formation) and the stability of the duplex, once formed. Reaction conditions that increase the likelihood of initial duplex formation between a probe and a target (e.g., increased concentration of one or both nucleic acids, absence of competitors such as other nucleic acids with sequences that can compete with a probe for binding to the target, or that can bind to the probe) can be said to increase the frequency of hybridization of between the probe and target (i.e., increase the frequency with which the probe oligonucleotide will occupy, or hybridize to, the complementary target strand). Similarly, reaction conditions and probe features that increase the stability of a hybrid between an oligonucleotide and another nucleic acid strand (or that slow disassociation of the strands, e.g., reduced reaction temperature, increased salt or divalent cation conditions, increased length of complementary regions, fewer mismatches, use of charged moieties favoring hybridization) can also be said to increase the frequency of hybridization of between the probe and target. Conversely, reaction conditions and probe features that decrease the likelihood of hybridization (e.g., reduction in concentration of one or both nucleic acids, the presence of a competitor or other additive that reduces the effective concentration of a probe or target strand) or that reduce the stability and/or life time of hybrids that are formed (e.g., increased reaction temperature, decreased salt or divalent cation conditions, decreased length of complementary regions, more mismatches, use of charged moieties disfavoring hybridization) are said to decrease the frequency of hybridization or occupation.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular target sequence (e.g. genomic DNA or viral DNA or RNA) that has not been amplified (e.g. by PCR), without creating copies of the target sequence. A "non-amplified oligonucleotide detection assay" may, for example, amplify a signal used to indicate the presence or absence of a particular polymorphism in a target sequence, so long as the target sequence is not copied.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism that is resistant to more than one of the antibiotics or antimicrobial agents used in the treatment of said microorganism.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n−1).

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As used herein, the term "sample" is used in its broadest sense. For example, in some embodiments, it is meant to include a specimen or culture (e.g., microbiological culture), whereas in other embodiments, it is meant to include both biological and environmental samples (e.g., suspected of comprising a target sequence, gene or template). In some embodiments, a sample may include a specimen of synthetic origin.

The present invention is not limited by the type of biological sample used or analyzed. The present invention is useful with a variety of biological samples including, but are not limited to, tissue (e.g., organ (e.g., heart, liver, brain, lung, stomach, intestine, spleen, kidney, pancreas, and reproductive (e.g., ovaries) organs), glandular, skin, and muscle tissue), cell (e.g., blood cell (e.g., lymphocyte or erythrocyte), muscle cell, tumor cell, and skin cell), gas, bodily fluid (e.g., blood or portion thereof, serum, plasma, urine, semen, saliva, etc), or solid (e.g., stool) samples obtained from a human (e.g., adult, infant, or embryo) or animal (e.g., cattle, poultry, mouse, rat, dog, pig, cat, horse, and the like). In some embodiments, biological samples may be solid food and/or feed products and/or ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Biological samples also include biopsies and tissue sections (e.g., biopsy or section of tumor, growth, rash, infection, or paraffin-embedded sections), medical or hospital samples (e.g., including, but not limited to, blood samples, saliva, buccal swab, cerebrospinal fluid, pleural fluid, milk, colostrum, lymph, sputum, vomitus, bile, semen, oocytes, cervical cells, amniotic fluid, urine, stool, hair and sweat), laboratory samples (e.g., subcellular fractions), and forensic samples (e.g., blood or tissue (e.g., spatter or residue), hair and skin cells containing nucleic acids), and archeological samples (e.g., fossilized organisms, tissue, or cells).

Environmental samples include, but are not limited to, environmental material such as surface matter, soil, water (e.g., freshwater or seawater), algae, lichens, geological samples, air containing materials containing nucleic acids, crystals, and industrial samples, as well as samples obtained from food and dairy processing instruments, apparatus, equipment, utensils, disposable and non-disposable items.

Other types of biological samples include bacteria (e.g., Actinobacteria (e.g., *Actinomyces, Arthrobacter, Corynebacterium* (e.g., *C. diphtheriae*)), *Mycobacterium* (e.g., *M. tuberculosis* and *M. leprae*), *Propionibacterium* (e.g., *P. acnes*), *Streptomyces*, Chlamydiae (e.g., *C. trachomatis* and *C. pneumoniae*), Cyanobacteria, *Deinococcus* (e.g., *Thermus* (e.g., *T. aquaticus*)), Firmicutes (e.g., Bacilli (e.g., *B. anthracis, B. cereus, B. thuringiensis*, and *B. subtilis*)), Listeria (e.g., *L. monocytogenes*), Staphylococcus (e.g., *S. aureus, S. epidermidis*, and *S. haemolyticus*), Fusobacteria, Proteobacteria (e.g., Rickettsiales, Sphingomonadales, *Bordetella* (e.g., *B. pertussis*), Neisserisales (e.g., *N. gonorrhoeae* and *N. meningitidis*), Enterobacteriales (e.g., *Escherichia* (e.g., *E. coli*), *Klebsiella, Plesiomonas, Proteus, Salmonella, Shigella*, and *Yersinia*), Legionellales, Pasteurellales (e.g., *Haemophilus influenzae*), Pseudomonas, Vibrio (e.g., *V. cholerae* and *V. vulnificus*), Campylobacterales (e.g., Campylobacteria (e.g., *C. jejuni*), and *Helicobacter* (e.g., *H. pylori*)), and Spirochaetes (e.g., *Leptospira, B. bergdorferi*, and *T. pallidum*)); Archaea (e.g., Halobacteria and Methanobacteria); Eucarya (e.g., Animalia (e.g., Annelidia, Arthropoda (e.g., Chelicerata, Myriapoda, Insecta, and Crustacea), Mollusca, Nematoda, (e.g., *C. elegans*, and *T. spiralis*) and Chordata (e.g., Actinopterygii, Amphibia, Aves, Chondrichthyes, Reptilia, and Mammalia (e.g., Primates, Rodentia, Lagomorpha, and Carnivora)))); Fungi (e.g., Dermatophytes, *Fusarium, Penicillum*, and *Saccharomyces*); Plantae (e.g., Magnoliophyta (e.g., Magnoliopsida and Liliopsida)), and Protista (e.g., Apicomplexa (e.g., *Cryptosporidium, Plasmodium* (e.g., *P. falciparum*, and *Toxoplasma*), and Metamonada (e.g., *G. lambia*))); and Viruses (e.g., dsDNA viruses (e.g., Bacteriophage, Adenoviridae, Herpesviridae, Papillomaviridae, Polyomaviridae, and Poxyiridae), ssDNA virues (e.g., Parvoviridae), dsRNA viruses (including Reoviridae), (+)ssRNA viruses (e.g., Coronaviridae, Astroviridae, Bromoviridae, Comoviridae, Flaviviridae, Picornaviridae, and Togaviridae), (−) ssRNA viruses (e.g., Bornaviridae, Filoviridae, Paramyxoviridae, Rhabdoviridae, Bunyaviridae, and Orthomyxoviridae), ssRNA-reverse transcribing viruses (e.g., Retroviridae), and dsDNA-reverse transcribing viruses (e.g., Hepadnaviridae and Caulomoviridae)).

Sample may be prepared by any desired or suitable method. In some embodiments, nucleic acids are analyzed directly from bodily fluids or other samples using the methods described in U.S. Pat. Pub. Serial No. 20050186588, herein incorporated by reference in its entirety.

The above described examples are not, however, to be construed as limiting the sample (e.g., suspected of comprising a target sequence, gene or template (e.g., the presence or absence of which can be determined using the compositions and methods of the present invention)) types applicable to the present invention.

The terms "nucleic acid sequence" and "nucleic acid molecule" as used herein refer to an oligonucleotide, nucleotide or polynucleotide, and fragments or portions thereof. The terms encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A nucleic acid sequence or molecule may be DNA or RNA, of either genomic or synthetic origin, that may be single or double stranded, and represent the sense or antisense strand. Thus, nucleic acid sequence may be dsDNA, ssDNA, mixed ssDNA, mixed dsDNA, dsDNA made into ssDNA (e.g., through melting, denaturing, helicases, etc.), A-, B-, or Z-DNA, triple-stranded DNA, RNA, ssRNA, dsRNA, mixed ss and dsRNA, dsRNA made into ssRNA (e.g., via melting, denaturing, helicases, etc.), messenger RNA (mRNA), ribosomal RNA (rRNA), transfer RNA (tRNA), catalytic RNA, snRNA, or protein nucleic acid (PNA).

The present invention is not limited by the type or source of nucleic acid (e.g., sequence or molecule (e.g. target sequence and/or oligonucleotide)) utilized. For example, the nucleic acid sequence may be amplified or created sequence (e.g., amplification or creation of nucleic acid sequence via synthesis (e.g., polymerization (e.g., primer extension (e.g., RNA-DNA hybrid primer technology)) and reverse transcription (e.g., of RNA into DNA)) and/or amplification (e.g., polymerase chain reaction (PCR), rolling circle amplification (RCA), nucleic acid sequence based amplification (NASBA), transcription mediated amplification (TMA), ligase chain reaction (LCR), cycling probe technology, Q-beta replicase, strand displacement amplification (SDA), branched-DNA signal amplification (bDNA), hybrid capture, and helicase dependent amplification).

The terms "nucleotide" and "base" are used interchangeably when used in reference to a nucleic acid sequence, unless indicated otherwise herein.

The term "nucleotide analog" as used herein refers to modified or non-naturally occurring nucleotides including, but not limited to, analogs that have altered stacking interactions such as 7-deaza purines (i.e., 7-deaza-dATP and 7-deaza-dGTP); base analogs with alternative hydrogen bonding configurations (e.g., Iso-C and Iso-G and other non-standard base pairs described in U.S. Pat. No. 6,001,983, herein incorporated by reference in its entirety); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242; B. A. Schweitzer and E. T. Kool, J. Am. Chem. Soc., 1995, 117, 1863-1872, each of which is herein incorporate by reference in its entirety); "universal" bases such as 5-nitroindole and 3-nitropyrrole; and universal purines and pyrimidines (e.g., "K" and "P" nucleotides, respectively; See, e.g., P. Kong, et al., Nucleic Acids Res., 1989, 17, 10373-10383; P. Kong et al., Nucleic Acids Res., 1992, 20, 5149-5152). Still other nucleotide analogs include modified forms of deoxyribonucleotides as well as ribonucleotides. Various oligonucleotides of the present invention (e.g., a primary probe or INVADER oligo) may contain nucleotide analogs.

The term "oligonucleotide" as used herein is defined as a molecule comprising two or more nucleotides (e.g., deoxyribonucleotides or ribonucleotides), preferably at least 5 nucleotides, more preferably at least about 10-15 nucleotides and more preferably at least about 15 to 30 nucleotides, or longer (e.g., oligonucleotides are typically less than 200 residues long (e.g., between 15 and 100 nucleotides), however, as used herein, the term is also intended to encompass longer polynucleotide chains). The exact size will depend on many factors, which in turn depend on the ultimate function or use of the oligonucleotide. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes. Oligonucleotides may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, the terms "complementary" or "complementarity" are used in reference to polynucleotides (e.g., a sequence of two or more nucleotides (e.g., an oligonucleotide or a target nucleic acid)) related by the base-pairing rules. For example, the sequence "5'-A-G-T-3'," is complementary to the sequence "3'-T-C-A-5'." Complementarity may be "partial," in which only some of the nucleic acid bases are matched according to the base pairing rules. Or, there may be "complete" or "total" complementarity between the nucleic acid bases. The degree of complementarity between nucleic acid strands has significant effects on the efficiency and strength of hybridization between nucleic acid strands. This is of particular importance in amplification reactions, as well as detection methods that depend upon the association of two or more nucleic acid strands. Either term may also be used in reference to individual nucleotides, especially within the context of polynucleotides. For example, a particular nucleotide within an oligonucleotide may be noted for its complementarity, or lack thereof, to a nucleotide within another nucleic acid sequence (e.g., a target sequence), in contrast or comparison to the complementarity between the rest of the oligonucleotide and the nucleic acid sequence.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "homology" refers to a degree of complementarity. There may be partial homology or complete homology (i.e., identity). A partially homologous sequence is one that is less than 100% identical to another sequence. A partially complementary sequence that is "substantially homologous" is a nucleic acid molecule that at least partially inhibits a completely complementary nucleic acid molecule from hybridizing to a target nucleic acid. The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (e.g., the hybridization) of a completely homologous nucleic acid molecule to a target under conditions of low stringency. This is not to say that conditions of low stringency are such that non-specific binding is permitted (e.g., the low stringency conditions may be such that the binding of two sequences to one another be a specific (e.g., selective) interaction). The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (e.g., is complementary to) the single-stranded nucleic acid sequence under conditions of low stringency as described above.

The terms "target nucleic acid" and "target sequence," when used in reference to an invasive cleavage reaction, refer to a nucleic acid molecule containing a sequence that has at least partial complementarity with at least a first nucleic acid molecule (e.g. probe oligonucleotide) and may also have at least partial complementarity with a second nucleic acid molecule (e.g. INVADER oligonucleotide). Generally, the target nucleic acid (e.g., present within, isolated from, enriched from, or amplified from or within a sample (e.g., a biological or environmental sample)) is located within a target region and is identifiable via the successful formation of an invasive cleavage structure in combination with a first and second nucleic acid molecule (e.g., probe oligonucleotide and INVADER oligonucleotide) that is cleavable by a cleavage agent. Target nucleic acids from an organism are not limited to genomic DNA and RNA. Target nucleic acids from an organism may comprise any nucleic acid species, including but not limited to genomic DNAs and RNAs, messenger RNAs, structural RNAs, ribosomal and tRNAs, and small RNAs such as snRNAs, siRNAs and microRNAs miRNAs). See, e.g., co-pending U.S. patent application Ser. No. 10/740, 256, filed Dec. 18, 2003, which is incorporated herein by reference in its entirety.

As used herein, the term "probe oligonucleotide," when used in reference to an invasive cleavage reaction, refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette," when used in reference to an invasive cleavage reaction, as used herein refers to an oligonucleotide or combination of oligonucleotides configured to generate a detectable signal in response to cleavage of a probe oligonucleotide in an INVADER assay. In preferred embodiments, the cassette hybridizes to an cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, the cassette comprises labeled moieties that produce a fluorescence resonance energy transfer (FRET) effect.

An oligonucleotide is said to be present in "excess" relative to another oligonucleotide (or target nucleic acid sequence) if that oligonucleotide is present at a higher molar concentration than the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present in at least a 100-fold molar excess; typically at least 1 pmole of each probe oligonucleotide would be used when the target nucleic acid sequence was present at about 10 fmoles or less.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species (e.g., a viral or bacterial gene present within a human host (e.g., extrachromosomally or integrated into the host's DNA)). A heterologous gene also includes a gene native to an organism that has been altered in some way (e.g., mutated, added in multiple copies, linked to non-native regulatory sequences, etc). In some embodiments, a heterologous gene can be distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (e.g., these flanking sequences can be located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (e.g., altered characteristics) when compared to the wild-type gene or gene product. It is noted that naturally occurring mutants can be isolated (e.g., identified by the fact that they have altered characteristics (e.g., altered nucleic acid sequences) when compared to the wild-type gene or gene product).

The term "isolated" when used in relation to a nucleic acid (e.g., "an isolated oligonucleotide" or "isolated polynucleotide" or "an isolated nucleic acid sequence") refers to a nucleic acid sequence that is separated from at least one component or contaminant with which it is ordinarily associated in its natural source. Thus, an isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (e.g., the oligonucleotide or polynucleotide may be single-stranded), but may contain both the sense and anti-sense strands (e.g., the oligonucleotide or polynucleotide may be double-stranded).

As used herein, the terms "purified" or "to purify" when used in reference to a sample (e.g., a molecule (e.g., a nucleic acid or amino acid sequence)) refers to removal (e.g., isolation and/or separation) of the sample from its natural environment. The term "substantially purified" refers to a sample (e.g., molecule (e.g. a nucleic acid or amino acid sequence) that has been removed (e.g., isolated and/or purified) from its natural environment and is at least 60% free, preferably 75% free, or most preferably 90% or more free from other components with which it is naturally associated. An "isolated polynucleotide" or "isolated oligonucleotide" may therefore be substantially purified if it is rendered free (e.g., 60%, 75% or more preferably 90% or more) from other components with which it is naturally associated.

The present invention is not limited to any particular means of purification (e.g., to generate purified or substantially purified molecules (e.g., nucleic acid sequences)). Indeed, a variety of purification techniques may be utilized including, but not limited to, centrifugation (e.g., isopycnic, rate-zonal, gradient, and differential centrifugation), electrophoresis (e.g., gel and capillary electrophoresis), gel filtration, matrix capture, charge capture, mass capture, antibody capture, magnetic separation, flow cytometry, and sequence-specific hybridization array capture.

As used herein, the term "hybridization" is used in reference to the pairing of complementary nucleic acids. Hybridization and the strength of hybridization (e.g., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See, e.g., Young and Anderson, (1985) in *Nucleic Acid Hybridisation: A Practical Approach* (Hames & Higgins, Eds.) pp 47-71, IRL Press, Oxford). Other computations for calculating $T_m$ are known in the art and take structural and environmental, as well as sequence characteristics into account (See, e.g., Allawi, H. T. and SantaLucia, J., Jr. Biochemistry 36, 10581-94 (1997)).

As used herein, the term "INVADER assay reagents" refers to one or more reagents for detecting target sequences, said reagents comprising nucleic acid molecules capable of forming an invasive cleavage structure in the presence of the target sequence. In some embodiments, the INVADER assay reagents further comprise an agent for detecting the presence of an invasive cleavage structure (e.g., a cleavage agent). In some embodiments, the nucleic acid molecules comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid. INVADER assay reagents may be found, for example, in U.S. Pat. Nos. 5,846,717; 5,985,557; 5,994,069; 6,001,567; 6,913,881; and 6,090,543, WO 97/27214, WO 98/42873, U.S. Pat. Publ. Nos. 20050014163, 20050074788, 2005016596, 20050186588, 20040203035, 20040018489, and 20050164177; U.S. patent application Ser. No. 11/266,723; and Lyamichev et al., Nat. Biotech., 17:292 (1999), Hall et al., PNAS, USA, 97:8272 (2000), each of which is herein incorporated by reference in its entirety for all purposes.

In some embodiments, INVADER assay reagents are configured to detect a target nucleic acid sequence comprising first and second non-contiguous single-stranded regions separated by an intervening region comprising a double-stranded region. In certain embodiments, the INVADER assay reagents comprise a bridging oligonucleotide capable of binding to said first and second non-contiguous single-stranded regions of a target nucleic acid sequence. In particularly preferred embodiments, either or both of said first and/or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support. The one or more oligonucleotides of the assay reagents may be linked to the solid support directly or indirectly (e.g., via a spacer molecule (e.g., an oligonucleotide)). Exemplary solid phase invasive cleavage reactions are described in U.S. Pat. Pub. Nos. 20050164177 and 20030143585, herein incorporated by reference in their entireties.

As used herein, a "solid support" is any material that maintains its shape under assay conditions, and that can be separated from a liquid phase. The present invention is not limited by the type of solid support utilized. Indeed, a variety of solid supports are contemplated to be useful in the present invention including, but not limited to, a bead, planar surface, controlled pore glass (CPG), a wafer, glass, silicon, plastic, paramagnetic bead, magnetic bead, latex bead, superparamagnetic bead, plurality of beads, microfluidic chip, a silicon chip, a microscope slide, a microplate well, a silica gel, a polymeric membrane, a particle, a derivatized plastic film, a glass bead, cotton, a plastic bead, an alumina gel, a polysaccharide, polyvinylchloride, polypropylene, polyethylene, nylon, Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch, polymeric microparticle, polymeric membrane, polymeric gel, glass slide, styrene, multi-well plate, column, microarray, latex, hydrogel, porous 3D hydrophilic polymer matrix (e.g., HYDROGEL, Packard Instrument Company, Meriden, Conn.), fiber optic bundles and beads (e.g., BEADARRAY (Illumina, San Diego, Calif.), described in U.S. Pat. App. 20050164177), small particles, membranes, frits, slides, micromachined chips, alkanethiol-gold layers, non-porous surfaces, addressable arrays, and polynucleotide-immobilizing media (e.g., described in U.S. Pat. App. 20050191660). In some embodiments, the solid support is coated with a binding layer or material (e.g., gold or streptavidin).

In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid (e.g., a stacker oligonucleotides). In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some embodiments one or more of the INVADER assay reagents may be provided in a predispensed format (e.g., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (e.g., including, but not limited to, a reaction tube or a well (e.g., a microtiter plate)). In certain preferred embodiments, the INVADER assay reagents are provided in microfluidic devices such as those described in U.S. Pat. Nos. 6,627,159; 6,720,187; 6,734,401; and 6,814,935, as well as U.S. Pat. Pub. 2002/0064885, each of which is herein incorporated by reference in its entirety. In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

As used herein, the term "label" refers to any moiety (e.g., chemical species) that can be detected or can lead to a detectable response. In some preferred embodiments, detection of a label provides quantifiable information. Labels can be any known detectable moiety, such as, for example, a radioactive label (e.g., radionuclides), a ligand (e.g., biotin or avidin), a chromophore (e.g., a dye or particle that imparts a detectable color), a hapten (e.g., digoxygenin), a mass label, latex beads, metal particles, a paramagnetic label, a luminescent compound (e.g., bioluminescent, phosphorescent or chemiluminescent labels) or a fluorescent compound.

A label may be joined, directly or indirectly, to an oligonucleotide or other biological molecule. Direct labeling can occur through bonds or interactions that link the label to the oligonucleotide, including covalent bonds or non-covalent interactions such as hydrogen bonding, hydrophobic and ionic interactions, or through formation of chelates or coordination complexes. Indirect labeling can occur through use of a bridging moiety or "linker", such as an antibody or additional oligonucleotide(s), which is/are either directly or indirectly labeled.

Labels can be used alone or in combination with moieties that can suppress (e.g., quench), excite, or transfer (e.g., shift) emission spectra (e.g., fluorescence resonance energy transfer (FRET)) of a label (e.g., a luminescent label).

As used herein, the term "FRET" refers to fluorescence resonance energy transfer, a process in which moeities (e.g., fluorphores) transfer energy (e.g., among themselves, or, from a fluorophore to a non-fluorophore (e.g., a quencher molecule)). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

As used herein, the term "donor" refers to a moiety (e.g., a fluorophore) that absorbs at a first wavelength and emits at a second, longer wavelength. The term "acceptor" refers to a moiety such as a fluorophore, chromophore, or quencher and that is able to absorb some or most of the emitted energy from the donor when it is near the donor group (typically between 1-100 nm). An acceptor may have an absorption spectrum that overlaps the donor's emission spectrum. Generally, if the acceptor is a fluorophore, it then re-emits at a third, still longer wavelength; if it is a chromophore or quencher, it releases the energy absorbed from the donor without emitting a photon. In some preferred embodiments, alteration in energy levels of donor and/or acceptor moieties are detected (e.g., via measuring energy transfer (e.g., by detecting light emission) between or from donors and/or acceptor moieties). In some preferred embodiments, the emission spectrum of an acceptor moiety is distinct from the emission spectrum of a donor moiety such that emissions (e.g., of light and/or energy) from the moieties can be distinguished (e.g., spectrally resolved) from each other.

In some embodiments, a donor moiety is used in combination with multiple acceptor moieties. In a preferred embodiment, a donor moiety is used in combination with a non-fluorescing quencher moiety and with an acceptor moiety, such that when the donor moiety is close (e.g. between 1-100 nm, or more preferably, between 1-25 nm, or even more preferably around 10 nm or less) to the quencher, its excitation is transferred to the quencher moiety rather than the acceptor moiety, and when the quencher moiety is removed (e.g., by cleavage of a probe), donor moiety excitation is transferred to an acceptor moiety. In some preferred embodiments, emission from the acceptor moiety is detected (e.g., using wavelength shifting molecular beacons) (See, e.g., Tyagi, et al., Nature Biotechnology 18:1191 (2000); Mhlanga and Malmberg, 2001 Methods 25, 463-471; Olivier, 2005 Mutant Res 573, 103-110, and U.S. Pat. App. 20030228703, each of which is incorporated herein by reference in its entirety).

Detection of labels or a detectable response (e.g., provided by the labels) can be measured using a multitude of techniques, systems and methods known in the art. For example, a label may be detected because the label provides detectable fluorescence (e.g., simple fluorescence, FRET, time-resolved fluorescence, fluorescence quenching, fluorescence polarization, etc.), radioactivity, chemiluminescence, electrochemiluminescence, RAMAN, colorimetry, gravimetry, hyrbridization (e.g., to a sequence in a hybridization protection assay), X-ray diffraction or absorption, magnetism, enzymatic activity, characteristics of mass or behavior affected by mass (e.g., MALDI time-of-flight mass spectrometry), and the like.

A label may be a charged moiety (positive or negative charge) or alternatively, may be charge neutral. Labels can include or consist of nucleic acid or protein sequence, so long as the sequence comprising the label is detectable. In some embodiments, the label is not nucleic acid or protein.

In some embodiments, a label comprises a particle for detection. For example, in some embodiments, the particle is a phosphor particle. An example of a phosphor particle includes, but is not limited to, an up-converting phosphor particle (See, e.g., Ostermayer, Preparation and properties of infrared-to-visible conversion phosphors. Metall. Trans. 752, 747-755 (1971)). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001); Corstjens, et al., IEEE Proc. Nanobiotechnol. 152(2):64 (2005), each incorporated by reference herein in its entirety.

As used herein, the term "distinct" in reference to signals (e.g., of one or more labels) refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

It will be apparent to one of skill in the art that there are a large number of methods (e.g., analytical procedures) that may be used to detect the presence or absence of a nucleic acid sequence (e.g., a gene (e.g., wild-type, mutant (e.g., comprising one or more variant nucleotides at one or more positions), heterologous, etc.)). Such methods include, but are not limited to, nucleic acid discrimination techniques, amplification reactions and/or a signal generating systems. Such methods include, but are not limited to, DNA sequencing, hybridization sequencing, protein truncation test, single-strand conformation polymorphism analysis (SSCP), denaturing gradient gel electrophoresis, temperature gradient gel electrophoresis, heteroduplex analysis, chemical mismatch cleavage, restriction enzyme digestion, and enzymatic mismatch cleavage, solid phase hybridization, dot blots, multiple allele specific diagnostic assays, reverse dot blots, oligonucleotide arrays (e.g., DNA chips), solution phase hybridization (e.g., TAQMAN (See, e.g., U.S. Pat. Nos. 5,210,015 and 5,487,972, each of which is herein incorporated by reference in its entirety) and molecular beacons (See, e.g., Tyagi et al. 1996 Nature Biotech, 14, 303 and Int. App. WO 95/13399, herein incorporated by reference), extension based amplification (e.g., amplification refractory mutation systems, amplification refractory mutation system linear extensions (See, e.g., EP 332435, herein incorporated by reference in its entirety), competitive oligonucleotide priming system (See, e.g., Gibbs et al., 1989 Nucleic Acids Research 17, 2347, herein incorporated by reference in its entirety), mini sequencing, restriction fragment length polymorphism, restriction site generating PCR, oligonucleotide ligation assay and many others described herein and elsewhere.

DESCRIPTION OF THE DRAWINGS

FIG. 1 shows the results of Example 1, where two invasive cleavage assays were used to detect different parts of the same viral sequence.

FIG. 6A shows the stem oligonucleotide (SEQ ID NO:6), with its 3' target specific region hybridized to the hypothetical target sequence (SEQ ID NO:7) and its stem region not hybridized to the target sequence. FIG. 6A also shows the upstream oligonucleotide (SEQ ID NO:8), with its 5' target specific region hybridized to the target sequence and its stem specific region hybridized to a portion of the stem region of the stem oligonucleotide. FIG. 6A also show the 3' region of the upstream oligonucleotide as a single base N in this embodiment. A downstream probe is also shown in FIG. 6A with a 3' region hybridized to a portion of the stem region of the stem oligonucleotide and a 5' region not hybridized to the stem region of the stem oligonucleotide. As seen in FIG. 6A, the downstream probe, upstream oligonucleotide and stem region of the stem oligonucleotide combine to form an invasive cleavage structure. FIG. 6A shows a small box around the highlights the area of overlap between the downstream probe and upstream oligonucleotide on the stem region. FIG. 6B shows the result of a cleavage agent recognizing the structure shown in FIG. 6A and cleaving the invasive cleavage structure. As can be seen, the downstream probe is cleaved resulting in a 5' cleaved portion (SEQ ID NO:10) and a remainder portion (SEQ ID NO:11). In certain embodiments, the 5' cleaved portion can be configured to serve as an upstream (INVADER) oligonucleotide with a FRET cassette (e.g. as shown in FIG. 5) in order to generate a detectable signal.

FIG. 7A shows a stem oligonucleotide (SEQ ID NO:12) and an extended upstream oligonucleotide (SEQ ID NO:13) hybridized to a hypothetical target sequence (SEQ ID NO:7). FIG. 7A shows dashed lines to indicate how the 3' end of an upstream oligonucleotide was extended by a polymerase using the stem region of the stem oligonucleotide as a template to generate the extended upstream oligonucleotide. FIG. 7B shows, after that after the extended upstream oligonucleotide is separated from the target sequence and stem oligonucleotide, it can be hybridized to a primer. In FIG. 7B, the primer is hybridized to the upstream oligo extended region (the region generated in FIG. 7A as shown in dashed lines). This primer can prime polymerization using the extended upstream oligonucleotide to generate a stem amplicon sequence as shown in FIG. 7B (shown as the combination of the primer and the extended bases shown in dashed lines). The stem amplicon sequence and extended upstream oligonucleotide can then be separated (e.g., by heating). As shown in FIG. 7C, the stem amplicon can then be detected by an invasive cleavage reaction. The stem amplicon sequence and extended upstream oligonucleotides could also be used as templates for one or more rounds of PCR (not shown in this figure).

DESCRIPTION OF THE INVENTION

Figure 2:
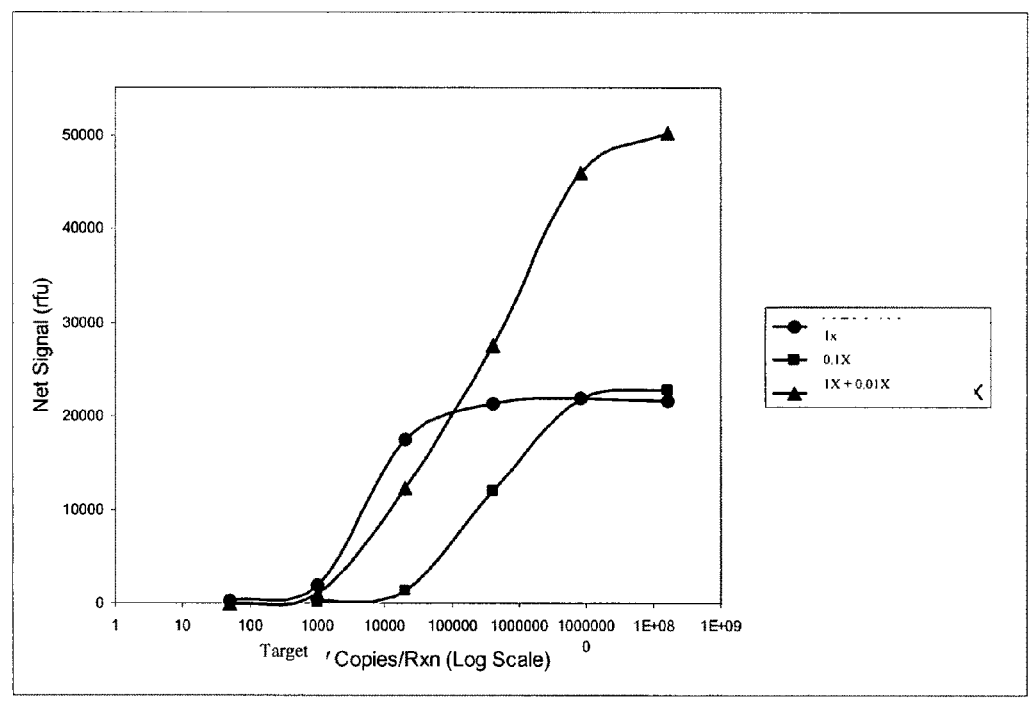
FIG. 2 shows the results of Example 2, where the primary probe was provided at 1× and 0.01×, allowing the assay to detect viral RNA in a linear dynamic range from 50 to 8,000,000 copies.

The present invention provides systems, methods and kits for low-level detection of nucleic acids, detecting at least two different viral sequences in a single reaction vessel, and increasing the dynamic range of detection of a viral target nucleic acid in a sample. The present invention also provides T-structure invasive cleavage assays, as well as T-structure related target dependent non-target amplification methods and compositions. The present invention further relates to methods, compositions, devices and systems for consistent nucleic acid dispensing onto surfaces.

I. Increased Dynamic Range Detection of Viral Target Sequences

In some embodiments, the present invention achieves greater dynamic range of detection through the use of differential levels of amplification of regions of a target nucleic acid, such as a viral target nucleic acid (e.g., no amplification, linear amplification at one or more efficiencies, and/or exponential amplification at one or more efficiencies). In some embodiments, the present invention achieves greater dynamic range of detection through the use of probes with different hybridization properties to one or more analyte-specific regions of a target nucleic acid or target nucleic acids (e.g., viral target nucleic acids). In some embodiments, the present invention achieves greater dynamic range of detection through the use of different signal generation methods. In some embodiments, the present invention achieves greater dynamic range of detection through the use of different signal detection methods. In preferred embodiments, combinations of two or more of the methods are employed. For example, in some preferred embodiments, two or more probes (e.g., three, four, etc.) are contacted with first and second amplicons obtained via different levels of amplification. In some such embodiments, each probe generates the same type of signal so that one simply detects total signal generated by the reactions. The collective signal permits detection of target nucleic acid over a broad dynamic range. For example, experiments conducted during the development of the present invention have demonstrated the ability to detect target nucleic acid from samples differing in over eight logs of copy number of target nucleic acid originally present in the sample.

In certain embodiments, the present invention provides methodologies for expansion of the dynamic range of hybridization assays, such as serial invasive cleavage assays. In some embodiments, the upper limit of dynamic range may be expanded by the use of an additional probe that is present in the reaction at a lower concentration than another probe. In some embodiments, this additional probe will hybridize to the same region of the target. For invasive cleavage reactions, this probe may contain a different arm, or flap, sequence that is released after cleavage. In certain embodiments related to invasive cleavage assays, a second FRET cassette will also be added to the reaction with the appropriate sequence to detect those cleaved flaps from the additional probe. Generally the concentration of the second FRET cassette is about the same as the first FRET cassette. For example, in certain embodiments, if probe B is present in the reaction at 100-fold lower concentration than probe A, this will enable the detection of target nucleic acid when it is present at concentrations above the upper limit of detection of probe A. In this manner, each additional probe, present at 100-fold lower concentrations will enable the detection of two additional orders of magnitude of probe concentration. This methodology is not limited to two primary probes, but may be expanded to three or more. Preferably, the methods are combined with amplification methods where one part of the target is amplified to a different level that a second part of the target.

As mentioned above, in certain embodiments, two probes are employed that are present at different concentrations that detect the same target nucleic acid molecule across a broad range of concentrations. In some embodiments involving invasive cleavage reactions, each of the two primary probes contain the same analyte specific region (ASR) but have different flap regions. Each of these two flap regions, when cleaved, reports to a different FRET cassette or other reporter sequence or system. In some embodiments, the two FRET cassettes both contain the same fluorophore molecule. In this system, an increase in dynamic range is achieved without the use of multiple different fluorophores. This system, therefore, offers a cost advantage over multiple fluorophore systems. Furthermore, expansion of dynamic range with a single fluorophore allows for multiplexing with multiple fluorophores for detection of different targets in the same vessel across a broader dynamic range than was previously feasible.

In certain embodiments, the concentration of each primary probe is present at 100-fold difference relative to each other, and the concentration of the two FRET cassettes are present at equivalent concentrations. In certain embodiments, as an example, the dynamic range with each of the primary probes present individually may be $10^4$-$10^6$ and $10^6$-$10^8$, respectively, while the dynamic range of the assay when both are present at the requisite different concentrations may be $10^4$-$10^8$. The dynamic range of the serial invasive cleavage assay may be further expanded by the use of further additional primary probes, each present at different concentrations. In this manner, three, four, five or more primary probes, each having the same ASR and different flaps may report to the same number of different FRET cassettes, each reporting the same color or detection format. Such a combination of primary probes enables the expansion of the dynamic range to cover 5, 6, 7, 8, 9, 10, 11, 12, 13, 14 or 15 orders of magnitude.

The methods of the present invention are not limited by the type of target nucleic acid. For example, the target nucleic acid may include, for example, nucleic acid material prepared from viruses having an RNA genome. Typically, the RNA target sequence will be converted to a cDNA molecule through the action of a reverse transcriptase, and then detected by the nucleic acid detection assay. Incorporation of the methods of the present invention will increase the dynamic range of detection of RNA target sequences to a breadth not previously feasible.

The methods of the present invention may be combined with amplification methods (e.g., PCR) to extend the lower limit of detection down to the theoretical limit of amplification, on the order of 1 copy per reaction vessel. Using this approach, the dynamic range of nucleic acid detection assay may be, for example, from 1 to $10^7$ copies using a single set of reaction conditions and probe combinations in each reaction vessel being compared.

Additionally, methods of the present invention involve differential pre-amplification of target species prior to the detection assay. In certain embodiments, the use of differential semi-nested PCR using primers of different melting temperatures will result in a mixed population of different species, each containing the target region detected by the detection assay. The species present in higher numbers in the sample after this step can be detected by the probes present at lower concentration within its dynamic range, and the species present in lower numbers in the sample can be detected by the primary probe present at higher concentration within its dynamic range, as explained above. In addition, a population of target molecules present at different concentrations can also be generated by simultaneously combining linear and exponential amplification (or other types of amplification that lead to different levels of amplification). For example, two target-derived amplicons, both containing the target region detected by the nucleic acid detection assay, would be generated by producing one with a single PCR primer (for linear amplification) and the other with two PCR primers (for exponential amplification). As above, the different concentrations of targets can be detected with multiple primary probes tailored to detect those concentrations within their dynamic range. Further, non-amplified and amplified DNA can also be simultaneously detected using the above-described combination of probes.

Differential pre-amplification may also comprise multiple similar amplifications (e.g., exponential amplifications) that are performed at different efficiencies so as to allow expanded dynamic range. By way of example and not to be limited to any particular embodiment or mechanism, target sequences may be selected such that one region to be amplified comprises few of a selected nucleotide, while another region to be amplified comprises an abundance of the same nucleotide. Pre-amplification under conditions wherein the dNTP required to replicated the selected nucleotide is limited or omitted will favor amplification of the sequence that is largely free of the limiting nucleotide. Conditions can be selected to allow the other sequence to amplify inefficiently, e.g., by mis-incorporating bases. This is but one way in which differential pre-amplification can be configured to allow.

In some embodiments, additional probes are used to further expand the dynamic range (e.g., three probes of different concentrations that each bind to the same analyte-specific region). In some embodiments, the method detects one or more probes under each of three distinct amplification conditions: e.g., one probe or probe set that detects exponentially amplified target nucleic acid; one probe or probe set that detects linearly amplified target nucleic acid; and one probe or probe set that detects unamplified target nucleic acid. Additional amplification conditions may also be used (e.g., exponential amplification using primers or other reaction conditions that provide different amplification efficiency per cycle—e.g., a first set that is 90% efficient per cycle and a second set that is 70% efficient per cycle).

Where PCR or other amplification techniques are used, it may be desirable to use buffers and other agents and reaction conditions that minimize limitations of the respective amplification techniques. For example, where PCR is used, in some embodiments, a short amplicon is used. In some embodiments, the amplicon is less than one kilobase in length, although the present invention is not limited to such amplicons. In some embodiments, where the target nucleic is RNA, the amplicon is less than 100 bases, although the present invention is not so limited.

Accordingly, in some embodiments, the present invention provides methods and compositions for performing probe hybridization assays. In some embodiments, the method utilizes a primary or first probe and preferably at least one additional probe having different hybridization characteristics with respect to a target sequence than the primary probe. In some embodiments, a single probe that provides enhanced dynamic range is utilized. In preferred embodiments, the compositions and methods of the present invention utilize a combination of two or more probe oligonucleotides to increase the dynamic range of detection of the amount of a target nucleic acid present in a sample. In preferred embodiments, combinations of two or more probe oligonucleotides include a mixture of probe oligonucleotides with varying degrees of hybridization to a target nucleic acid (e.g., frequency of occupation of a hybridization site). Exemplary probe oligonucleotides of the present invention are described in greater detail below.

In some embodiments, three or more probes are used (e.g., four, five, six, etc.). Two or more of the probes may be configured to hybridize to the same region of the target nucleic acid. However, one or more of the probes may be configured to hybridize to a second region of the target nucleic acid or to a different target nucleic acid. In some embodiments, the pluralities of different probes are configured to generate a detectable signal directly or indirectly. In some embodiments, the different probes use the same type of label so that the detected signal is an additive accumulation of the signal from the first and second probes. In some such embodiments, the user of the method observes the signal throughout the broader dynamic range without knowing or needing to know the contribution provided by each type or probe.

Using such systems and methods, detection of a target nucleic acid can be achieved through a very extensive dynamic range. In some embodiments, this permits detection of target nucleic acids without the need to amplify the target nucleic acid or without the need to extensively amplify the target nucleic acid. However, the systems and methods may further be employed with amplification methods, where desired. As described herein, the systems and methods of the present invention have been exemplified with a combination of polymerase chain extension amplification and invasive cleavage-based detection. Such methods experimentally demonstrated successful detection of target nucleic acids having over an eight-log difference in starting concentration. Thus, the systems and methods of the present invention are exceptionally well suited to the detection of target nucleic acids whose concentration differs dramatically from sample to sample. For example, patients infected with viruses such as HCV and HIV differ greatly the copy number of virus target nucleic acid present in sample (e.g., blood) from very low copy (as few as one copy) to very high copy (millions to billions of copies or more). The ability of a single detection system to simultaneously detect viral target nucleic acid throughout this range is greatly desired. The present invention provides systems and methods that find use for such detection.

The compositions and methods are useful for the detection and quantitation of a wide variety of nucleic acid targets. The compositions and methods of the present invention are particularly useful for the quantitation of viral target nucleic acids (e.g., viral pathogens). Exemplary viral nucleic acids for which a clinical or research need for the detection of a large range of viral concentrations (e.g., viral load) include, but are not limited to, human immunodeficiency virus (HIV) and other retroviruses, hepatitis C virus (HCV), hepatitis B virus (HBV), hepatitis A virus (HAV), human cytomegalovirus, (CMV), Epstein bar virus (EBV), human papilloma virus (HPV), herpes simplex virus (HSV), Varicella Zoster Virus (VZV), bacteriophages (e.g., phage lambda), adenoviruses, and lentiviruses. In other embodiments, the compositions and methods of the present invention find use in the detection of bacteria (e.g., pathogens or bacteria important in commercial and research applications). Examples include, but are not limited to, *Chlamydia* sp., *N. gonorrhea*, and group B *streptococcus*.

In some embodiments, the target sequence is a synthetic sequence. For example, a fragment generated in an enzymatic reaction (e.g., a restriction fragment, a cleaved flap from an invasive cleavage reaction, etc.) can be considered a target sequence. In some such embodiments, the detection of such a molecule indirectly detects a separate target nucleic acid from which the synthetic sequence was generated. For example, in an invasive cleavage reaction, a cleaved flap from a primary reaction may be detected with first and second probes that are FRET cassettes. The FRET cassettes differ in some characteristic (e.g., length, etc.) such that the cleaved flap differentially hybridizes to the first and second probes. By using both FRET cassettes (or a third, fourth, etc.), the dynamic range of the reaction is improved.

The quantitation of target nucleic acids using the methods and compositions of the present invention are utilized in a variety of clinical and research applications. For example, in some embodiments, the detection assays with increased dynamic range of the present invention are utilized in the detection and quantitation of viral pathogens in human samples. The detection assays of the present invention are suitable for use with a variety of purified and unpurified samples including, but not limited to, urine, stool, lymph, whole blood, and serum. In preferred embodiments, the detection assays of the present invention are suitable for use in the presence of host cells.

In other embodiments, the detection assays of the present invention find use in research applications including, but not limited to, drug screening (e.g., for drugs against viral pathogens), animal models of disease, and in vitro quantitation of target nucleic acid (e.g., bacterial, viral, or genomic nucleic acids).

The probe oligonucleotides of the present invention find use in a variety of nucleic acid detection assays including, but not limited to, those described below. It should be understood that any nucleic acid detection method that employs hybridization can benefit from the systems and methods of the present invention.

A. Probe Oligonucleotides

In some embodiments, the present invention provides methods for altering (e.g., increasing) the dynamic range of a nucleic acid detection assay by altering probe oligonucleotides. In some embodiments, the present invention provides combinations of two or more probe oligonucleotides for use in the same detection assay. The present invention is not limited by the manner in which probes are modified to alter hybridization characteristics. Certain exemplary embodiments are provided below.

i. Mismatch Probes

In some embodiments, the present invention provides probes with one or more (preferably one) mismatch with the target sequence. The present invention is not limited to a particular mechanism. Indeed, an understanding of the mechanism is not necessary to practice the present invention. Nonetheless, it is contemplated that the presence of one or more mismatches allows the probe to bind to the target, but with a reduced affinity as compared to a corresponding probe lacking mismatches. This decreases the percent of the time that the mismatch probe occupies the target site, thus decreasing the signal generated (or increasing the signal, depending on the detection system used). The decrease in signal allows the detection assay to remain linear or accurate for quantitation at a higher target concentration.

In some embodiments, mismatch probes are utilized in combination with completely complementary probes. The completely complementary probes occupy the target-binding site a higher percentage of the time than the mismatch probes and thus generate more signal. The higher signal allows for the detection of lower concentrations of target nucleic acid. The use of both probes increases the dynamic range of the detection assay. In particular, as described above, it increases the linearity through a broader concentration of target molecules.

Example 1 and FIGS. 1 and 2 demonstrate how the use of mismatch probes can increase the dynamic range of an assay. A combination of match and mismatch probes was used in an INVADER assay to detect target nucleic acids. The mismatch probe increased the dynamic range by up to 16-fold over the use of a single completely complementary probe.

ii. Lower Probe Concentrations

In other embodiments, the present invention provides a combination of probe concentrations to increase the dynamic range of a detection assay. In some embodiments a combination of two or more probe oligonucleotides, each of which is at a different concentration, is utilized. The probes present at a lower concentration generate a lower signal and are thus suitable for detecting higher target concentrations. The probes present at a higher concentration generate a higher signal and are thus suitable for detecting a lower concentration of target nucleic acids. By utilizing two or more probes at a range of concentrations, a broader dynamic range of target concentrations can be detected.

When probes are attached to a solid surface, lower probe concentration can be achieved, in some embodiments, through the use of different densities of probes attached to particular detection zones on the solid surface. For example, a first probe detection zone has a first density of the probe and a second probe detection zone has a lower density of the probe. Detection at the two detection zones provides enhanced dynamic range. In some embodiments, both detection zones generate the same type of signal and the total signal from the solid surface is detected (e.g., in real-time) to detect the target nucleic acid through an expanded dynamic range.

Example 1 and FIGS. 1 and 2 demonstrate how the use of multiple probes present at different concentrations probes can increase the dynamic range of an assay. A combination of concentrations of probes was used in an INVADER assay to detect target nucleic acids. The use of multiple concentrations of probes increased the dynamic range of the assay over the use of a single probe.

iii. Charge Modified Probes

In other embodiments, the present invention utilizes charge modified probes to alter binding efficiency of probes (See e.g., U.S. Pat. No. 6,780,982, herein incorporated by reference in its entirety for all reasons). In some embodiments, the charge modified probes comprise "charge tags." Positively charged moieties need not always carry a positive charge. As used herein, the term "positively charged moiety" refers to a chemical structure that possesses a net positive charge under the reaction conditions of its intended use (e.g., when attached to a molecule of interest under the pH of the desired reaction conditions). Indeed, in some preferred embodiments of the present invention, the positively charged moiety does not carry a positive charge until it is introduced to the appropriate reaction conditions. This can also be thought of as "pH-dependent" and "pH-independent" positive charges. pH-dependent charges are those that possess the charge only under certain pH conditions, while pH-independent charges are those that possess a charge regardless of the pH conditions.

The positively charged moieties, or "charge tags," when attached to another entity, can be represented by the formula:

$$X—Y$$

where X is the entity (e.g., a solid support, a nucleic acid molecule, etc.) and Y is the charge tag. The charge tags can be attached to other entities through any suitable means (e.g., covalent bonds, ionic interactions, etc.) either directly or through an intermediate (e.g., through a linking group). In preferred embodiments, where X is a nucleic acid molecule, the charge tag is attached to either the 3' or 5' end of the nucleic acid molecule.

The charge tags may contain a variety of components. For example, the charge tag Y can be represented by the formula:

$$Y_1—Y_2$$

where $Y_1$ comprises a chemical component that provides the positive charge to the charge tag and where $Y_2$ is another desired component. $Y_2$ may be, for example, a dye, another chemical component that provides a positive charge to the charge tag, a functional group for attachment of other molecules to the charge tag, a nucleotide, etc. Where such a structure is attached to another entity, X, either $Y_1$ or $Y_2$ may be attached to X.

$$X—Y_1—Y_2 \text{ or } X—Y_2—Y_1$$

The charge tags are not limited to two components. Charge tags may comprise any number of desired components. For example, the charge tag can be represented by the formula:

$$Y_1—Y_2—Y_3—Y_n \text{ (n=any positive integer).}$$

where any of the $Y_x$ groups comprises a chemical component that provides the positive charge to the charge tag and where the other Y groups are any other desired components. For example, in some embodiments, the present invention provides compositions of the structure:

$$X—Y_1—Y_2—Y_3—Y_4$$

where X is an entity attached to the charge tag (e.g., a solid support, a nucleic acid molecule, etc.) and where $Y_1$ is a dye, $Y_2$ is a chemical component that provides the positive charge to the charge, $Y_3$ is a component containing a functional group that allows the attachment of other molecules, and $Y_4$ is a second chemical component that provides a positive charge. The identity of each of $Y_1$-$Y_4$ can be interchanged (i.e., the present invention is not limited by the order of the components).

The present invention is not limited by the nature of the chemical components that provides the positive charge to the charge tag. Such chemical components include, but are not limited to, amines (primary, secondary, and tertiary amines), ammoniums, and phosphoniums. The chemical components may also comprise chemical complexes that entrap or are otherwise associated with one or more positively charged metal ions.

In preferred embodiments of the present invention, charge tags are attached to nucleic acid molecules (e.g., DNA molecules). The charge tags may be synthesized directly onto a nucleic molecule or may be synthesized, for example, on a solid support or in liquid phase and then attached to a nucleic acid molecule or any other desired molecule. In some preferred embodiments of the present invention, charge tags that are attached to nucleic acid molecules comprise one or more components synthesized by H-phosphonate chemistry, by incorporation of novel phosphoramidites, or a combination of both. For example, compositions of the present invention include structures such as:

$$[X]—[Y_1—Y_2—Y_3—Y_4]$$

where [X] is a nucleic acid molecule and [Y . . . ] is a charge tag. In some embodiments, $Y_1$ is a dye, $Y_2$ is synthesized using H-phosphonate chemistry and comprises a chemical component that provides a positive charge to the charge tag, $Y_3$ is a positively charged phosphoramidite, and $Y_4$ is a nucleotide or polynucleotide. Any of the Y components are interchangeable with one another.

As discussed above, one or more components of a charge tag can be synthesized using H-phosphonate chemistry. Production of charge tag using the methods described herein provides a convenient and flexible modular approach for the design of a wide variety of charge tags. Since its introduction, solid phase H-phosphonate chemistry (B. C. Froehler, Methods in Molecular Biology, 20:33, S. Agrawal, Ed. Humana Press; Totowa, N.J. [1993]) has been recognized as an efficient tool in the chemical synthesis of natural, modified and labeled oligonucleotides and DNA probes. Those skilled in the art know that this approach allows for the synthesis of the oligonucleotide fragments with a fully modified phosphodiester backbone (e.g., oligonucleotide phosphorothioates; Froechler [1993], supra) or the synthesis of oligonucleotide fragments in which only specific positions of the phosphodiester backbone are modified (Agrawal, et al., Proc. Natl. Acad. Sci USA, 85:7079 [1988], Froehler, Tetrahedron Lett. 27:5575 [1986], Froehler, et al., Nucl. Acids Res. 16:4831 [1988]). The use of H-phosphonate chemistry allows for the introduction of different types of modifications into the oligonucleotide molecule (Agrawal, et al., Froehler[1986], supra, Letsinger, et al., J. Am. Chem. Soc., 110:4470 [1988], Agrawal and Zamecnik, Nucl. Acid Res. 18:5419 [1990], Handong, et al., Bioconjugate Chem. 8:49 [1997], Vinogradov, et al., Bioconjugate Chem. 7:3 [1995], Schultz, et al., Tetrahedron Lett. 36:8407 [1995]), however the replacement of the phosphodiester linkage by the phosphoramidate linkage is one of the most frequent changes due to its effectiveness and synthetic flexibility. Froehler and Letsinger were among first to use this approach in the synthesis of modified oligonucleotides in which phosphodiester linkages were fully or partially replaced by the phosphoramidate linkages bearing positively charged groups (e.g., tertiary amino groups; Froehler [1986], Froehler, et al., [1988], and Letsinger, et al., supra).

In some embodiments of the present invention, charge tags are generated using H-phosphonate chemistry. The charge tags may be assembled on the end of a nucleic acid molecule or may be synthesized separately and attached to a nucleic acid molecule. Any suitable phosphorylating agent may be used in the synthesis of the charge tag. For example, the component to be added may contain the structure:

A-B—P where A is a protecting group, B is any desired functional group (e.g., a functional group that provides a positive charge to the charge tag), and P is a chemical group containing phosphorous. In preferred embodiments, B comprises a chemical group that is capable of providing a positive charge to the charge tag. However, in some embodiments B is a functional group that allows post-synthetic attachment of a positively charged group to the charge tag.

In other embodiments, positively charged phosphoramidites (PCP) and neutral phosphoramidites (NP) are utilized to introduce both positive charge and structure modulation into the synthesized charge-balanced CRE probe (See e.g., U.S. Pat. No. 6,780,982, herein incorporated by reference in its entirety).

Standard coupling protocol with the use of the phosphoramidite reagents (which are compatible with the chemical synthesis of oligonucleotides) is associated with the introduction, into the growing molecule, of one negative charge per each performed coupling step, due to the formation of the phosphodiester linkage.

iv. Nucleic Acid Modification Agents

The present invention is not limited to the use of charge tags as modifiers of probe hybridization efficiency. Any internal (e.g., to the probe) or external agent that alters the hybridization strength of probe binding is suitable for use with the methods and compositions of the present invention.

In some embodiments, the present invention provides probes comprising intercalating agents. Intercalating agents are agents that are capable of inserting themselves between the successive bases in DNA. In some embodiments, intercalating agents alter the binding properties of nucleic acid probes.

Examples of intercalating agents are known in the art and include, but art limited to, ethidium bromide, psoralen and derivatives, acridines, proflavine, acridine orange, acriflavine, fluorcoumanin, ellipticine, daunomycin, chloroquine, distamycin D, chromomycin, homidium, mithramycin, ruthenium polypyridyls, and anthramycin.

In other embodiments, minor groove DNA binding agents are utilized to modify (e.g., increase or decrease) the hybridization efficiency of probes. Examples of minor groove binding agents include, but are not limited to, duocarmycins (See e.g., Boger, Pure & Appl. Chem., Vol. 66, No. 4, pp. 837-844, herein incorporated by reference in its entirety), netropsin, bisbenzimidazole, aromatic diamidines, lexitropsins, distamycin, and organic dications, based on unfused-aromatic systems (See e.g., U.S. Pat. No. 6,613,787, herein incorporated by reference in its entirety).

In still further embodiments, modified bases are utilized to alter the hybridization efficiency of probes. For example, in some embodiments, modified bases that include charged groups are utilized. Examples include, but are not limited to, the substitution of a "t" nucleotide with "amino-T" in a probe and other modified nucleotides.

In yet other embodiments, one or more probe nucleotides are modified by the covalent attachment of groups that alter the hybridization properties of the probe. Examples include, but are not limited to, the attachment of amino acids to nucleotides.

In yet other embodiments, probe oligonucleotides with base analogues are utilized to alter the hybridization characteristics of probes. For example, in some embodiments, nucleotides that do not form hydrogen bonds but that still participate in base stacking are utilized. Examples include but are not limited to non-polar, aromatic nucleoside analogs such as 2,4-difluorotoluene and "universal" bases such as 5-nitroindole and 3-nitropyrrole. In other embodiments, base analogs that retain hydrogen bonding ability are utilized (See e.g., US Patent application US20040106108A1 and WO 04/065550A3, each of which is herein incorporated by reference in its entirety for all purposes).

v. Probe Length

In yet other embodiments, probe length is altered in order to alter the hybridization characteristics of a probe. For example, in some embodiments, two or more probes that hybridize to the same target sequence and share the same sequence are utilized. In some embodiments, one of the probes is shorter by one, two, three, or four or more bases. It is preferred that the probes be truncated from one or both ends. Thus, the probes share sequence in all regions except the truncated 3' or 5' ends. It is contemplated that the shorter probes will anneal with decreased hybridization efficiency and will thus be useful in the detection of higher copy numbers of target sequences than the full length probe. In preferred embodiments, a combination of full length and truncated probes is utilized to give the maximum range of target concentration detection. In some embodiments, the same length is employed, but the probe is split into two or more portions connected by linkers. Such probes hybridize with different affinity depending on a variety of factors, including secondary structure of the target nucleic acid in regions in which the probes or probe fragments hybridize.

vi. Secondary Structure

In some embodiments, probes that comprise secondary structure are utilized to alter the hybridization efficiency of the probe. For example, in some embodiments, two or more probes are designed to hybridize the same target sequence. One of the probes is designed to have minimal secondary structure. Additional probes are designed that retain target sequence recognition, but that have secondary structure. It is contemplated that the probes with secondary structure will exhibit decreased hybridization properties and will thus be suitable for the detection of large copy numbers of target sequence. The combination of probes lacking and containing secondary structure serves to detect a larger dynamic range of target nucleic acids than a single probe. Likewise, probes that hybridize to regions of the target nucleic acid that differ in secondary structure may be used. For example, a probe that has 18 of 18 bases that bind to linear target nucleic acid will hybridize differently than a similar probe shifted two bases over on target nucleic acid such that the two bases on the end of the probe correspond to a region of the target nucleic acid occupied in an internal hairpin structure or other secondary structure.

vii. Competitor Oligonucleotides

In yet other embodiments, additional oligonucleotides are utilized to modify hybridization efficiency of probes. For example, in some embodiments, two probes that recognize the same target sequence are designed. One of the probes further comprises additional nucleic acid sequence (e.g., at the 3' or 5' end) that does not hybridize to the target sequence. Competitor oligonucleotides are designed to hybridize to the extra region. The binding of the competitor oligonucleotide decreases the hybridization efficiency of the probe to the target. The combination of probes with and without competitor binding sequences serves to detect a larger dynamic range of target nucleic acids than a single probe.

viii. Reaction Conditions

In still further embodiments, reaction conditions are modified to alter probe hybridization characteristics. For example, in some embodiments, identical probes are utilized in separate reaction vessels, chamber, or wells. One reaction vessel utilizes "standard" reaction conditions for the detection assay (e.g., those supplied by the manufacturer or known in the art). The other reaction vessel comprises altered reaction conditions that increase or decrease the hybridization efficiency of the probe. Examples of parameters that affect nucleic acid hybridization conditions include, but are not limited to, ionic strength, buffer composition, pH, and additives (e.g., glycerol, polyethylene glycol, proteins).

ix. Stacking Oligonucleotides

In still further embodiments, adjacently hybridizing oligonucleotides are used to alter probe hybridization characteristics. When short strands of nucleic acid align contiguously along a longer strand, the hybridization of each is stabilized by the hybridization of the neighboring fragments because the base pairs can stack along the helix as though the backbone was, in fact, uninterrupted. This cooperativity of binding can give each segment a stability of interaction in excess of what would be expected for the segment hybridizing to the longer nucleic acid alone. In the event of a perturbation in the cooperative binding, e.g., by a mismatch at or near the junction between the contiguous duplexes, this cooperativity can be reduced or eliminated. In some embodiments of the present invention, probes are configured to cooperate in distinct ways with one or more adjacently hybridizing oligonucleotides, so as to provide probes having different hybridization characteristics. In some embodiments, a probe comprises one or more mismatched bases at near the junction with the adjacent oligonucleotide, so as to alter or disrupt cooperativity of binding, as compared to a probe lacking the mismatches. In other embodiments, a probe comprises one or more base analogs selected to reduce stacking interactions with adjacent bases. In yet other embodiments, it is envisioned that gaps of one or more nucleotides (e.g., by the use of truncated probes) are used to alter cooperativity and thus alter hybridization characteristics. The use of a combination of probes that have a range of cooperativities of binding with an adjacently hybridized oligonucleotide, and thus having a range of different hybridization stabilities on the target, serves to detect a larger dynamic range of target nucleic acids than a single probe.

x. Multiplex Assays

In some embodiments utilizing multiple nucleic acid probes, the probes are utilized in a biplex or multiplex assay in which a plurality of probes is included in the same reaction vessel. In some embodiments, each probe in a biplex assay comprises a differently detectable label. For example, some embodiments, each probe in a set comprises a different fluorescent label that fluoresces at a different wavelength. Many known probe binding assays are suitable for use in a multiplex format. Methods for performing multiplex assays that are unique to the particular assay format are described below.

xi. Others

Any other method for altering the hybridization of characteristics of a probe may be used with the present invention. Other examples include, but are not limited to: use of sequences in probes or targets that render the sequence susceptible to differential hybridization behavior in response to buffer conditions (e.g., the use of guanosine-quartets) or protein/nucleic acid interactions (e.g., by creating binding sites for nucleic acid binding proteins or enzyme that bind or alter nucleic acid sequences); use of dangling ends (e.g., for dangling-end stabilization and stacking); attachment of iron or other magnetic agents to allow concentration of the nucleic acid in a magnetic field; use of agents that titrate out a specific probe; and the like.

One may also use different labeling techniques to achieve a differential detection of signal, independent of the hybridization properties of the probe. For example, the location of labels and quenchers in a FRET detection system may be altered between first and second probes to alter the amount of signal detected from the probes. FRET signaling can also be affected by many other parameters, including, but not limited to, the use of additional chemical moieties that influence the amount of quenching and the use of secondary structure in the probes. Additional methods for altering signal detection include the use of a helper oligonucleotide that is provided at low concentration, that when bound to a target occupied by a probe of the invention, changes the wavelength or otherwise alters the detectable aspects of the probe. The concentration of the helper can be configured to only allow detection the alteration when a particular threshold level of probe is hybridized to target. Any method or system that permits differential detection of hybridization events may be used in the systems and methods of the present invention.

B. Detection Assays

The present invention is not limited to a particular detection assay. Any number of suitable detection assays may be utilized. In some embodiments, the present invention provides methods and compositions for the detection of DNA or RNA (e.g., viral RNA). In some embodiments, the detection assays described below are suitable for direct detection of RNA. In other embodiments, RNA is reverse transcribed (e.g., using a reverse transcriptase enzyme such as AMV or MMLV) into DNA and the detection assay is performed on the corresponding DNA. Methods for reverse transcription are known in the art. In some embodiments, a single enzyme having both reverse transcriptase and polymerase activities is used.

Exemplary assays that find use with the methods of the present invention are described below.

i. Invasive Cleavage Assays

In some embodiments, the methods and compositions of the present invention are used to increase the dynamic range of invasive cleavage assays, such as the INVADER assay. The INVADER assay provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies, Madison, Wis.) and are described in U.S. Pat. Nos. 5,846,717, 5,985,557, 5,994,069, 6,001,567, and 6,090,543, WO 97/27214, WO 98/42873, Lyamichev et al., Nat. Biotech., 17:292 (1999), Hall et al., PNAS, USA, 97:8272 (2000), each of which is herein incorporated by reference in their entirety for all purposes.

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 6,090,543; 5,994,069; Lyamichev et al., Nat. Biotech., 17:292 (1999), Hall et al., PNAS, USA, 97:8272 (2000), WO97/27214 and WO98/42873, each of which is herein incorporated by reference in their entirety for all purposes).

The INVADER assay detects specific DNA and RNA sequences by using structure-specific enzymes (e.g. FEN endonucleases) to cleave a complex formed by the hybridization of overlapping oligonucleotide probes. Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescent that is quenched by an internal dye. Upon cleavage, the de-quenched fluorescent labeled product may be detected using a standard fluorescence plate reader.

The INVADER assay detects specific target sequences in unamplified, as well as amplified, RNA and DNA including genomic DNA. In the embodiments shown schematically in FIG. 5, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations or target sequences. In the primary reaction (FIG. 5, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 5), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the MT primary probe and the WT target, FIG. 5, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA or RNA being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In certain embodiments, the target nucleic acid sequence is amplified prior to detection (e.g. such that synthetic nucleic acid is generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. Nos. 6,117,634, issued Sep. 12, 2000, and 6,197,557, issued Mar. 6, 2001, and in PCT application WO 98/39485, each incorporated by reference herein in their entireties for all purposes.

In some embodiments, synthetic DNA suitable for use with the methods and compositions of the present invention is made using a purified polymerase on multiply-primed genomic or other DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive (d 29 polymerase (as described, e.g., in U.S. Pat. Nos. 5,198,543 and 5,001,050, each herein incorporated by reference in their entireties for all purposes) in combination with exonuclease-resistant random primers, such as hexamers.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (Reynaldo et al., J. Mol. Biol. 97: 511-520 (2000)), multiple probes can hybridize to the same target, allowing multiple cleavages, and the generation of multiple cleavage products.

As described above, in some embodiments, the present invention provides methods of utilizing the INVADER assay to quantitate the amount of target nucleic present in a sample. In some embodiments, the dynamic range of INVADER assays is increased using mismatch probes, alone or in combination with completely homologous probes. It is preferred that the mismatch is not present at the site of cleavage by the cleavage enzyme. In other embodiments, dynamic range of the INVADER assay is increased by using probes of multiple concentrations. In preferred embodiments, each probe in a multiple probe INVADER assay comprises a different label, allowing the reactions to be run in the same well or tube of the reaction vessel and detected simultaneously. However, the probes may also share the same label, permitting the combined signal to be interpreted as one detection event. In some preferred embodiments, a real time assay, in which signal is measured continuously or at time intervals, is utilized. In other embodiments, a single end-point detection is taken at a desired time point. In yet other embodiment, two or more time point readings are taken.

In other embodiments, composite or split probe oligonucleotides are utilized to increase the dynamic range is utilized in the INVADER-directed cleavage assay. For example, the probe oligonucleotide may be split into two oligonucleotides that anneal in a contiguous and adjacent manner along a target oligonucleotide. The probe oligonucleotide is assembled from two smaller pieces: a short segment of 6-10 nts (termed the "miniprobe"), that is to be cleaved in the course of the detection reaction, and an oligonucleotide that hybridizes immediately downstream of the miniprobe (termed the "stacker"), that serves to stabilize the hybridization of the probe. To form the cleavage structure, an upstream oligonucleotide (the INVADER oligonucleotide) is provided to direct the cleavage activity to the desired region of the miniprobe. Assembly of the probe from non-linked pieces of nucleic acid (i.e., the miniprobe and the stacker) allows regions of sequences to be changed without requiring the re-synthesis of the entire proven sequence, thus improving the cost and flexibility of the detection system. In addition, the use of unlinked composite oligonucleotides makes the system more stringent in its requirement of perfectly matched hybridization to achieve signal generation, allowing this to be used as a sensitive means of detecting mutations or changes in the target nucleic acid sequences. In some embodiments, two probe/stacker designs are utilized to increase the dynamic range of the assay. A first configuration, without a gap between the probe and the stacker is utilized. This configuration occupies the target site at a high frequency and serves to generate a higher signal (e.g., in the presence of a low concentration of target). A second configuration, in which a single nucleotide gap between the probe and stacker oligonucleotide is introduced, it utilized for the detection of high concentrations of target. The gapped configuration probe and stacker oligonucleotides hybridize at a lower strength and thus occupy the target site at a lower frequency. This generates a lower signal, which is useful in the detection of high amounts of target sequences.

Additional considerations for performing the INVADER assay are discussed in more detail below.

Oligonucleotide Design for the INVADER Assay

In some embodiments where an oligonucleotide is designed for use in the INVADER assay to detect a target nucleic acid, the sequence(s) of interest are entered into the INVADERCREATOR program (Third Wave Technologies, Madison, Wis.). Sequences may be input for analysis from any number of sources, either directly into the computer hosting the INVADERCREATOR program, or via a remote computer linked through a communication network (e.g., a LAN, Intranet or Internet network). The program designs probes for both the sense and antisense strand. Strand selection is generally based upon the ease of synthesis, minimization of secondary structure formation, and manufacturability. In some embodiments, the user chooses the strand for sequences to be designed for. In other embodiments, the software automatically selects the strand. By incorporating thermodynamic parameters for optimum probe cycling and signal generation (Allawi and SantaLucia, Biochemistry, 36:10581 [1997]), oligonucleotide probes may be designed to operate at a pre-selected assay temperature (e.g., 63° C.). Based on these criteria, a final probe set (e.g., match and mismatch probes and an INVADER oligonucleotide) is selected.

In some embodiments, the INVADERCREATOR system is a web-based program with secure site access that contains a link to BLAST (available at the National Center for Biotechnology Information, National Library of Medicine, National Institutes of Health website) and that can be linked to RNAstructure (Mathews et al., RNA 5:1458 [1999]), a software program that incorporates mfold (Zuker, Science, 244:48 [1989]). RNAstructure tests the proposed oligonucleotide designs generated by INVADERCREATOR for potential uni- and bimolecular complex formation. INVADERCREATOR is open database connectivity (ODBC)-compliant and uses the Oracle database for export/integration. The INVADERCREATOR system was configured with Oracle to work well with UNIX systems, as most genome centers are UNIX-based.

In some embodiments, the INVADERCREATOR analysis is provided on a separate server (e.g., a Sun server) so it can handle analysis of large batch jobs. For example, a customer can submit up to 2,000 SNP sequences in one email. The server passes the batch of sequences on to the INVADERCREATOR software, and, when initiated, the program designs detection assay oligonucleotide sets. In some embodiments, probe set designs are returned to the user within 24 hours of receipt of the sequences.

Each INVADER reaction includes at least two target sequence-specific, unlabeled oligonucleotides for the primary reaction: an upstream INVADER oligonucleotide and a downstream Probe oligonucleotide. The INVADER oligonucleotide is generally designed to bind stably at the reaction temperature, while the probe is designed to freely associate and disassociate with the target strand, with cleavage occurring only when an uncut probe hybridizes adjacent to an overlapping INVADER oligonucleotide. In some embodiments, the probe includes a 5' flap or "arm" that is not complementary to the target, and this flap is released from the probe when cleavage occurs. In some embodiments, the released flap participates as an INVADER oligonucleotide in a secondary reaction.

The following discussion provides one example of how a user interface for an INVADERCREATOR program may be configured.

The user opens a work screen, e.g., by clicking on an icon on a desktop display of a computer (e.g., a Windows desktop). The user enters information related to the target sequence for which an assay is to be designed. In some embodiments, the user enters a target sequence. In other embodiments, the user enters a code or number that causes retrieval of a sequence from a database. In still other embodiments, additional information may be provided, such as the user's name, an identifying number associated with a target sequence, and/or an order number. In preferred embodiments, the user indicates (e.g. via a check box or drop down menu) that the target nucleic acid is DNA or RNA. In other preferred embodiments, the user indicates the species from which the nucleic acid is derived. In particularly preferred embodiments, the user indicates whether the design is for monoplex (i.e., one target sequence or allele per reaction) or multiplex (i.e., multiple target sequences or alleles per reaction) detection. When the requisite choices and entries are complete, the user starts the analysis process. In one embodiment, the user clicks a "Go Design It" button to continue.

In some embodiments, the software validates the field entries before proceeding. In some embodiments, the software verifies that any required fields are completed with the appropriate type of information. In other embodiments, the software verifies that the input sequence meets selected requirements (e.g., minimum or maximum length, DNA or RNA content). If entries in any field are not found to be valid, an error message or dialog box may appear. In preferred embodiments, the error message indicates which field is incomplete and/or incorrect. Once a sequence entry is verified, the software proceeds with the assay design.

In some embodiments, the information supplied in the order entry fields specifies what type of design will be created. In preferred embodiments, the target sequence and multiplex check box specify which type of design to create. Design options include but are not limited to SNP assay, Multiplexed SNP assay (e.g., wherein probe sets for different alleles are to be combined in a single reaction), Multiple SNP assay (e.g., wherein an input sequence has multiple sites of variation for which probe sets are to be designed), and Multiple Probe Arm assays.

In some embodiments, the INVADERCREATOR software is started via a Web Order Entry (WebOE) process (i.e., through an Intra/Internet browser interface) and these parameters are transferred from the WebOE via applet <param> tags, rather than entered through menus or check boxes.

In the case of Multiple SNP Designs, the user chooses two or more designs to work with. In some embodiments, this selection opens a new screen view (e.g., a Multiple SNP Design Selection view). In some embodiments, the software creates designs for each locus in the target sequence, scoring each, and presents them to the user in this screen view. The user can then choose any two designs to work with. In some embodiments, the user chooses a first and second design (e.g., via a menu or buttons) and clicks a "Go Design It" button to continue.

To select a probe sequence that will perform optimally at a pre-selected reaction temperature, the melting temperature ($T_m$) of the SNP to be detected is calculated using the nearest-neighbor model and published parameters for DNA duplex formation (Allawi and SantaLucia, Biochemistry, 36:10581 [1997]). In embodiments wherein the target strand is RNA, parameters appropriate for RNA/DNA heteroduplex formation may be used. Because the assay's salt concentrations are often different than the solution conditions in which the nearest-neighbor parameters were obtained (1M NaCl and no divalent metals), and because the presence and concentration of the enzyme influence optimal reaction temperature, an adjustment should be made to the calculated $T_m$ to determine the optimal temperature at which to perform a reaction. One way of compensating for these factors is to vary the value provided for the salt concentration within the melting temperature calculations. This adjustment is termed a 'salt correction'. As used herein, the term "salt correction" refers to a variation made in the value provided for a salt concentration for the purpose of reflecting the effect on a $T_m$ calculation for a nucleic acid duplex of a non-salt parameter or condition affecting said duplex. Variation of the values provided for the strand concentrations will also affect the outcome of these calculations. By using a value of 0.5 M NaCl (SantaLucia, Proc Natl Acad Sci USA, 95:1460 [1998]) and strand concentrations of about 1 mM of the probe and 1 fM target, the algorithm for used for calculating probe-target melting temperature has been adapted for use in predicting optimal INVADER assay reaction temperature. For a set of 30 probes, the average deviation between optimal assay temperatures calculated by this method and those experimentally determined is about 1.5° C.

The length of the downstream probe to a given target sequence is defined by the temperature selected for running the reaction (e.g., 63° C.). Starting from the position of the variant nucleotide on the target DNA (the target base that is paired to the probe nucleotide 5' of the intended cleavage site), and adding on the 3' end, an iterative procedure is used by which the length of the target-binding region of the probe is increased by one base pair at a time until a calculated optimal reaction temperature ($T_m$ plus salt correction to compensate for enzyme effect) matching the desired reaction temperature is reached. The non-complementary arm of the probe is preferably selected to allow the secondary reaction to cycle at the same reaction temperature. The entire probe oligonucleotide is screened using programs such as mfold (Zuker, Science, 244: 48 [1989]) or Oligo 5.0 (Rychlik and Rhoads, Nucleic Acids Res, 17: 8543 [1989]) for the possible formation of dimer complexes or secondary structures that could interfere with the reaction. The same principles are also followed for INVADER oligonucleotide design. Briefly, starting from the position N on the target DNA, the 3' end of the INVADER oligonucleotide is designed to have a nucleotide not complementary to either allele suspected of being contained in the sample to be tested. The mismatch does not adversely affect cleavage (Lyamichev et al., Nature Biotechnology, 17: 292 [1999]), and it can enhance probe cycling, presumably by minimizing coaxial stabilization effects between the two probes. Additional residues complementary to the target DNA starting from residue N−1 are then added in the 5' direction until the stability of the INVADER oligonucleotide-target hybrid exceeds that of the probe (and therefore the planned assay reaction temperature), generally by 15-20° C.

It is one aspect of the assay design that the all of the probe sequences may be selected to allow the primary and secondary reactions to occur at the same optimal temperature, so that the reaction steps can run simultaneously. In an alternative embodiment, the probes may be designed to operate at different optimal temperatures, so that the reaction steps are not simultaneously at their temperature optima.

In some embodiments, the software provides the user an opportunity to change various aspects of the design including but not limited to: probe, target and INVADER oligonucleotide temperature optima and concentrations; blocking groups; probe arms; dyes, capping groups and other adducts; individual bases of the probes and targets (e.g., adding or deleting bases from the end of targets and/or probes, or changing internal bases in the INVADER and/or probe and/or target oligonucleotides). In some embodiments, changes are made by selection from a menu. In other embodiments, changes are entered into text or dialog boxes. In preferred embodiments, this option opens a new screen (e.g., a Designer Worksheet view).

In some embodiments, the software provides a scoring system to indicate the quality (e.g., the likelihood of performance) of the assay designs. In one embodiment, the scoring system includes a starting score of points (e.g., 100 points) wherein the starting score is indicative of an ideal design, and wherein design features known or suspected to have an adverse affect on assay performance are assigned penalty values. Penalty values may vary depending on assay parameters other than the sequences, including but not limited to the type of assay for which the design is intended (e.g., monoplex, multiplex) and the temperature at which the assay reaction will be performed. The following example provides an illustrative scoring criteria for use with some embodiments of the INVADER assay based on an intelligence defined by experimentation. Examples of design features that may incur score penalties include but are not limited to the following [penalty values are indicated in brackets, first number is for lower temperature assays (e.g., 62-64° C.), second is for higher temperature assays (e.g., 65-66° C.)]:

1. [100:100] 3' end of INVADER oligonucleotide resembles the probe arm:

| ARM SEQUENCE: ENDS IN: | PENALTY AWARDED IF INVADER |
|---|---|
| Arm 1 (SEQ ID NO: 1): CGCGCCGAGG | 5' . . . GAGGX or<br>5' . . . GAGGXX |
| Arm 2 (SEQ ID NO: 2): ATGACGTGGCAGAC | 5' . . . CAGACX or<br>5' . . . CAGACXX |
| Arm 3 (SEQ ID NO: 3): ACGGACGCGGAG | 5' . . . GGAGX or<br>5' . . . GGAGXX |
| Arm 4 (SEQ ID NO: 4): TCCGCGCGTCC | 5' . . . GTCCX or<br>5' . . . GTCCXX |

2. [70:70] a probe has 5-base stretch (i.e., 5 of the same base in a row) containing the polymorphism;
3. [60:60] a probe has 5-base stretch adjacent to the polymorphism;
4. [50:50] a probe has 5-base stretch one base from the polymorphism;
5. [40:40] a probe has 5-base stretch two bases from the polymorphism;
6. [50:50] probe 5-base stretch is of Gs—additional penalty;
7. [100:100] a probe has 6-base stretch anywhere;
8. [90:90] a two or three base sequence repeats at least four times;
9. [100:100] a degenerate base occurs in a probe;
10. [60:90] probe hybridizing region is short (13 bases or less for designs 65-67° C.; 12 bases or less for designs 62-64° C.)
11. [40:90] probe hybridizing region is long (29 bases or more for designs 65-67° C., 28 bases or more for designs 62-64° C.)
12. [5:5] probe hybridizing region length—per base additional penalty
13. [80:80] Ins/Del design with poor discrimination in first 3 bases after probe arm
14. [100:100] calculated INVADER oligonucleotide Tm within 7.5° C. of probe target Tm (designs 65-67° C. with INVADER oligonucleotide less than ≦70.5° C., designs 62-64° C. with INVADER oligonucleotide ≦69.5° C.
15. [20:20] calculated probes Tms differ by more than 2.0° C.
16. [100:100] a probe has calculated Tm 2° C. less than its target Tm
17. [10:10] target of one strand 8 bases longer than that of other strand
18. [30:30] INVADER oligonucleotide has 6-base stretch anywhere—initial penalty
19. [70:70] INVADER oligonucleotide 6-base stretch is of Gs—additional penalty
20. [15:15] probe hybridizing region is 14, 15 or 24-28 bases long (65-67° C.) or 13,14 or 26,27 bases long (62-64° C.)
21. [15:15] a probe has a 4-base stretch of Gs containing the polymorphism In particularly preferred embodiments, temperatures for each of the oligonucleotides in the designs are recomputed and scores are recomputed as changes are made. In some embodiments, score descriptions can be seen by clicking a "descriptions" button. In some embodiments, a BLAST search option is provided. In preferred embodiments, a BLAST search is done by clicking a "BLAST Design" button. In some embodiments, this action brings up a dialog box describing the BLAST process. In preferred embodiments, the BLAST search results are displayed as a highlighted design on a Designer Worksheet.

In some embodiments, a user accepts a design by clicking an "Accept" button. In other embodiments, the program approves a design without user intervention. In preferred embodiments, the program sends the approved design to a next process step (e.g., into production; into a file or database). In some embodiments, the program provides a screen view (e.g., an Output Page), allowing review of the final designs created and allowing notes to be attached to the design. In preferred embodiments, the user can return to the Designer Worksheet (e.g., by clicking a "Go Back" button) or can save the design (e.g., by clicking a "Save It" button) and continue (e.g., to submit the designed oligonucleotides for production).

In some embodiments, the program provides an option to create a screen view of a design optimized for printing (e.g., a text-only view) or other export (e.g., an Output view). In preferred embodiments, the Output view provides a description of the design particularly suitable for printing, or for exporting into another application (e.g., by copying and pasting into another application). In particularly preferred embodiments, the Output view opens in a separate window.

The present invention is not limited to the use of the INVADERCREATOR software. Indeed, a variety of software programs are contemplated and are commercially available, including, but not limited to GCG Wisconsin Package (Genetics computer Group, Madison, Wis.) and Vector NTI (Informax, Rockville, Md.). Other detection assays may be used in the present invention.

Multiplex Reactions

Since its introduction in 1988 (Chamberlain, et al. Nucleic Acids Res., 16:11141 (1988)), multiplex PCR has become a routine means of amplifying multiple genetic loci in a single reaction. This approach has found utility in a number of research, as well as clinical, applications. Multiplex PCR has been described for use in diagnostic virology (Elnifro, et al. Clinical Microbiology Reviews, 13: 559 (2000)), paternity testing (Hidding and Schmitt, Forensic Sci. Int., 113: 47 (2000); Bauer et al., Int. J. Legal Med. 116: 39 (2002)), preimplantation genetic diagnosis (Ouhibi, et al., Curr Womens Health Rep. 1: 138 (2001)), microbial analysis in environmental and food samples (Rudi et al., Int J Food Microbiology, 78: 171 (2002)), and veterinary medicine (Zarlenga and Higgins, Vet Parasitol. 101: 215 (2001)), among others. Most recently, expansion of genetic analysis to whole genome levels, particularly for single nucleotide polymorphisms, or SNPs, has created a need for highly multiplexed PCR capabilities. Comparative genome-wide association and candidate gene studies require the ability to genotype between 100,000-500,000 SNPs per individual (Kwok, Molecular Medicine Today, 5: 538-5435 (1999); Kwok, Pharmacogenomics, 1: 231 (2000); Risch and Merikangas, Science, 273: 1516 (1996)). Moreover, SNPs in coding or regulatory regions alter gene function in important ways (Cargill et al. Nature Genetics, 22: 231 (1999); Halushka et al., Nature Genetics, 22: 239 (1999)), making these SNPs useful diagnostic tools in personalized medicine (Hagmann, Science, 285: 21 (1999); Cargill et al. Nature Genetics, 22: 231 (1999); Halushka et al., Nature Genetics, 22: 239 (1999)). Likewise, validating the medical association of a set of SNPs previously identified for their potential clinical relevance as part of a diagnostic panel will mean testing thousands of individuals for thousands of markers at a time.

Despite its broad appeal and utility, several factors complicate multiplex PCR amplification. Chief among these is the phenomenon of PCR or amplification bias, in which certain loci are amplified to a greater extent than others. Two classes of amplification bias have been described. One, referred to as PCR drift, is ascribed to stochastic variation in such steps as primer annealing during the early stages of the reaction (Polz and Cavanaugh, Applied and Environmental Microbiology, 64: 3724 (1998)), is not reproducible, and may be more prevalent when very small amounts of target molecules are being amplified (Walsh et al., PCR Methods and Applications, 1: 241 (1992)). The other, referred to as PCR selection, pertains to the preferential amplification of some loci based on primer characteristics, amplicon length, G-C content, and other properties of the genome (Polz, supra).

Another factor affecting the extent to which PCR reactions can be multiplexed is the inherent tendency of PCR reactions to reach a plateau phase. The plateau phase is seen in later PCR cycles and reflects the observation that amplicon generation moves from exponential to pseudo-linear accumulation and then eventually stops increasing. This effect appears to be due to non-specific interactions between the DNA polymerase and the double stranded products themselves. The molar ratio of product to enzyme in the plateau phase is typically consistent for several DNA polymerases, even when different amounts of enzyme are included in the reaction, and is approximately 30:1 product:enzyme. This effect thus limits the total amount of double-stranded product that can be generated in a PCR reaction such that the number of different loci amplified must be balanced against the total amount of each amplicon desired for subsequent analysis, e.g. by gel electrophoresis, primer extension, etc.

Because of these and other considerations, although multiplexed PCR including 50 loci has been reported (Lindblad-Toh et al., Nature Genet. 4: 381 (2000)), multiplexing is typically limited to fewer than ten distinct products. However, given the need to analyze as many as 100,000 to 450,000 SNPs from a single genomic DNA sample there is a clear need for a means of expanding the multiplexing capabilities of PCR reactions.

The present invention provides methods for substantial multiplexing of PCR reactions by, for example, combining the INVADER assay with multiplex PCR amplification. The INVADER assay provides a detection step and signal amplification that allows very large numbers of targets to be detected in a multiplex reaction. As desired, hundreds to thousands to hundreds of thousands of targets may be detected in a multiplex reaction.

Direct genotyping by the INVADER assay typically uses from 5 to 100 ng of human genomic DNA per SNP, depending on detection platform. For a small number of assays, the reactions can be performed directly with genomic DNA without target pre-amplification, however, for highly multiplex reactions, the amount of sample DNA may become a limiting factor.

Because the INVADER assay provides from $10^6$ to $10^7$ fold amplification of signal, multiplexed PCR in combination with the INVADER assay would use only limited target amplification as compared to a typical PCR. Consequently, low target amplification level alleviates interference between individual reactions in the mixture and reduces the inhibition of PCR by it's the accumulation of its products, thus providing for more extensive multiplexing. Additionally, it is contemplated that low amplification levels decrease a probability of target cross-contamination and decrease the number of PCR-induced mutations.

Uneven amplification of different loci presents one of the biggest challenges in the development of multiplexed PCR. Differences in amplification factors between two loci may result in a situation where the signal generated by an INVADER reaction with a slow-amplifying locus is below the limit of detection of the assay, while the signal from a fast-amplifying locus is beyond the saturation level of the assay. This problem can be addressed in several ways. In some embodiments, the INVADER reactions can be read at different time points, e.g., in real-time, thus significantly extending the dynamic range of the detection. In other embodiments, multiplex PCR can be performed under conditions that allow different loci to reach more similar levels of amplification. For example, primer concentrations can be limited, thereby allowing each locus to reach a more uniform level of amplification. In yet other embodiments, concentrations of PCR primers can be adjusted to balance amplification factors of different loci.

The present invention provides for the design and characteristics of highly multiplex PCR including hundreds to thousands of products in a single reaction. For example, the target pre-amplification provided by hundred-plex PCR reduces the amount of human genomic DNA required for INVADER-based SNP genotyping to less than 0.1 ng per assay. The specifics of highly multiplex PCR optimization and a computer program for the primer design are described in U.S. patent application Ser. Nos. 10/967,711 and 10/321,039 herein incorporated by reference in their entireties.

In addition to providing methods for highly multiplex PCR, the present invention further provides methods of conducting reverse transcription and target and signal amplification reactions in a single reaction vessel with no subsequent manipulations or reagent additions beyond initial reaction set-up. Such combined reactions are suitable for quantitative analysis of limiting target quantities in very short reaction times. Methods for conducting such reactions are described in U.S. patent application Ser. No. 11/266,723, herein incorporated by reference in its entirety.

ii. Other Detection Assays

The present invention is not limited to detection of target sequences by INVADER assay. The methods and compositions of the present invention find use in increasing the dynamic range of any number detection assays including, but not limited to, those described below.

In some embodiments, the methods and compositions of the present invention find use in increasing the dynamic range of a hybridization assay. A variety of hybridization assays using a variety of technologies for hybridization and detection are available. A description of a selection of assays is provided below.

In some embodiments, hybridization of a probe to the sequence of interest is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the target sequence being detected is allowed to contact the membrane under a condition or low, medium, or high stringency conditions. Unbound probe is removed and the presence of binding is detected by visualizing the labeled probe.

In some embodiments of the present invention, variant sequences are detected using a DNA chip (e.g., array) hybridization assay. In this assay, a series of oligonucleotide probes are affixed to a solid support. In some embodiments, the oligonucleotide probes are designed to be unique to a given target sequence. In preferred embodiments, the arrays comprise multiple probes (e.g., mismatch or different amounts of a completely complementary probe) in order to increase the dynamic range of the assay. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the target nucleic acid are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given target nuclei acid. Batches of beads are combined to form a pool specific to the array. To perform an assay, the BEAD ARRAY is contacted with a prepared subject sample (e.g., DNA). Hybridization is detected using any suitable method.

In other embodiments, the array methods described in U.S. Pat. Nos. 6,410,229 and 6,344,316; each of which is incorporated by reference herein, are utilized.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of DNA polymerases such as AMPLITAQ DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labelled antibody specific for biotin).

In yet other embodiments, the methods and compositions of the present invention are utilized with the method described in U.S. Pat. No. 6,528,254 (herein incorporated by reference in its entirety). The method comprises generating a cleavage structure using a primer and a nucleic acid polymerase and cleaving the cleavage structure with a FEN endonuclease.

In other embodiments, a ligase based detection assay is utilized with the methods and compositions of the present invention. For example, in some embodiments, the method described in U.S. Pat. Nos. 5,521,065 and 5,514,543 (each of which is herein incorporated by reference in its entirety) is utilized. Briefly, the method involves reacting a mixture of single-stranded nucleic acid fragments with a first probe which is complementary to a first region of the target sequence, and with a second probe which is complementary to a second region of the target sequence, where the first and second target regions are contiguous with one another, under hybridization conditions in which the two probes become stably hybridized to their associated target regions. Following hybridization, any of the first and second probes hybridized to contiguous first and second target regions are ligated, and the sample is tested for the presence of expected probe ligation product. The presence of ligated product indicates that the target sequence is present in the sample. In some embodiments, the ligation reaction is performed concurrent with a nucleic acid amplification reaction (See e.g., U.S. Pat. Nos. 6,130,073 and 5,912,148, each of which is herein incorporated by reference in its entirety).

In some embodiments, the present invention provides microarrays. Microarrays may be utilized with any of the detection assays described herein. The below discussion describes microarrays in the context of INVADER and TAQMAN assays. However, one skilled in the art recognizes that microarrays may be adapted for use with any number of detection assays.

Microarrays may comprise assay reagents and/or targets attached to or located on or near a solid surface (i.e. a microarray spot is formed) such that a detection assay may be performed on the solid surface. In some preferred embodiments, the microarray spots are generated to possess specific and defined chemical and physical characteristics. In other embodiments, the microarray may comprise a plurality of reaction chambers (e.g., capillaries), for conducting detection assays. In some such embodiments, nucleic acids or other detection assay components are attached to the surface of the reaction chamber. In other embodiments, detection assay components are all in the liquid phase or dried down in the reaction chamber.

As used herein, the term "microarray-spot" refers to the discreet area formed on a solid surface, in a layer of non-aqueous liquid in a microwell, or in a reaction chamber containing a population of detection assay reagents. A microarray-spot may be formed, for example, on a solid substrate (e.g. glass, TEFLON) or in a layer of non-aqueous liquid or other material that is on a solid surface, when a reagent sample comprising detection assay reagents is applied to the solid surface (or film on a solid surface) by a transfer means (e.g. pin spotting tool, inkjet printer, etc.). In preferred embodiments, the solid substrate (e.g. modified as described below) contains microwells and the microarray-spots are applied in the microwells. In other embodiments, the solid support serves as a platform on which microwells are printed/created and the necessary reagents are introduced to these microwells and the subsequent reaction(s) take place entirely in solution. Creation of a microwell on a solid support may be accomplished in a number of ways, including; surface tension, and etching of hydrophilic pockets (e.g. as described in patent publications assigned to Protogene Corp.). For example, the surface of a support may be coated with a hydrophobic layer, and a chemical component, that etches the hydrophobic layer, is then printed on to the support in small volumes (e.g., to generate local changes in the physical or chemical properties of the hydrophobic layer). The printing results in an array of hydrophilic microwells. An array of printed hydrophobic or hydrophilic towers may be employed to create microarrays. A surface of a slide may be coated with a hydrophobic layer, and then a solution is printed on the support that creates a hydrophilic layer on top of the hydrophobic surface. The printing results in an array of hydrophilic towers. Mechanical microwells may be created using physical barriers, +/−chemical barriers. For example, microgrids such as gold grids may be immobilized on a support, or microwells may be drilled into the support (e.g. as demonstrated by BML). Also, a microarray may be printed on the support using hydrophilic ink such as TEFLON. Such arrays are commercially available through Precision Lab Products, LLC, Middleton, Wis. In yet another variant, data of customer preferences with respect to the format of the detection assay array are stored on a database used with components of the invention. This information can be used to automatically configure products for a particular customer based upon minimal identification information for a customer, e.g. name, account number or password. In some embodiments, the desired reactions components (e.g., target nucleic acids or detection assay components) are spotted or delivered into wells and then taken up into small reaction chambers such as capillaries. The reaction then occurs within the reaction chamber.

Many types of methods may be used for printing of desired reagents into microarrays (e.g. microarray spots printed into microwells). In some embodiments, a pin tool is used to load the array (e.g. generate a microarray spot) mechanically (see, e.g., Shalon, Genome Methods, 6:639 [1996], herein incorporated by reference). In other embodiments, ink jet technology is used to print oligonucleotides onto a solid surface (e.g., O'Donnelly-Maloney et al., Genetic Analysis: Biomolecular Engineering, 13:151 [1996], herein incorporated by reference) in order to create one or more microarray spots in a well.

Examples of desired reagents for printing into/onto solid supports (e.g. with microwell arrays) include, but are not limited to, molecular reagents, such as INVADER reaction reagents, designed to perform a nucleic acid detection assay (e.g., an array of SNP detection assays could be printed in the wells); and target nucleic acid, such as human genomic DNA (hgDNA), resulting in an array of different samples. Also, desired reagents may be simultaneously supplied with the etching/coating reagent or printed into/onto the microwells/towers subsequent to the etching process. For arrays created with mechanical barriers the desired reagents are, for example, printed into the resulting wells. In some embodiments, the desired reagents may need to be printed in a solution that sufficiently coats the microwell and creates a hydrophilic, reaction friendly, environment such as a high protein solution (e.g. BSA, non-fat dry milk). In certain embodiments, the desired reagents may also need to be printed in a solution that creates a "coating" over the reagents that immobilizes the reagents, this could be accomplished with the addition of a high molecular weight carbohydrate such as FICOLL or dextran. In some embodiments, the coating is oil.

Application of the target solution to the microarray (or reaction reagents if the target has been printed down or taken up in a reaction chamber) may be accomplished in a number of ways. For example, the solid support may be dipped into a solution containing the target, or by putting the support in a chamber with at least two openings then feeding the target solution into one of the openings and then pulling the solution across the surface with a vacuum or allowing it to flow across the surface via capillary action. Examples of devices useful for performing such methods include, but are not limited to, TECAN—GenePaint system, and AutoGenomics AutoGene System. In yet another embodiment spotters commercially available from Virtek Corp. are used to spot various detection assays onto plates, slides and the like.

In some embodiments, solutions (e.g. reaction reagents or target solutions) are dragged, rolled, or squeegeed across the surface of the support. One type of device useful for this type of application is a framed holder that holds the support. At one end of the holder is a roller/squeegee or something similar that would have a channel for loading of the target solution in front of it. The process of moving the roller/squeegee across the surface applies the target solution to the microwells. At the end opposite end of the holder is a reservoir that would capture the unused target solution (thus allowing for reuse on another array if desired). Behind the roller/squeegee is an evaporation barrier (e.g., mineral oil, optically clear adhesive tape etc.) and it is applied as the roller/squeegee move across the surface.

The application of a target solution to microwell or reaction chamber arrays results in the deposition of the solution at each of the microwell or reaction chamber locations. The chemical and/or mechanical barriers would maintain the integrity of the array and prevent cross-contamination of reagents from element to element. In some preferred embodiments, materials in the microwells or reaction chambers are dried. In some such embodiments, the reagents are rehydrated by the target solution (or detection assay component solution) resulting in an ultra-low volume reaction mix. In some embodiments, the microarray reactions are covered with mineral oil or some other suitable evaporation barrier or humidity chamber to allow high temperature incubation. The signal generated may be detected directly through the applied evaporation barrier using a fluorescence microscope, array reader or standard fluorescence plate reader.

Advantages of the use of a microwell-microarray, for running INVADER assays (e.g. dried down INVADER assay components in each well) include, but are not limited to: the ability to use the INVADER Biplex format for a nucleic acid detection assay; sufficient sensitivity to detect hgDNA directly, the ability to use "universal" FRET cassettes; no attachment chemistry needed (which means already existing off the shelf reagents could be used to print the microarrays), no need to fractionate hgDNA to account for surface effect on hybridization, low mass of hgDNA needed to make tens of thousands of calls, low volume need (e.g. a 100 µm microwell would have a volume of 0.28 nl, and at $10^4$ microwells per array a volume of 2.8 µl would fill all wells), a solution of 333 ng/µl hgDNA would result in ~100 copies per microwell (this is 33× more concentrated than the use of 100 ng hgDNA in a 20 µl reaction), thus 2.8 µl×333 ng/µl=670 ng hgDNA for $10^4$ calls or 0.07 ng per call. It is appreciated that other detection assays can also be presented in this format.

Generating and Using Microarray-Spots with Non-Aqueous Liquids

In certain preferred embodiments, the present invention provides methods for generating microarray spots in wells by applying a detection assay reagent solution to a well containing non-aqueous liquid. In other preferred embodiments, the present invention provides methods of contacting a microarray-spot with a test sample solution (e.g. comprising target nucleic acids) by shooting the test sample solution through a layer of non-aqueous liquid covering the microarray spot. In certain embodiments, the solid supports are coated with sol-gel films (described below in more detail).

In some embodiments, the present invention provides methods comprising; a) providing; i) a solid support comprising a well, ii) a non-aqueous liquid, and iii) a detection reagent solution; and b) adding the non-aqueous liquid to the well, and c) adding the detection reagent solution to the well through the non-aqueous liquid under conditions such that at least one microarray-spot is formed in the well. In other embodiments, the methods further comprise step d) contacting the at least one microarray-spot with a test sample solution. In additional embodiments, the contacting comprises propelling the test sample solution through the non-aqueous liquid in the well.

In particular embodiments, the non-aqueous liquid is oil. In other embodiments, the solid support comprises a plurality of wells, and the method is performed with the plurality of wells. In further embodiments, at least two microarray-spots are formed simultaneously (e.g. in at least two of the plurality of wells).

In some embodiments, the test sample solution comprises a target nucleic acid molecule. In preferred embodiments, the target solution comprises less than 800 copies of a target nucleic acid molecule, or less than 400 copies of a target nucleic acid molecule or less than 200 copies of a target nucleic acid molecule. In particular embodiments, the contacting the microarray-spot with the test sample solution identifies the presence or absence of a polymorphism, or other desired particular sequence to be detected, in the target nucleic acid molecule. In some embodiments, wells are coated with a sol-gel coating (e.g. prior to microarray-spot formation).

In other embodiments, the detection reagent solution comprises components configured for use with a detection assay selected from; TAQMAN assay, or an INVADER assay, a polymerase chain reaction assay, a rolling circle extension assay, a sequencing assay, a hybridization assay employing a probe complementary to the polymorphism, a bead array assay, a primer extension assay, an enzyme mismatch cleavage assay, a branched hybridization assay, a NASBA assay, a molecular beacon assay, a cycling probe assay, a ligase chain reaction assay, and a sandwich hybridization assay. In preferred embodiments, the detection reagent solution comprises INVADER oligonucleotides, and 5' probe oligonucleotides.

In additional embodiments, the contacting is performed with a SYNQUAD nanovolume pipetting system, or other fluid transfer system or device. In preferred embodiments, the commercially available CARTESIAN SYNQUAD nanovolume pipetting system is employed. Similar devices may also be employed, including those described in U.S. Pat. No. 6,063,339 and U.S. Pat. No. 6,258,103, both of which are specifically incorporated by reference, as well as PCT applications: WO0157254; WO0049959; WO0001798; and WO9942804; all of which are specifically incorporated by reference.

In particular embodiments, at least 2 microarray-spots are formed in the well (or at least 3 or 4 or 5 microarray-sports are formed in each well). In multi-well formats, employing multiple microarray-spots multiplies the number of reactions that can be performed on a single solid support (e.g. if 4 microarray-spots are formed in each of the 1536 wells in an a 1536 well plate, then 6144 microarray-spots would be available for performing detection reactions). In further embodiments, the present invention provides a solid support with a well (or wells) formed by the methods described above.

In some embodiments, the present invention provides methods comprising; a) providing; i) a solid support comprising a microarray-spot, ii) a non-aqueous liquid; and iii) a test sample solution; and b) covering the microarray-spot with a layer of the non-aqueous liquid, and c) contacting the microarray-spot with the test sample solution through the layer of non-aqueous liquid. In other embodiments, the test sample solution comprises a target nucleic acid molecule. In further embodiments, the contacting identifies the presence or absence of at least one polymorphism in the target nucleic acid molecule. In preferred embodiments, the test sample solution comprises a target nucleic acid molecule. In preferred embodiments, the target solution comprises less than 800 copies of a target nucleic acid molecule, or less than 400 copies of a target nucleic acid molecule or less than 200 copies of a target nucleic acid molecule.

In certain embodiments, the microarray-spot comprises components configured for use with a detection assay selected from; TAQMAN assay, or an INVADER assay, a polymerase chain reaction assay, a rolling circle extension assay, a sequencing assay, a hybridization assay employing a probe complementary to the polymorphism, a bead array assay, a primer extension assay, an enzyme mismatch cleavage assay, a branched hybridization assay, a NASBA assay, a molecular beacon assay, a cycling probe assay, a ligase chain reaction assay, and a sandwich hybridization assay. In preferred embodiments, the microarray-spot comprises INVADER oligonucleotides, and 5' probe oligonucleotides.

In some embodiments, the solid support comprises a well, and the microarray-spot is located in the well. In certain embodiments, the non-aqueous liquid is oil. In other embodiments, the solid support comprises a plurality of wells, and the method is performed with the plurality of wells. In particular embodiments, at least two microarray-spots are formed simultaneously. In some embodiments, at least 2 microarray-spots are formed in the well (or at least 3 or 4 or 5 microarray-sports are formed in each well). In multi-well formats, employing multiple microarray-spots multiplies the number of reactions that can be performed on a single solid support (e.g. if 4 microarray-spots are formed in each of the 1536 wells in an a 1536 well plate, then 6144 microarray-spots would be available for performing detection reactions; if etched 3072 well plates are used, additional spots may be formed). In further embodiments, the present invention provides a solid support with a well (or wells) formed by the methods described above.

In some embodiments, the contacting comprises propelling the test sample solution through the non-aqueous liquid in the well. In other embodiments, the non-aqueous liquid is mineral oil. In additional embodiments, the non-aqueous liquid is selected from mineral oil, a seed oil, and an oil derived from petroleum.

In additional embodiments, the contacting is performed with a SYNQUAD nanovolume pipetting system, or other fluid transfer system or device. In preferred embodiments, the commercially available CARTESIAN SYNQUAD nanovolume pipetting system is employed. Similar devices may also be employed, including those described in U.S. Pat. Nos. 6,063,339 and 6,258,103, both of which are specifically incorporated by reference, as well as PCT applications: WO0157254; WO0049959; WO0001798; and WO9942804; all of which are specifically incorporated by reference.

In some embodiments, the present invention provides systems comprising; a) a nonvolume pipetting system (e.g., SYNQUAD), and b) a solid support comprising a microarray-spot, wherein the microarray spot is covering with a layer of a non-aqueous liquid. In other embodiments, the system further comprises a test sample solution.

iv. Formats for Assays on a Solid Support

In some embodiments, detection assays are performed on a solid support. The below discussion describes assays on a solid support in the context of the INVADER assay. However, one skilled in the relevant arts recognizes that the methods described herein can be adapted for use with any nucleic acid detection assay (e.g., the detection assays described herein).

The present invention is not limited to a particular configuration of the INVADER assay. Any number of suitable configurations of the component oligonucleotides may be utilized. For example, in some embodiments of the present invention, the probe oligonucleotide is bound to a solid support and the INVADER oligonucleotide and genomic DNA (or RNA) target are provided in solution. In other embodiments of the present invention, the INVADER oligonucleotide is bound to the support and the probe and target are in solution. In yet other embodiments, both the probe and INVADER oligonucleotides are bound to the solid support. In further embodiments, the target nucleic acid is bound directly or indirectly (e.g., through hybridization to a bound oligonucleotide that is not part of a cleavage structure) to a solid support, and either or both of the probe and INVADER oligonucleotides are provided either in solution, or bound to a support. In still further embodiments, a primary INVADER assay reaction is carried out in solution and one or more components of a secondary reaction are bound to a solid support. In yet other embodiments, all of the components necessary for an INVADER assay reaction, including cleavage agents, are bound to a solid support.

The present invention is not limited to the configurations described herein. Indeed, one skilled in the art recognizes that any number of additional configurations may be utilized. Any configuration that supports a detectable invasive cleavage reaction may be utilized. Additional configurations are identified using any suitable method, including, but not limited to, those disclosed herein.

In some embodiments, the probe oligonucleotide is bound to a solid support. In some embodiments, the probe is a labeled Signal Probe oligonucleotide. The signal probe is cleaved to release a signal molecule indicative of the presence of a given target molecule. In some embodiments, the signal molecule is a fluorescence donor in an energy transfer reaction (e.g., FRET), whose emission increases in response to separation from a quenching fluorescence acceptor. In other embodiments, the signal molecule is a fluorescent moiety that is detected only upon its release into solution. It yet other embodiments, the signal molecule is a fluorescently labeled small molecule that is separated from the full length Signal Probe by carrying a distinct charge.

In some embodiments, a system is designed in which no separation steps are required to visualize the signal generated by the reaction. In some embodiments, this is accomplished in the FRET system in which the fluorescence donor remains affixed to the solid support following cleavage of the signal probe. This design has several complexities that stem from the nature of the FRET reaction. The quenching in the FRET signal molecule is only 97-99% efficient (i.e. not all of the energy emitted by the donor will be absorbed by the quencher). To detect the fluorescence of the unquenched donor above the background of the uncleaved probes, it is necessary to cleave 1-3% of the probe molecules. Assuming that in a 100 μm×100 μm area, there are ~$10^8$ probes bound, then ~$10^6$ should be cleaved to generate a signal detectable above the inherent background generated by those probes. Probe cycling in an INVADER assay reaction on a single target molecule can generate approximately 1000-2000 cleaved probe molecules per hour (assuming a turnover rate of 15-30 events/target/min). Roughly 1000 target molecules are required to generate this level of cleaved Signal Probes. Assuming a reaction volume of 1 nL, the necessary target concentration becomes 1 pM, well within the range of the maximum that can be manipulated (e.g., 0.5-2.5 pM). At less than maximal probe densities, it would nonetheless be necessary to deliver at least 10-20 target molecules (i.e. a 10-20 fM solution) to each reaction area to ensure a statistical likelihood that each will contain target. The same target concentration considerations apply to other, non-FRET alternatives, for example, release of a single fluorescent group into solution, with or without a quenching fluorophore and release of a positively charged signal molecule even though <1% cleavage would be detectable with these other methods. Accordingly, in some embodiments, dilute solutions are used in conjunction with longer reaction times (e.g. a 100 fM solution could be applied and the reactions run for 10-24 hours).

In some embodiment of the present invention, the INVADER oligonucleotide is bound to the solid support and the probe oligonucleotide is free in solution. In this embodiment, there are no restrictions on the length of the INVADER oligonucleotide-target duplex, since the INVADER oligonucleotide does not need to cycle on and off the target, as does the signal probe. Thus, in some embodiments where the INVADER oligonucleotide is bound to a solid support, the INVADER oligonucleotide is used as a "capture" oligonucleotide to concentrate target molecules from solution onto the solid phase through continuous application of sample to the solid support. For example, by applying 1 ml of a 1 mg/ml target solution, it is possible to bind $10^6$-$10^8$ target molecules in a 100 μM×100 μM area. Moreover, because the INVADER oligonucleotide-target interaction is designed to be stable, in some embodiments, the support is washed to remove unbound target and unwanted sample impurities prior to applying the signal probes, enzyme, etc., to ensure even lower background levels. In other embodiments, a capture oligonucleotide complementary to a distinct region in the proximity of the locus being investigated is utilized.

Several possibilities exist for separation of cleaved from uncleaved signal probe reactions where INVADER oligonucleotides are bound the solid support and signal probe oligonucleotides are free in solution. In preferred embodiments, a labeling strategy is utilized that makes it possible to chemically differentiate cleaved from uncleaved probe since both full length and cleaved probes are in solution. For example, in some embodiments (e.g., FRET signal probe), full length probe is quenched but the cleavage product generates fluorescent signal. In other embodiment (e.g, CRE), the full length probe is negatively charged but the cleaved probe is positively charged.

However, in some preferred embodiments, CRE separation is utilized. First, the cleaved signal probes generated by the CRE approach are actively captured on a negatively charged electrode. This capture results in partitioning from uncleaved molecules as well as concentration of the labeled, cleaved probes by as much as an order of magnitude. Second, the use of an electric field to capture the cleaved probe eliminates the need to micromachine tiny wells to prevent diffusion of the cleaved probes.

In some embodiments of the present invention, both a probe and an INVADER oligonucleotide are bound to a solid support. In preferred embodiments, probe and INVADER oligonucleotides are placed in close proximity on the same solid support such that a target nucleic acid may bind both the probe and INVADER oligonucleotides. In some embodiments, the oligonucleotides are attached via spacer molecules in order to improve their accessibility and decrease interactions between oligonucleotides.

In some preferred embodiments, a single INVADER oligonucleotide is configured to allow it to contact and initiate multiple cleavage reactions. For example, in some embodiments, one INVADER oligonucleotide is surrounded on a solid support by multiple Signal Probe oligonucleotides. A target nucleic acid binds to an INVADER and a probe oligonucleotide. The Signal Probe is cleaved (generating signal) and released, leaving the target bound to the INVADER oligonucleotide. This target:INVADER oligonucleotide complex is then able to contact another Signal Probe and promote another cleavage event. In this manner, the signal generated from one target and one INVADER oligonucleotide is amplified.

In other embodiments, the probe and INVADER oligonucleotides are combined in one molecule. The connection between the probe and INVADER portions of the single molecule may be nucleic acid, or may be a non-nucleic acid linker (e.g., a carbon linker, a peptide chain).

In some embodiments, a primary INVADER assay reaction is performed in solution and a secondary reaction is performed on a solid support. Cleaved probes from the primary INVADER assay reaction are contacted with a solid support containing one or more components of a cleavage structure, including but not limited to a secondary target nucleic acid, a secondary probe or a secondary INVADER oligonucleotide. In a preferred embodiment, the component is a one-piece secondary oligonucleotide, or cassette, comprising both a secondary target portion and a secondary probe portion. In a particularly preferred embodiment, the cassette is labeled to allow detection of cleavage of the cassette by a FRET. The secondary signal oligonucleotide may be labeled using any suitable method including, but not limited to, those disclosed herein. It will be appreciated that any of the embodiments described above for configuring an INVADER assay reaction on a support may be used in configuring a secondary or subsequent INVADER assay reaction on a support.

In some embodiments of the present invention, the target nucleic acid (e.g, genomic DNA) is bound to the solid support. In some embodiments, the INVADER and Probe oligonucleotides are free in solution. In other embodiments, both the target nucleic acid, the INVADER oligonucleotide, and the Probe (e.g, Signal Probe) oligonucleotides are bound. In yet other embodiments, a secondary oligonucleotide (e.g, a FRET oligonucleotide) is included in the reaction. In some embodiments, the FRET oligonucleotide is free in solution. In other embodiments, the FRET oligonucleotide is bound to the solid support.

In some embodiments, the cleavage means (e.g., enzyme) is bound to a solid support. In some embodiments, the target nucleic acid, probe oligonucleotide, and INVADER oligonucleotide are provided in solution. In other embodiments, one or more of the nucleic acids is bound to the solid support.

Any suitable method may be used for the attachment of a cleavage enzyme to a solid support, including, but not limited to, covalent attachment to a support (See e.g., Chemukhin and Klenova, Anal. Biochem., 280:178 [2000]), biotinylation of the enzyme and attachment via avidin (See e.g., Suter et al., Immunol. Lett. 13:313 [1986]), and attachment via antibodies (See e.g., Bilkova et al., J. Chromatogr. A, 852:141 [1999]).

In some embodiments of the present invention, oligonucleotides are attached to a solid support via a spacer or linker molecule. The present invention is not limited to any one mechanism. Indeed, an understanding of the mechanism is not necessary to practice the present invention. Nonetheless, it is contemplated that spacer molecules enhance INVADER assay reactions by improving the accessibility of oligonucleotides and decreasing interactions between oligonucleotides. The use of linkers, which can be incorporated during oligonucleotide synthesis, has been shown to increase hybridization efficiency relative to capture oligonucleotides that contain no linkers (Guo et al., Nucleic Acids Res., 22:5456 [1994]; Maskos and Southern, Nucleic Acids Res., 20:1679 [1992]; Shchepinov et al., Nucleic Acids Research 25:1155 [1997]).

Spacer molecules may be comprised of any suitable material. Preferred materials are those that are stable under reaction conditions utilized and non-reactive with the components of the INVADER assay. Suitable materials include, but are not limited to, carbon chains (e.g., including but not limited to $C_{18}$), poly nucleotides (e.g., including, but not limited to, polyI, polyT, polyG, polyC, and polyA), and polyglycols (e.g., hexaethylene glycol).

Spacer molecules may be of any length. Accordingly in some embodiments, multiple spacer molecules are attached end to end to achieve the desired length spacer. For example, in some embodiments, multiple $C_{18}$ or hexaethylene glycol spacers (e.g., including, but not limited to, 5, 10, or 20 spacer molecules) are combined. The optimum spacer length is dependent on the particular application and solid support used. To determine the appropriate length, different lengths are selected (e.g, 5, 10, or 20 $C_{18}$ or hexaethylene glycol spacers molecules) and reactions are performed as described herein to determine which spacer gives the most efficient reaction.

The present invention is not limited to any one solid support. In some embodiments, reactions are performed on microtiter plates (e.g., polystyrene plates containing either containing 96 or 384 wells). For example, in some embodiments, streptavidin (SA) coated 96-well or 384-well microtiter plates (Boehringer Mannheim Biochemicals, Indianapolis, Ind.) are used as solid supports. In such embodiments, signal can be measured using standard fluorescent, chemiluminescent or colorimetric microtiter plate readers.

In some embodiments, INVADER assay reactions are carried out on particles or beads. The particles can be made of any suitable material, including, but not limited to, latex. In some embodiments, columns containing a particle matrix suitable for attachment of oligonucleotides are used. In a some embodiments, reactions are performed in minicolumns (e.g. DARAS, Tepnel, Cheshire, England). The columns contain microbeads to which oligonucleotides are covalently bound and subsequently used as capture probes or in enzymatic reactions. The use of minicolumns allows approximation of the bound oligonucleotide concentrations that will be attainable in a miniaturized chip format. Oligonucleotide binding is limited by the capacity of the support (i.e. $\sim 10^{12}/cm^2$). Thus, bound oligonucleotide concentration can only be increased by increasing the surface area to volume ratio of the reaction vessel. For example, one well of a 96-well microtiter plate, with a surface area of ~1 cm² and a volume of 400 µl has a maximal bound oligonucleotide concentration of ~25 nM. On the other hand, a 100 µm×100 µm×100 µM volume in a microchip has a surface area of $10^4$ µm² and a volume of 1 nL, resulting in a bound oligonucleotide concentration of 0.2 µM. Similar increased surface area: volume ratios can be obtained by using microbeads. Given a binding capacity of $\geq 10^{14}$ oligonucleotides in a 30 µl volume, these beads allow bound oligonucleotide concentrations of 0.2-10 µM, i.e. comparable to those anticipated for microchips.

In some embodiments, INVADER reaction are carried out on a HydroGel (Packard Instrument Company, Meriden, Conn.) support. HydroGel is porous 3D hydrophilic polymer matrix. The matrix consists of a film of polyacrylamide polymerized onto a microscope slide. A coupling moiety is co-polymerized into the matrix that permits the immobilization of aminated oligonucleotide molecules by reductive amination. Covalent attachment by amine groups permits the immobilization of nucleic acid probes at specific attachment points (usually their ends), and the hydrogel provides a 3D matrix approximating a bulk solution phase, avoiding a solid/solution phase interface.

In other embodiments, INVADER reactions are conducted on a solid support using a BEADARRAY (Illumina, San Diego, Calif.) technology. The technology combines fiber optic bundles and beads that self-assemble into an array. Each fiber optic bundle contains thousands to millions of individual fibers depending on the diameter of the bundle. Sensors are affixed to each beads in a given batch. The particular molecules on a bead define that bead's function as a sensor. To form an array, fiber optic bundles are dipped into pools of coated beads. The coated beads are drawn into the wells, one bead per well, on the end of each fiber in the bundle.

The present invention is not limited to the solid supports described above. Indeed, a variety of other solid supports are contemplated including, but not limited to, glass microscope slides, glass wafers, gold, silicon, microchips, and other plastic, metal, ceramic, or biological surfaces.

In some embodiments of the present invention, solid supports are coated with a material to aid in the attachment of oligonucleotides. The present invention is not limited to any one surface coating. Indeed, a variety of coatings are contemplated including, but not limited to, those described below.

In some embodiments, solid support INVADER assay reactions are carried out on solid supports coated with gold. The gold can be attached to any suitable solid support including, but not limited to, microparticles, microbeads, microscope slides, and microtiter plates. In some embodiments, the gold is functionalized with thiol-reactive maleimide moieties that can be reacted with thiol modified DNA (See e.g., Frutos et al., Nuc. Acid. Res., 25:4748 [1997]; Frey and Corn, Analytical Chem, 68:3187 [1996]; Jordan et al., Analytical Chem, 694939 [1997]; and U.S. Pat. No. 5,472,881; herein incorporated by reference).

In other embodiments, solid support INVADER assay reactions are carried out on supports coated with silicon. The silicon can be attached to any suitable support, including, but not limited to, those described above and in the illustrative examples provided below.

Additionally, in some embodiments, solid supports are coated with a molecule (e.g., a protein) to aid in the attachment of nucleic acids. The present invention is not limited to any particular surface coating. Any suitable material may be utilized including, but not limited to, proteins such as streptavidin. Thus, in some embodiments, oligonucleotides are attached to solid supports via terminal biotin or $NH_2$-mediated linkages included during oligonucleotide synthesis. INVADER oligonucleotides are attached to the support at their 5' ends and Signal Probes are attached at their 3' ends. In some embodiment, oligonucleotides are attached via a linker proximal to the attachment point. In a preferred embodiment, attachment is via a 40 atom linker with a low negative charge density as described in (Shchepinov et al., Nucleic Acids Research 25: 1155 [1997]).

In other embodiments, oligonucleotides are attached to solid support via antigen: antibody interaction. For Example, in some embodiments, an antigen (e.g., protein A or Protein G) is attached to a solid support and IgG is attached to oligonucleotides. In other embodiments, IgG is attached to a solid support and an antigen (e.g., Protein A or Protein G) is attached to oligonucleotides.

In some embodiments, oligonucleotides are targeted to specific sites on the solid support. As noted above, when multiple oligonucleotides are bound to the solid support, the oligonucleotides may be synthesized directly on the surface using any number of methods known in the art (e.g., including but not limited to methods described in PCT publications WO 95/11995, WO 99/42813 and WO 02/04597, and U.S. Pat. Nos. 5,424,186; 5,744,305; and 6,375,903, each incorporated by reference herein).

Any number of techniques for the addressing of oligonucleotides may be utilized. For example, in some embodiments, solid support surfaces are electrically polarized at one given site in order to attract a particular DNA molecule (e.g, Nanogen, CA). In other embodiments, a pin tool may be used to load the array mechanically (Shalon, Genome Methods, 6:639 [1996]. In other embodiments, ink jet technology is used to print oligonucleotides onto an active surface (e.g., O'Donnelly-Maloney et al., Genetic Analysis: Biomolecular Engineering, 13:151 [1996]).

In some preferred embodiments utilizing gold surfaces, the gold surfaces are further modified to create addressable DNA arrays by photopatterning self-assembled monolayers to form hydrophilic and hydrophobic regions. Alkanethiol chemistry is utilized to create self-assembled monolayers (Nuzzo et al., JACS, 105:4481 [1983]). DNA is placed on the hydrophilic regions by using an automated robotic device (e.g., a pin-loading tool).

v. Reaction Vessels

The detection assays of the present invention may be performed using any suitable reaction vessel. As used herein, the term "reaction vessel" refers to a system in which a reaction may be conducted, including but not limited to test tubes, wells, microwells (e.g., wells in microtitre assay plates such as, 96-well, 384-well and 1536-well assay plates), capillary tubes, ends of fibers such as optical fibers, microfluidic devices such as fluidic chips, cartridges and cards (including but not limited to those described, e.g., in U.S. Pat. No. 6,126,899, to Woudenberg, et al., U.S. Pat. Nos. 6,627,159, 6,720,187, and 6,734,401 to Bedingham, et al., U.S. Pat. Nos. 6,319,469 and 6,709,869 to Mian, et al., U.S. Pat. Nos. 5,587,128 and 6,660,517 to Wilding, et al.), or a test site on any surface (including but not limited to a glass, plastic or silicon surface, a bead, a microchip, or an non-solid surface, such as a gel or a dendrimer).

In some preferred embodiments, reactions are conducted using a 3M microfluidic card (3M, St. Paul, Minn.). The 3M card has 8 loading ports, each of which is configured to supply liquid reagent to 48 individual reaction chambers upon centrifugation of the card. The reaction chambers contain pre-dispensed and dried assay reaction components for detection

III. T-Structure Invasive Cleavage Assays and Amplification Methods

Figure 6:
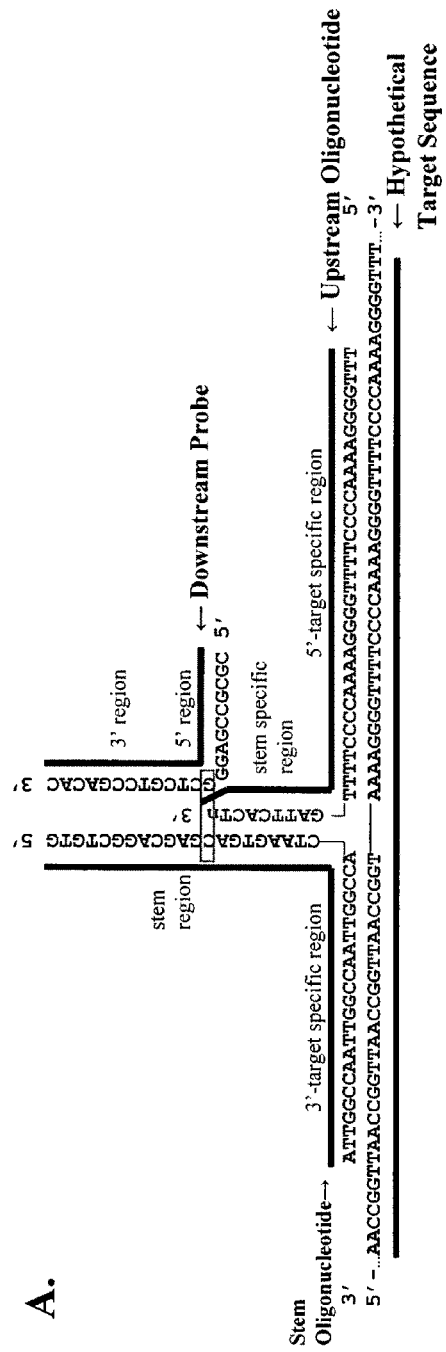
FIG. 6 shows one exemplary embodiment of a T-structure invasive cleavage assay of the present invention.
Figure 6:
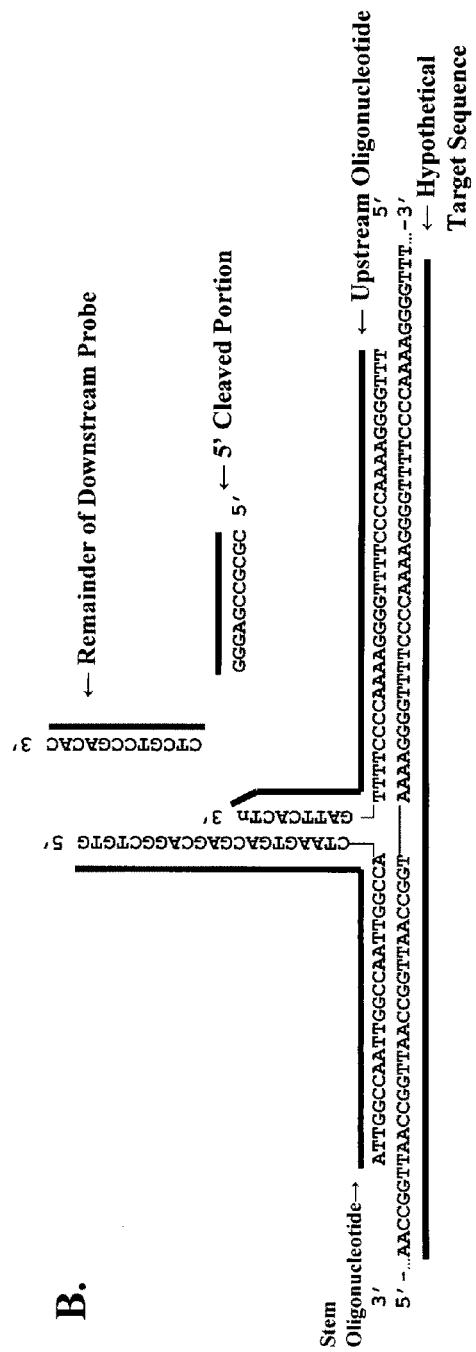

In certain embodiments, the present invention provides methods, kits, and compositions for performing invasive cleavage assays (e.g., the INVADER assay) in a T-structure configuration, where the T-structure is formed by the combination of a stem oligonucleotide, an upstream oligonucleotide, and a downstream probe. These oligonucleotides may be provided in a reaction or formed in the reaction (e.g., by polymerization). An exemplary embodiment of a T-structure invasive cleavage assay, specifically employing the INVADER assay, is shown in FIG. 6. As shown in FIG. 6, T-structure assays involve the use of a stem oligonucleotide that has: 1) a 3' target specific region configured to hybridize to a target sequence, and 2) a stem region which is configured to form the target region for an invasive cleavage assay, such as the INVADER assay. Also as shown in FIG. 6, the upstream oligonucleotide has three regions: 1) a 5' target specific region configured to hybridize to the target sequence; 2) a stem specific region configured to hybridize to the stem region of the stem oligonucleotide, and 3) a 3' region configured to not hybridize to the stem region. The third oligonucleotide used to form a T-structure for invasive cleavage assays is the downstream probe, which has: 1) a 3' region configured to hybridize to the stem region of the stem oligonucleotide and 2) a 5' region configured to not hybridize to the stem region of the stem oligonucleotide.

Generally, the region of inter-oligonucleotide complimentarity between the stem oligonucleotide and upstream oligonucleotide is sufficiently short (e.g. FIG. 6 shows a 9 base region) such that stable hybridization of the two is not favored at the temperature of the invasive cleavage assay employed (e.g. INVADER assay). However, in the presence of the target, as shown in FIG. 6, the two oligonucleotides are brought to together to form a secondary structure. It is noted that the target specific regions of the stem and upstream oligonucleotides are preferably contiguous on the target sequence. However, in certain embodiments, there is a gap between the two target specific regions (e.g. one base gap, two base gap, three base gap, etc.).

Figure 5:
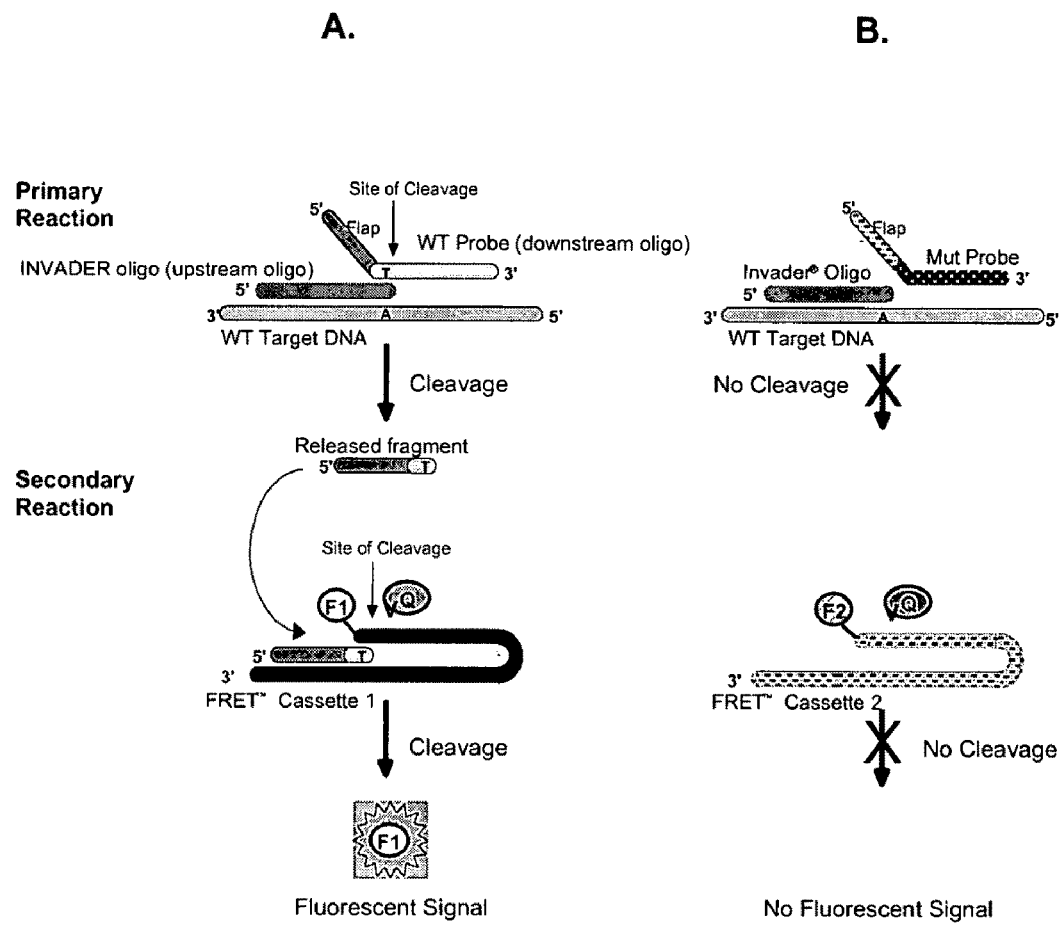
FIG. 5 shows an overview of one exemplary embodiment of the INVADER assay.

When the downstream probe is added with sequence complimentary to additional non-target sequence in the stem oligonucleotide, an invasive cleavage structure is formed and recognized by a DNA CLEAVASE enzyme. FIG. 6A shows a boxed area that can be recognized by a cleavage agent such that the downstream probe is cleaved, resulting in the cleavage of the downstream probe as shown in FIG. 6B. FIG. 6B shows the exemplary cleaved portion that is generated, that can then be detected by, for example, serving as the upstream oligonucleotide in a secondary invasive cleavage reaction that releases a detectable signal (e.g., as shown in FIG. 5).

One advantage of the T-structure invasive cleavage assays is the ability to use a single cleavage enzymes when detecting RNA templates (e.g. viral RNA targets) in multiplex reactions containing DNA targets or when use of hairpin FRET cassettes is desired. Generally, an enzyme optimal for detection of invasive cleavage structure forming DNA oligos on an RNA template is different from the enzyme optimal for secondary detection of cleaved DNA flaps on a DNA FRET-probe template. T-structure invasive cleavage assays allows the use of a single cleavage agent that is optimized for use with DNA targets since no cleavage structures involving RNA are involved, even thought the original target sequence may be RNA.

The T-structure invasive cleavage assays of the present invention have additional advantages. Because the binding site for the downstream probe oligonucleotide is on the user-supplied stem oligonucleotide, multiple stem oligonucleotides having different target specific regions and the same stem regions can be used simultaneously to detect multiple different regions of the same template (e.g., multiple sites on the same viral RNA genome). The primary cleavage reaction will generate many copies of the same cleaved flap for detection in a single secondary invasive cleavage reaction (e.g. as shown in FIG. 5). In this way, the specificity and sensitivity of the system can be increased as the signal generated in the presence of template increases non-linearly with the number of different T-structure forming oligonucleotide sets used per given number of template copies. The detection of the formation and cleavage of the cleavage structure can be detected both directly (e.g. detecting the cleaved flaps) or indirectly (e.g., measuring some other part of the assay indicative of the formation and cleavage of the cleavage structure).

The use of T-structures invasive cleavage assays is not limited to the detection of RNA templates, but can be used for DNA templates as well. As noted above, several T-structure forming oligonucleotide sets with the same stem region can be used simultaneously to increase the specificity and/or sensitivity of the assay. Other embodiments include the use of third, fourth, fifth, and more oligonucleotides to form more complicated superstructures. These multiple oligonucleotide structures can be designed so that only two of the set contain regions with binding affinity for a target nucleotide, and the remaining oligonucleotides contain affinity for each other to form higher-order structures on the template DNA such as cruciform of X-structures, star structures, and others. These embodiments can increase the sensitivity, specificity, and stability of the detection assay. In an additional embodiment, oligonucleotides containing modified bases (such as 2'-O-methylation, or the like) can be used to increase the specificity, sensitivity, or dynamic range of the detection assay.

Figure 7:
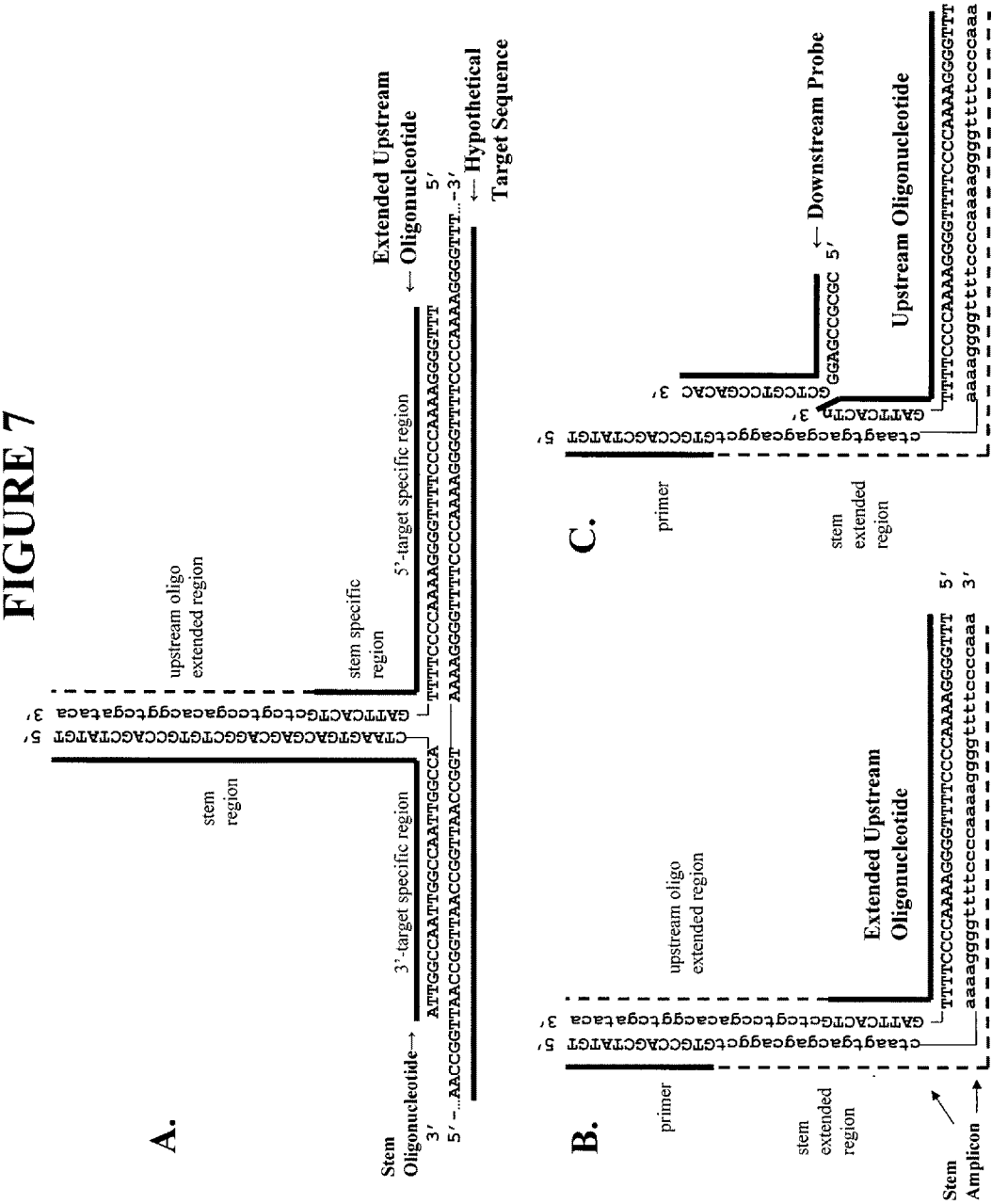
FIG. 7 shows one exemplary embodiment of a T-structure and polymerization methods that can be used to generate target dependent non-target amplification.

In other embodiments, the T-structure cleavage assays are combined with DNA polymerization. In certain embodiments, two T-structure oligonucleotides are designed to anneal to a target template and to each other to form a stem region composed of two annealed oligonucleotides of unequal length, such that the shorter of the two has a 3' end available for the addition of nucleotide bases by a nucleic acid polymerase, using the longer of the two stem forming oligos as the template for the extension reaction. This polymerization will create a new hybrid DNA molecule called an extended upstream oligonucleotide as shown in FIG. 7A. This new DNA molecule may then be detected directly by an invasive cleavage assay, such as the INVADER assay, or amplified to produce additional copies in order to increase the sensitivity and/or sensitivity of the detection assay (see FIG. 7B). As seen in FIG. 7B, a primer can be added that is complimentary to the newly created upstream oligo extended region. This primer can be extended as shown in FIG. 7B to create a stem amplicon sequence. In the presence of a plurality of primers and plural of upstream oligonucleotides, PCR could be conducted with the extended upstream oligonucleotide and stem amplicon serving as templates. The PCR process, or similar amplification process, could be conducted until the desired amount of stem amplicons and/or extended upstream oligonucleotides are created.

As can be seen in FIG. 7C, the stem amplicon sequence can act in the same manner as the stem oligonucleotide and serve as the target for forming an invasive cleavage reaction with a downstream probe and upstream oligonucleotide. The combination of PCR and invasive cleavage detection allows low levels of target nucleic acid to be detected. Of course, other methods besides invasive cleavage reactions can be used to detect the formation of stem amplicon sequences (e.g. radioactive base incorporation).

In one embodiment, oligonucleotide primers complimentary to two regions within the newly created extended upstream oligonucleotide can be used to create multiple copies of the stem region sequence, which can then be detected by an invasive cleavage assay. In some embodiments, the T-structure oligonucleotides, PCR primers, and invasive cleavage assay oligonucleotides are designed in such a way as to detect the opposite strand of the hybrid oligonucleotide that would be created in the first and subsequent cycles of PCR. This embodiment improves the specificity and sensitivity of the assay be demanding that both the first extension step, and at least one-cycle of sequence specific PCR occur to create the template that will be detected by the invasive cleavage assay. As above, this system may be further improved through the use of multiplexing several T-structure forming oligonucleotides, PCR primers, and invasive cleavage assays. Additional methods and compositions useful for combination with the T-structure invasive cleavage structure assays of the present invention are found in U.S. Pat. Nos. 5,424,413 and 5,451,503, both of which are herein incorporated by reference in their entireties as if fully set forth herein.

IV. Nucleic Acid Dispensing Using Non-Ionic Detergents

The present invention also provides methods, compositions, devices, and systems for consistent nucleic acid dispensing using non-ionic detergents. It has been found that the use of non-ionic detergents in nucleic acid mixtures improves the performance hydrophobic polymer dispensing tips and allows for improved accuracy and reproducibility, for example, in high throughput manufacture of microfluidic sample processing devices. In certain embodiments, the use of detergents in manufacturing solutions dramatically improves accuracy and increases manufacturing throughput where oligonucleotide assay components are disposed to components of microfluidic devices during manufacturing.

Increasing throughput of biological or chemical assays reduces reagent use, costs, and result waiting times. Often, assay throughput is increased through the use of multi-well plates or microfluidic devices with multiple process chambers. In some instances, microfluidic devices will be configured so as to enable one sample to be precisely distributed to a plurality of different process chambers where a separate assay or replicate assays may be performed simultaneously.

Manufacturing methods to improve such microfluidic devices often attempt to dispose one or more components of an assay into different regions of the device during manufacturing, so fewer assay components need to be added by the end user. In particular, when one sample is going to be distributed to multiple process chambers that must not become cross-contaminated with each other later, it is advantageous to dispose certain assay components directly into their process chamber location during the manufacture and assembly of the microfluidic device, rather than distribute them through the internal fluidic connections of the microfluidic device.

A common type of biological assay adapted to microfluidic devices is an oligonucleotide assay. These assays are useful for the detection of DNA or RNA, or other nucleic acids, through a variety of detection protocols, including PCR, OLA, TMA, INVADER Assay, and the like. Due to their relatively high stability and compatibility with dry conditions, oligonucleotide polymers such as primers and/or probes that take part in biological assays are often an ideal choice for predisposal into individual process arrays.

One method for predisposal of oligonucleotide components of a biological assay into a microfluidic device comprises adding a small volume of liquid containing oligonucleotide components to each process chamber in a component of a microfluidic device containing the process chambers that is subsequently assembled into the microfluidic device. To ensure against cross contamination of oligonucleotide components between process chambers, a multichannel liquid handling device may be used such that each process chamber corresponds to a separate liquid handling port or tip in the manufacturing system.

As an example, a 384-process chamber sample processing device may have oligonucleotide components disposed in each process chamber by the use of a 384 channel liquid handling device. Often, the liquids on these devices are handled through plastic tips. These tips are typically manufactured of hydrophobic plastic polymer materials, such as polypropylene.

Nucleic acids sometimes demonstrate a propensity to adhere to hydrophobic surfaces of this type. Because of this property, achieving a high level of accuracy of delivery of a precise concentration and volume of an oligonucleotide solution to multiple process chambers in a microfluidic device, or other device composed of wells, is difficult and costly. As throughput of manufacturing of these devices with predisposed oligonucleotide components is increased, these effects are magnified to the point that the oligonucleotide assays to be performed with the device are adversely affected. What is needed, then, is a method that enables large scale production of microfluidic devices, or other devices, containing predisposed oligonucleotide components with a high level of accuracy and reproducibility. Such methods are provided by the present invention.

In certain embodiments, a low percentage of a nonionic detergent is added to an oligonucleotide spotting solution. A preferred spotting solution contains the oligonucleotide components of an nucleic acid detection assay, and optionally a known quantity of a tracer dye to control for manufacturing variability.

In some embodiments, a tracer dye comprises a free label present at a known concentration. In some embodiments this free label comprises a fluorophore. In some other embodiments, the tracer dye comprises a short oligonucleotide of known sequence that is linked to a label and present at a known concentration. In some other embodiments, the tracer dye comprises a mixture of both free label and oligonucleotide-linked label, both of which are present at known concentrations.

The present invention is not limited by the non-ionic detergent employed. Suitable non-ionic detergents can be found by screening candidate non-ionic detergents using the methods described in Example 8 by substituting in the candidate non-ionic detergent for those recited in Example 8. Examples of non-ionic detergents that may be employed, include, but are not limited to: polyoxyethylene surfactants, carboxylic ester surfactants, carboxylic amide surfactants, n-dodecanoylsucrose, n-dodecyl-β-D-glucopyranoside, n-octyl-β-D-maltopyranoside, n-octyl-β-D-thioglucopyranise, n-decanoylsucrose, n-decyl-β-D-maltopyranoside, n-decyl-β-D thiomaltoside, n-heptyl-β-D-glucopyranoside, n-heptyl-β-D-thioglucopyranoside, n-hexyl-β-D-glucopyranoside, n-nonyl-β-D-glucopyranoside, n-octanoylsucrose, n-octyl-β-D-glucopyranoside, cyclohexyl-n-hexyl-β-D-maltoside, cyclohexyl-n-methyl-β-D-maltoside, digitonin, and those available under the trade designations PLURONIC, TRITON, TWEEN, as well as numerous others. Without limitation, certain preferred surfactants of the present invention are the hydroxyethoxy ethers, such as TWEEN.

In some embodiments of the invention, the concentration of the nonionic detergent makes up less than 1% of solution by volume of the nucleic acid mixture. In certain embodiments, the concentration of the nonionic detergent makes up between 0.001 and 0.1% of the solution by volume of the nucleic acid mixture. In other embodiments, the nonionic detergent is present in the nucleic acid mixture spotting solution at a concentration of 0.005% by volume.

In certain embodiments, the nucleic acid mixture with the non-ionic detergent is dispensed into the wells of a microfluidic sample device or component thereof. Numerous microfluidic sample processing devices are known in the art. Examples of such devices, and methods for making and using such devices, are described in the following patents and applications: U.S. Pat. Nos. 6,627,159; 6,720,187; 6,734,401; 6,814,935; U.S. Application 2002/0064885; and U.S. Application 2003/0152994; all of which are herein incorporated by reference for all purposes.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); and ° C. (degrees Centigrade).

Example 1

Qualitative Detection of Low Copy Numbers of Viral RNA

This example describes the qualitative detection of low copy number of viral RNA employing extended rounds of PCR and two INVADER assays that detect different parts of the viral RNA, but report to the same FRET cassette. Oligonucleotides were prepared and mixed as follows. Forward and reverse primers for a first viral target region and a second viral target region were generated, as well as forward and reverse primers for the universal internal control (UIC). All of the reverse primers were designed to also serves as INVADER oligonucleotides for their respective target regions. All of these primers were provided at a final concentration of 0.5 uM. Primary probes for the first and second viral target regions were generated, with each probe containing a 3' portion specific for either the first or second viral target region, and 5' flaps that were identical as designed to hybridize to a first FRET cassette (labeled with FAM) provided in the oligonucleotide mixture. A primary probe specific for the UIC was also generated that contained a 3' region specific for the UIC control, and a 5' region that reported a second FRET cassette (labeled with Yellow dye). All of the primary probes were provided at a final concentration of 0.667 uM and both FRET cassettes were provided at a final concentration of 0.25 uM.

The enzyme mixture was prepared as follows: 13.36 ng/µL Cleavase® VIII, 0.034 Units/µL native Taq DNA polymerase (Promega), 2 Units/µL MMLV RT (Promega), 0.1 mM DTT. The enzyme mix, target nucleic acid, 20 ng/µL tRNA, and oligonucleotides were mixed in Cleavase® dilution buffer (20 mM Tris pH 8.0, 50 mM KCl, 0.5% Tween 20, 0.5% Nonidet P40, 50% glycerol, 0.1 mg/ml BSA). The reactions were performed in a buffer containing 10 mM MOPS, 7.5 mM MgCl2, and 25 µM dNTPs. Universal internal control template (5'-CCCUGCAACGCGAGUGCUGAGGCUGGU-GUACGACCCAUCGCU CGCCCGCUACCGCGACGUC-CUGCCGCACUCUAGGUACGUGGUCCAC-3', SEQ ID NO:5) was present at 150 copies per reaction, or omitted, as shown in the results. Viral template RNA was prepared by extraction of virion (Acrometrix) RNA with the high pure RNA extraction kit (Roche) according to the manufacturer's instructions, and added to the reaction mixture at concentrations ranging from 2.06 to 500 copies per reaction, as shown in the results. All the aforementioned reagents were mixed into 25 µL reactions, and subjected to temperature incubations as follows: 42° C. for 30 min, 95° C. for 2.5 min, 35 cycles at (95° C. for 20 sec and 72° C. for 1 min), 99° C. for 10 min, and 58° C. for 30 min. The fluorescent signal produced in each reaction vessel was quantitated on a Tecan Genios FL fluorescence plate reader.

As shown in FIG. 1, the above assay was able to detect viral RNA template present in the reaction vessel when present at approximately 2 copies per reaction. The UIC was detected at approximately equivalent levels in each reaction, with some minor fluorescent signal cross-talk apparent in the reactions containing the highest levels of target template. This Example demonstrates how hard to detect viral RNA sequence, present at very low levels, can be detected by amplifying two regions of the viral RNA with extended rounds of PCR and detecting each target region with an invasive cleavage assay that reports to the same readout channel (e.g. same FRET cassette).

Example 2

Quantitative Detection of a Broad Range of Copy Numbers of Viral RNA

The following example describes the use of two probes at different concentrations that each contributes to extend the dynamic range of detection of a viral RNA target sequence using a single dye for detection. In this example, a different FRET cassette was provided to accumulate signal from each probe, but the FRET cassettes reported using the same dye.

Oligonucleotides were prepared and mixed in three different pools: "1×", "0.01×", and "1×+0.01×". The following oligonucleotides were used. Forward and reverse primers for a particular viral target region were generated, as well as forward and reverse primers for the universal internal control (UIC). All of the reverse primers were designed to also serves as INVADER oligonucleotides for their respective target regions. All of these primers were provided at a final concentration of 0.5 uM. First and second primary probes were generated having identical 3' regions specific for the target viral RNA and 5' flaps that were different. The flaps were designed to hybridize to different FRETs (first and second FRETs), but the FRETs were designed with the same dye (red dye). A third primary probe specific for the UIC was also generated that contained a 3' region specific for the UIC control, and a 5' region that reported a third FRET cassette (labeled with Yellow dye). The first and second primary probes were provided at different concentrations. The first primary probe was provided at a final concentration of 0.667 uM and the second primary probe was provided at a final concentration that was 100-fold lower (i.e. 0.0067 uM). The third primary probe was provided at the standard concentration of 0.667 uM. All of the FRET cassettes were provided at a final concentration of 0.25 uM.

The enzyme mixture for this example was prepared as follows: 13.36 ng/μL Cleavase® VIII, 0.034 Units/μL native Taq DNA polymerase (Promega), 2 Units/μL MMLV RT (Promega), 0.1 mM DTT. The enzyme mix, target nucleic acid, 20 ng/μL tRNA, and oligonucleotides were mixed in Cleavase® dilution buffer (20 mM Tris pH 8.0, 50 mM KCl, 0.5% Tween 20, 0.5% Nonidet P40, 50% glycerol, 0.1 mg/ml BSA). The reactions were performed in a buffer containing 10 mM MOPS, 7.5 mM MgCl2, and 25 μM dNTPs. Universal internal control template (SEQ ID NO:5) was present at 66.7 copies per reaction, or omitted, as shown in the results. Viral template RNA was prepared by extraction of virion (Acrometrix) RNA with the high pure RNA extraction kit (Roche) according to the manufacturer's instructions and added to the reaction mixture at concentrations ranging from 50 to 160,000,000 copies per reaction, as shown in the results. All the aforementioned reagents were mixed into 50 μL reactions, and subjected to temperature incubations as follows: 42° C. for 30 min, 95° C. for 2.5 min, 25 cycles at (95° C. for 20 sec and 72° C. for 1 min), 99° C. for 10 min, and 58° C. for 30 min. The fluorescent signal produced in each reaction vessel was quantitated on a Tecan Genios FL fluorescence plate reader.

As shown in FIG. 2, the assay was able to detect viral RNA in a linear dynamic range from 50 to 8,000,000 copies, when the "1×+0.01×" oligonucleotide mixture was used. The "1×" and "0.01×" lines depict the signal generated when the "1×" or "0.01×" oligonucleotide mixtures were used independently. This experiment demonstrates using multiple probes at different concentrations is one way to increase dynamic range when detecting viral RNA.

Example 3

Detecting Two Different Types of Viral Nucleic Acid in Single Reaction Vessel Using Invasive Cleavage Assays that Report to Different Dyes This Example describes detecting two different types of viral nucleic acid in a single reaction vessel using invasive cleavage assays that report different colors.

Oligonucleotides were prepared and mixed as follows. Forward and reverse primers for a first viral target RNA sequence and a second viral target DNA sequence, with the second viral target being a viral nucleic acid sequence from a different type of virus than the first viral target sequence, were generated. Both of the reverse primers were designed to also serves as INVADER oligonucleotides for their respective targets. All of these primers were provided at a final concentration of 1.0 uM. Primary probes for the first and second viral target sequences were generated, with each probe containing a 3' portion specific for either the first or second viral target sequence, and 5' flaps that were different from each other and designed to different FRET cassettes. Both primary probes were provided at a final concentration of 0.667 uM. The two FRET cassettes were also provided in the oligonucleotide mixture and were labeled differently, with the first FRET cassette having a FAM dye and the second FRET cassette having a Red dye. Both FRET cassettes were provided at a final concentration of 0.334 uM.

The enzyme mixture was prepared as follows: 6.7 ng/μL Cleavase® VIII, 0.02 Units/μL native Taq DNA polymerase (Promega), 2 Units/μL MMLV RT (Promega). The enzyme mix, target nucleic acid, 20 ng/μL tRNA, and oligonucleotides were mixed in reactions performed in a buffer containing 10 mM MOPS, 7.5 mM MgCl$_2$, and 25 μM dNTPs. The first viral target sequence template RNA was prepared by extraction of virion (Acrometrix) RNA with the high pure RNA extraction kit (Roche) according to the manufacturer's instructions and added to the reaction mixture at concentrations ranging from approximately 2 to 62 copies per reaction, as shown in the results. The second viral target sequence template DNA extracted from virion (Advanced Biotechnologies) was added to the reaction mixture at concentrations ranging from approximately 35 to 1116 copies per reaction, as shown in the results. All the aforementioned reagents were mixed into 100 μL reactions, and subjected to temperature incubations as follows: 42° C. for 30 min, 95° C. for 5 min, 28 cycles at (95° C. for 45 sec, 69.5° C. for 45 sec and 72° C. for 90 sec), 99° C. for 10 min, and 58° C. for 15 min. The fluorescent signal produced in each reaction vessel was quantitated on a Tecan Genios FL fluorescence plate reader.

Figure 3:
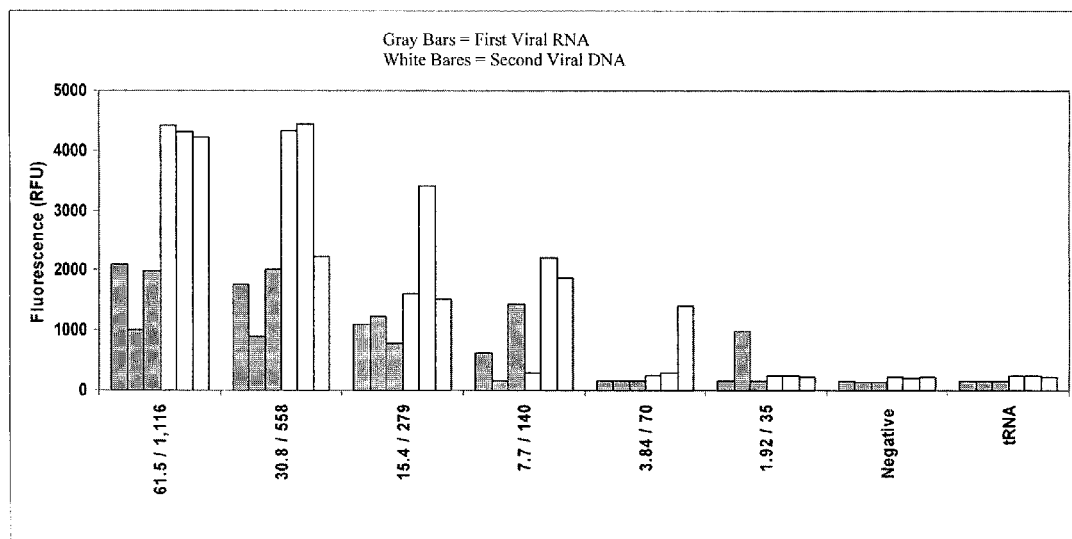
FIG. 3 shows the results of Example 3, which describe the simultaneous detection of a first virus-derived target RNA and second virus-derived target DNA with distinguishing fluorescent signals directed to the FAM and Red fluorescent channels, respectively.

As shown in FIG. 3, first virus-derived target RNA and second virus-derived target DNA were simultaneously detected in the same reaction vessel using the methods described in this Example, with distinguishing fluorescent signal directed to the FAM and Red fluorescent channels, respectively.

Example 4

Detecting Two Different Types of Viral Nucleic Acid in Single Reaction Vessel Using Invasive Cleavage Assays that Report to the Same Dye This Example describes detecting two different types of viral nucleic acid in a single reaction vessel using invasive cleavage assays that report to the same dye. Oligonucleotides were prepared and mixed as follows. Forward and reverse primers for a first viral target RNA sequence and a second viral target DNA sequence, with the second viral target being a viral nucleic acid sequence from a different type of virus than the first viral target sequence, were generated. Both of the reverse primers were designed to also serves as INVADER oligonucleotides for their respective targets. All of these primers were provided at a final concentration of 1.0 uM. Primary probes for the first and second viral target sequences were generated, with each probe containing a 3' portion specific for either the first or second viral target sequence, and 5' flaps that were different from each other and designed to different FRET cassettes. Both primary probes were provided at a final concentration of 0.667 uM. The two FRET cassettes were also provided in the oligonucleotide mixture and were labeled with the same dye (both with FAM dye). Both FRET cassettes were provided at a final concentration of 0.334 uM.

The enzyme mixture was prepared as follows: 6.7 ng/μL Cleavase® VIII, 0.02 Units/μL native Taq DNA polymerase (Promega), 2 Units/μL MMLV RT (Promega). The enzyme mix, target nucleic acid, 20 ng/μL tRNA, and oligonucleotides were mixed in reactions performed in a buffer containing 10 mM MOPS, 7.5 mM MgCl2, and 25 μM dNTPs. First viral template RNA was prepared by extraction of virion (Acrometrix) RNA with the high pure RNA extraction kit (Roche) according to the manufacturer's instructions and added to the reaction mixture at concentrations ranging from approximately 2 to 62 copies per reaction, as shown in the results. Second viral template DNA was extracted from virion (Advanced Biotechnologies) and was added to the reaction mixture at concentrations ranging from approximately 35 to 1116 copies per reaction, as shown in the results. All the aforementioned reagents were mixed into 100 μL reactions, and subjected to temperature incubations as follows: 42° C.

for 30 min, 95° C. for 5 min, 28 cycles at (95° C. for 45 sec, 69.5° C. for 45 sec and 72° C. for 90 sec), 99° C. for 10 min, and 58° C. for 15 min. The fluorescent signal produced in each reaction vessel was quantitated on a Tecan Genios FL fluorescence plate reader.

Figure 4:
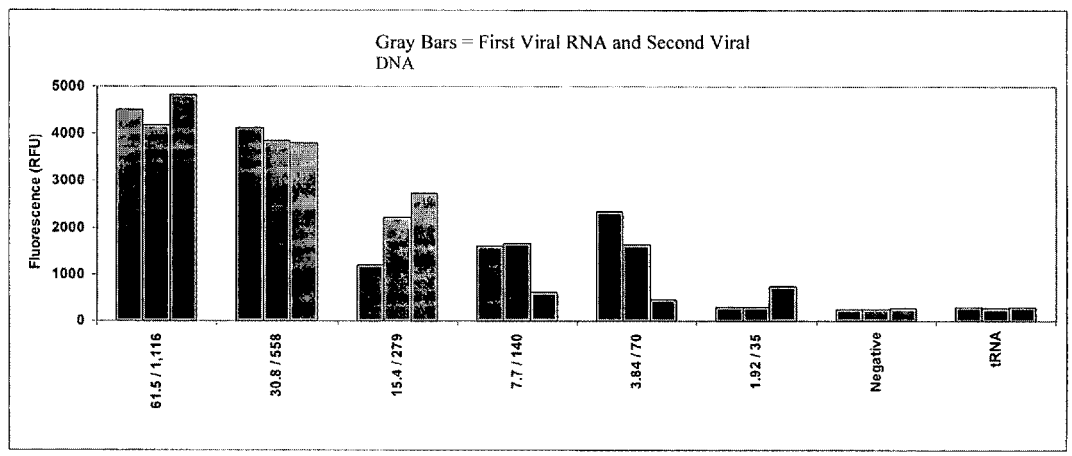
FIG. 4 shows the results of Example 4, which describe the simultaneous detection of a first virus-derived target RNA and second virus-derived target DNA with both assays reporting to the same fluorescent dye.

As shown in FIG. 4, first virus-derived target RNA and second virus-derived target DNA were simultaneously detected in the same reaction vessel using the methods described in this Example, with detection signal reported to the same fluorescent channel.

Example 5

Detection of Viral RNA Using Multiple Stem Oligonucleotides

This example describes the use of stem oligonucleotides to detect viral RNA directly using the INVADER assay. Combining the stem oligonucleotides with the downstream probe and upstream oligonucleotide allows a T-structure to form as shown with the hypothetical sequences in FIG. 6. This allows a "T-structure INVADER assay" to be performed.

In this example, three sets of oligonucleotides were designed that each anneal to specific regions of the same viral RNA genome. The three regions of the target viral RNA were designated Region 1, Region 5, and Region 8. Each stem oligonucleotide contained the same probe annealing region so that each INVADER cleavage structure would release the same probe flap upon cleavage by CLEAVASE and could be detected by a single secondary FRET cassette containing oligonucleotide. In this example, each of the sets was used separately, and two of the stem oligonucleotide sets were used simultaneously.

The T-structure INVADER assay was used to detect both purified viral RNA and viral RNA from an viral RNA-positive serum sample. The T-structure INVADER assay reactions were set up as follows: In a 96-well plate, to a 10 uL sample was added 5 uL of 4× CLEAVASE buffer (containing 40 mM MOPS Buffer and 56 mM MgCl$_2$), 4 uL of 5× oligonucleotide mixture (containing 2.5 uM downstream probe oligonucleotide, 1 nM upstream (INVADER) oligonucleotide, 1 nM Stem oligonucleotide, and 1.25 uM FRET cassette oligonucleotide), and 1 uL of Cleavase X (at 40 ng/uL). This mixture was incubated at 75° C. for 5 minutes, then at 63° C. for 4 hours. Following this incubation, fluorescent signal from the reaction was detected in a microplate fluorimeter.

The upstream oligonucleotides were blocked on their 5' ends with 2'-O-methylated bases, while the stem oligonucleotides were blocked on both their 5' and 3' ends with 2'-O-methylated bases. Three different regions on the same viral RNA target sequence were detected. For each of the three targets, a particular stem oligonucleotide and particular upstream oligonucleotide were employed, while all three targets employed the same downstream probe. In regard to the three stem oligonucleotides, each of these oligonucleotides had a particular 3' target specific region, and a particular stem region, where the stem region was configured to hybridize to the hybridize to a portion of both the upstream oligonucleotide and the downstream probe. In regard to the three upstream oligonucleotides, each of these had a 5' target specific region, a stem specific region configured to hybridize to a portion of the stem region of the stem oligonucleotide, and a 3' region (one base in this example) configured to not hybridize to the stem oligonucleotide. The general T-structure configuration formed by the combination of these sequences at each target site is shown schematically in FIG. 6 (which shows a hypothetical target sequence).

In this Example, Invader/Stem/Probe assays for regions 1 and 8 were tested separately and together to detect purified viral RNA and viral RNA from viral RNA-positive plasma. The results are shown below in Tables 1 and 2.

TABLE 1

Viral RNA Transcripts
4 hr incubation:

|  | Copy number in assay | Site 1 | Site 8 | Site 1 + Site 8 |
|---|---|---|---|---|
| Raw | No Target Control | 354 | 350 | 363 |
| Signal | 50000 | 4341 | 4496 | 4405 |
| Count | 18000 | 1058 | 1439 | 1889 |
|  | 6000 | 630 | 753 | 968 |
|  | 2000 | 449 | 502 | 574 |
|  | 1000 | 399 | 458 | 492 |
|  | 500 | 392 | 434 | 445 |
| Signal | 50000 | 12.26 | 12.85 | 12.13 |
| Fold | 18000 | 2.99 | 4.11 | 5.20 |
| Over | 6000 | 1.78 | 2.15 | 2.67 |
| Control | 2000 | 1.27 | 1.43 | 1.58 |
|  | 1000 | 1.13 | 1.31 | 1.36 |
|  | 500 | 1.11 | 1.24 | 1.23 |

TABLE 2

Viral RNA extracted from viral-positive plasma
4 hr incubation:

|  | Copy number in assay | Site 1 | Site 8 | Site 1 + Site 8 |
|---|---|---|---|---|
| Raw | Negative Plasma | 357 | 369 | 366 |
| Signal | 140000 | 2643 | 3007 | 3687 |
| Count | 42000 | 1466 | 1492 | 2235 |
|  | 14000 | 719 | 747 | 1092 |
|  | 4200 | 482 | 509 | 629 |
|  | 1400 | 414 | 433 | 468 |
| Signal | 140000 | 7.40 | 8.15 | 10.07 |
| Fold | 42000 | 4.11 | 4.04 | 6.11 |
| Over | 14000 | 2.01 | 2.02 | 2.98 |
| Control | 4200 | 1.35 | 1.38 | 1.72 |
|  | 1400 | 1.16 | 1.17 | 1.28 |

Results for the T-structure INVADER assay for region 5 are shown below in Table 3.

TABLE 3

|  | Copy number in assay | 4 hr incubation |
|---|---|---|
| Raw | No Target Control | 310 |
| Signal | 18000 | 1006 |
| Count | 6000 | 522 |
|  | 2000 | 571 |
| Signal | 18000 | 3.25 |
| Fold Over | 6000 | 1.68 |
| Control | 2000 | 1.84 |

Example 6

Optimization of Oligonucleotide Concentration

In this Example, oligonucleotide concentrations were optimized for use in the T-structure INVADER assay. Reactions were set up as in Example 5 above, but Region 1 upstream (INVADER) and Stem oligonucleotide concentrations were varied from 50 nM to 1 pM. 50,000 copies of viral RNA transcripts were used as the template. Results are shown below in Table 4.

TABLE 4

|  |  | 50 nM | 5 nM | 0.1 nM | 1 pM |
|---|---|---|---|---|---|
| Raw Signal Count | No Target Control | 4492 | 1554 | 310 | 296 |
|  | target transcript | 4872 | 2692 | 471 | 300 |
| Signal Fold Over Control | target transcript | 1.08 | 1.73 | 1.52 | 1.01 |

Example 7

Optimization of Length of Stem Specific Region of Upstream Oligonucleotide

In this Example, the length of the upstream (INVADER) oligonucleotide, and particularly the stem specific region of the upstream oligonucleotide, was optimized for use in the T-structure INVADER assay. The experiments were performed as above, using viral RNA transcripts as the template, with the exception that the INVADER reaction was incubated for 6 hours. Upstream oligonucleotides with 5 base, 9 base, and 12 base stem specific regions were tested. As shown in Table 5 below, upstream oligonucleotides with t9 base stem specific regions performed better than the 5 base and 12 base stem specific regions.

TABLE 5

|  | Copy number in assay | 5 bases | 9 bases | 12 bases |
|---|---|---|---|---|
| Raw Signal Count | No Target Control | 297 | 320 | 380 |
|  | 24,000 | 347 | 518 | 486 |
|  | 8,000 | 302 | 441 | 470 |
| Signal Fold Over Control | 24,000 | 1.17 | 1.62 | 1.28 |
|  | 8,000 | 1.02 | 1.38 | 1.24 |

Example 8

Use of Nonionic Detergent to Increase Accuracy of Oligonucleotide Spotting

The following example describes the use of nonionic detergent to increase the reproducibility and accuracy of spotting of oligonucleotide assay components on a microfluidic device component.

In this example, oligonucleotide components of an oligonucleotide detection assay are added to a sheet of molded plastic that contains the device process chambers which will later be manufactured into a 384-well microfluidic device after adhesion to a metal foil backing. In order to control for manufacturing variability, certain spots in each device include a synthetic "tracer dye" which is composed of red fluorophore covalently linked to an oligonucleotide dT10 molecule. Certain spots in each device also contain a free green fluorophore as an alternative means of manufacturing control. The fluorescence of the red tracer dye, as an indicator of the quantity of tracer added to each device, correlates closely with the performance of the oligonucleotide detection assay in downstream applications.

The final concentration of the components of the oligonucleotide spotting solutions in this Example were as follows: 17 mM MOPS (3-(N-morpholino) propanesulfonic acid), 240 nM of oligonucleotide tracer dye, and 10 ng/mL free fluorophore.

Figure 8A:
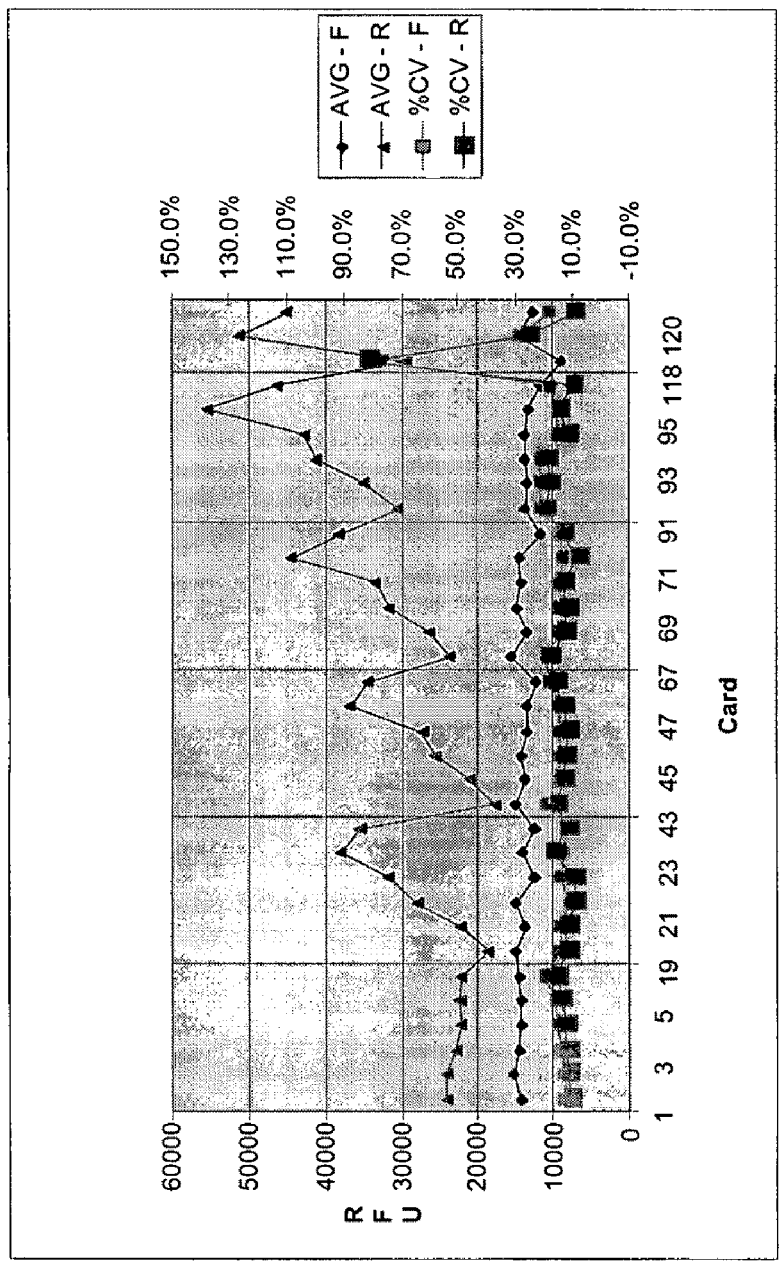
FIG. 8 shows the results of a 120 microfluidic card dispensing run using NanoScreen pipette tips (FIG. 8A) or Beckman pipette tips (FIG. 8B), without also using non-ionic detergent in the nucleic acid mixture.

In the context of high-throughput manufacturing, an unacceptable level of device-to-device variability resulted (FIG. 8A). In this manufacturing protocol, a 384-tip liquid handling robot, using NanoScreen Tips, aspirates sufficient volume from a master plate to add 1 uL per spot to each of 24 microfluidic devices in series. This cycle of 24 devices is repeated 5 times, with 5 aspiration steps from the same master plate, for spotting of a total of 120 devices in each manufacturing run. As shown in FIG. 8A, the fluorescent signal detected from the Red tracer dye increases significantly towards the first and last devices of each cycle of 24, with the magnitude of this cyclical trend itself increasing with each subsequent round of 24 devices up to 120. It is also noteworthy that the signal from the green free fluorophore, which serves as an indicator of the total volume added to each spot, was more or less consistent throughout the application, while the signal from the red oligonucleotide tracer dye, which serves as an indicator of the actual concentration of dye added to each spot, showed a high degree of variability (FIG. 8A). This suggested that the source of the increasing variability was associated with a change in the actual concentration of the oligonucleotide components being added to each spot in series. Although the reason for the change in concentration over time is not known, one possibility is that the oligonucleotide components were adhering to the polypropylene materials used in the tips of the liquid handling device, which would in turn affect the actual concentration of oligonucleotide tracer being added to each spot during manufacturing.

Figure 8B:
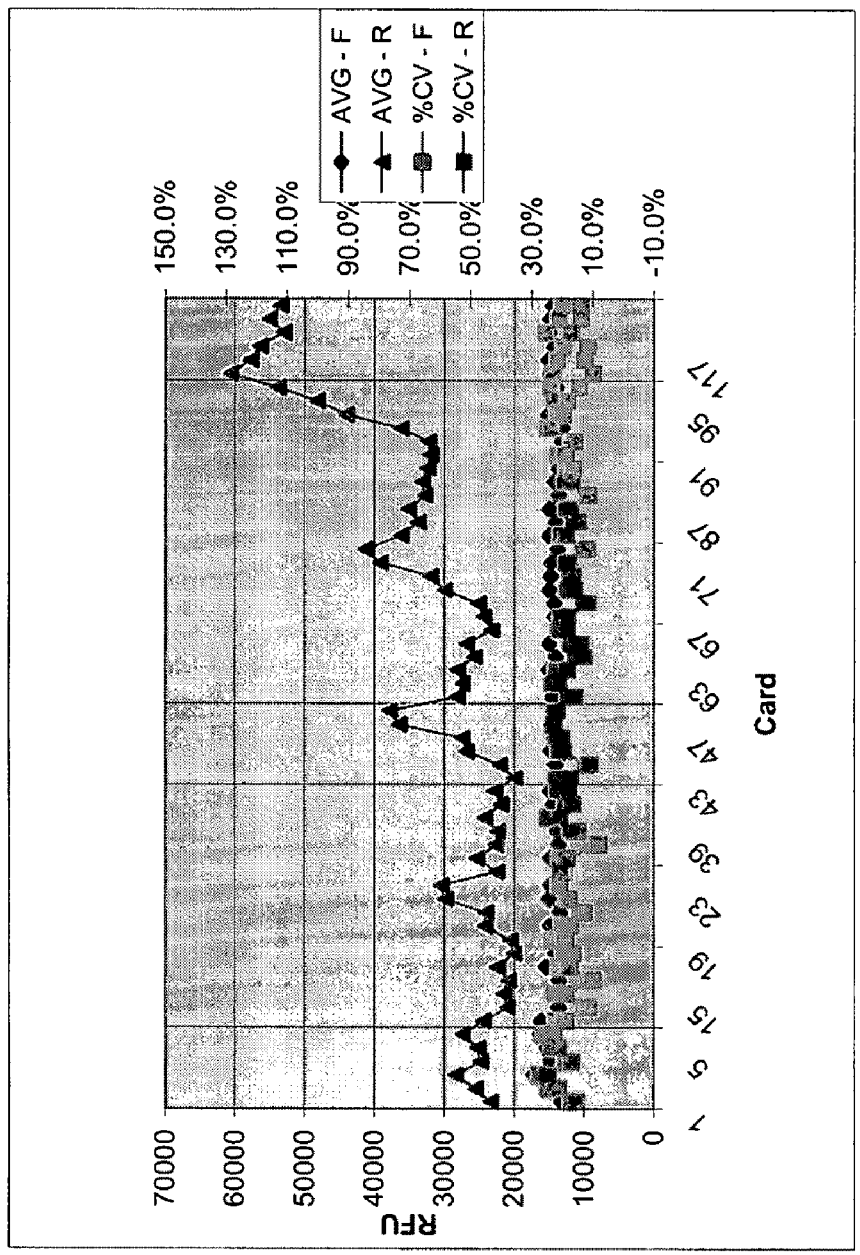

First, two varieties of liquid handling tips, NanoScreen tips and Beckman tips, both made from similar polymer materials, were tested. The results of this experiment demonstrated that the problem of spotting variability were not associated with the peculiarities of any single type of liquid handling type, but rather more generally to the properties of the materials the liquid handling tips are produced from. FIG. 8A shows the results using NanoScreen tips and FIG. 8B shows the results using Beckman tips.

Figure 9:
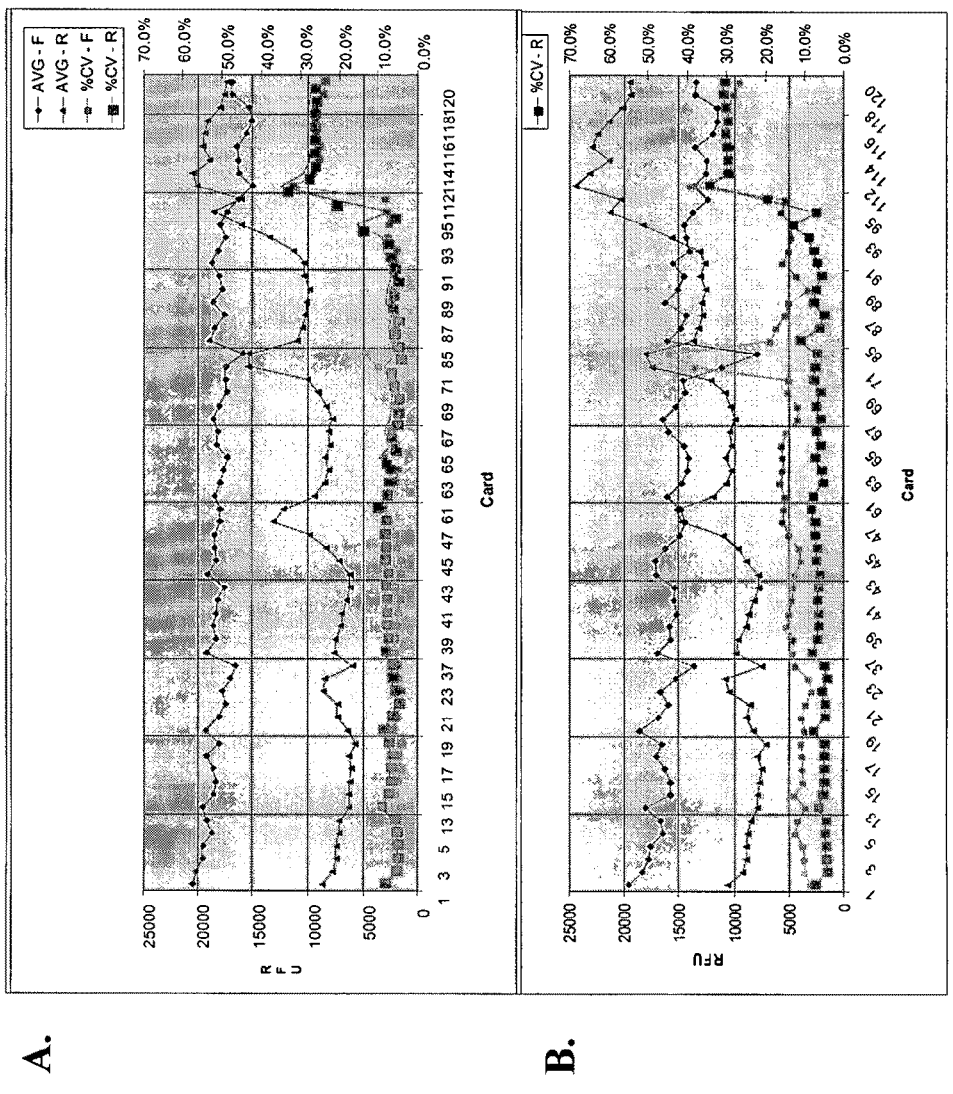
FIG. 9 shows the result of a 120 microfluidic card dispensing run with Beckman pipette tips using either a water diluent (FIG. 9A) or tRNA (FIG. 9B) in the nucleic acid mixture, without also using a non-ionic detergent.

Two hypothesis were tested to determine whether additional materials added to the spotting solution could solve the problems of spotting variability. In the first, transfer RNA (tRNA) was used. It is well known in the art of oligonucleotide properties that mixtures of additional nucleic acids can often serve to "block" the nonspecific binding of the desired oligonucleotides to a variety of surfaces. One common type of blocking nucleic acid used is a preparation of tRNA molecules commonly available for this purpose. A solution of Brewer's Yeast tRNA at a final concentration of 94 µg/mL was added to the oligonucleotide spotting mixture, and the same type of 120 plate cycle (5 runs with 24 plates spotted in each run) was run as described above with free fluor and red tracer. The results are shown in FIGS. 9B (with the added tRNA) and 9A (control containing a water diluent instead of tRNa). The results of this experiment indicated that the use of blocking nucleic acids would not function to prevent spotting variability in generating pre-loaded microfluidic devices.

Figure 10:
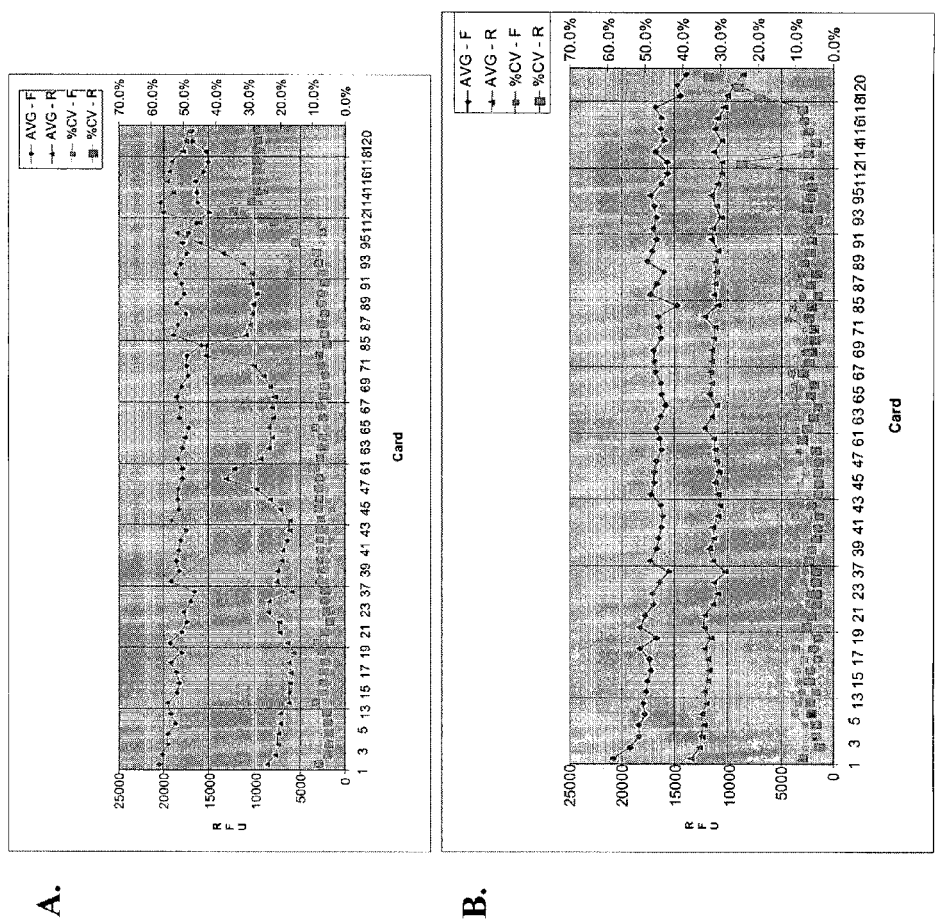
FIG. 10 shows the result of a 120 microfluidic card dispensing run with Beckman tips using either a water diluent (FIG. 10A) or water plus 0.25% TWEEN 20 and 0.25% Nonident P40 (FIG. 10B).

A second set of assays were conducted to test the effect of nonionic detergents on spotting variability. In the first experiments, two nonionic detergents (Tween-20 and Nonidet P40, a.k.a. NP40) were tested in the context of the oligonucleotide spotting solution. As shown in FIG. 10B, the incorporation of the nonionic detergents led to the complete diminution of the problem of spotting variability in manufacturing of pre-loaded microfluidic devices. FIG. 10A shows a control that used a water diluent and no non-ionic detergents.

Figure 11A:
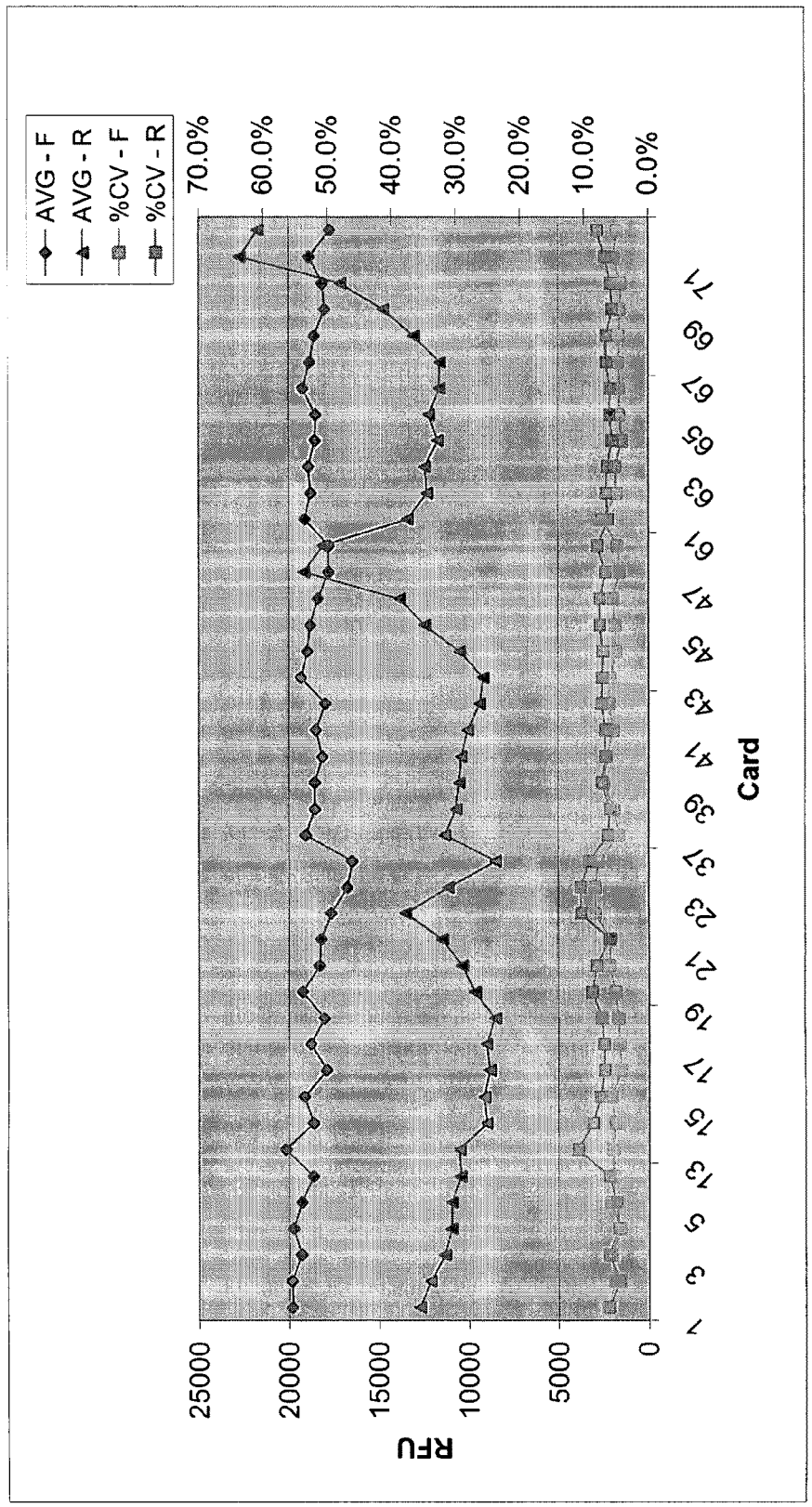
FIG. 11 shows the result of a 72 microfluidic card dispensing run with Beckman pipette tips using either a standard water diluent solution (FIG. 11B), water diluent plus 0.25% TWEEN (FIG. 11B), water diluent plus 0.005% TWEEN (FIG. 11C), and water diluent plus 0.0025% TWEEN (FIG. 11D).
Figure 11B:
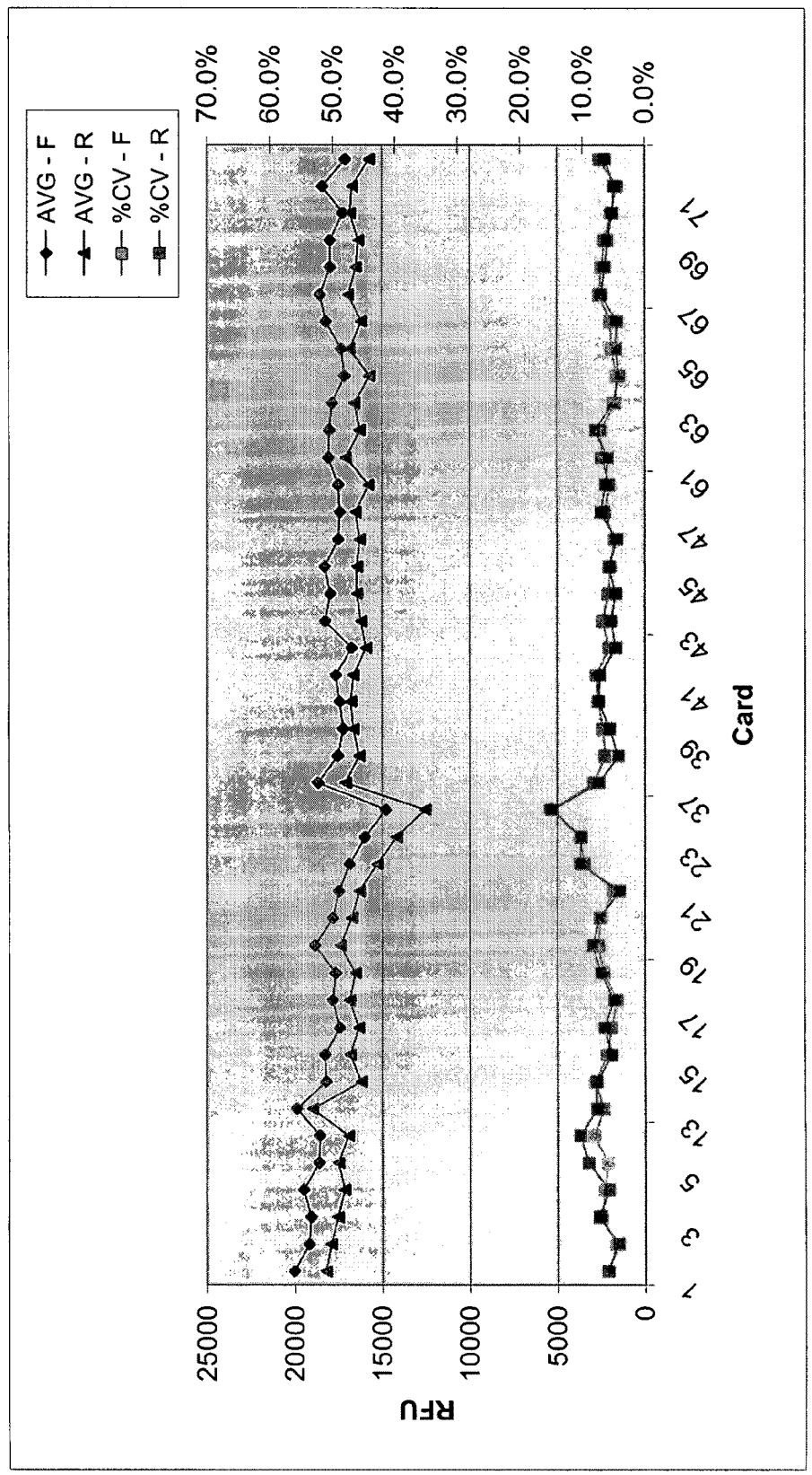
Figure 11C:
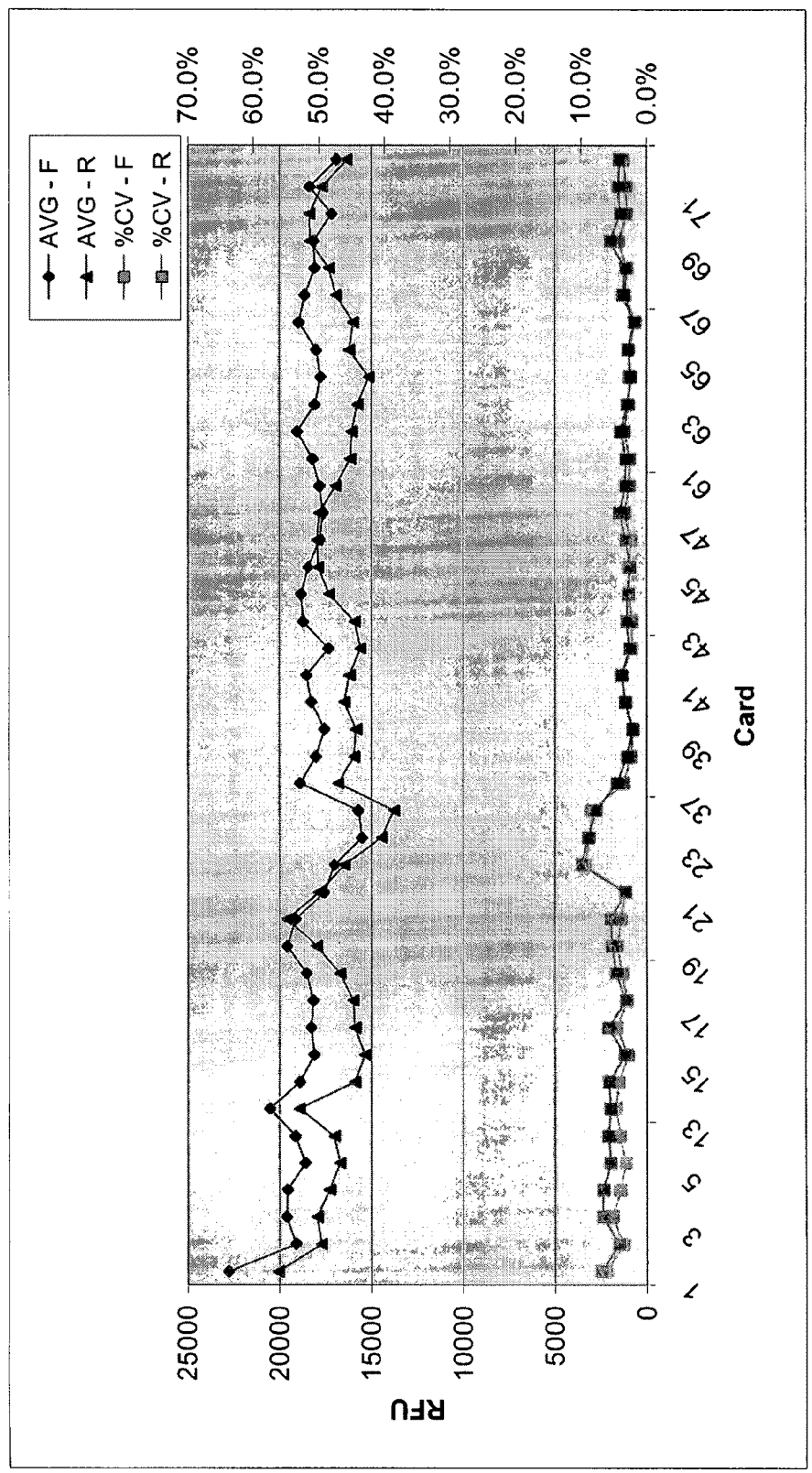
Figure 11D:
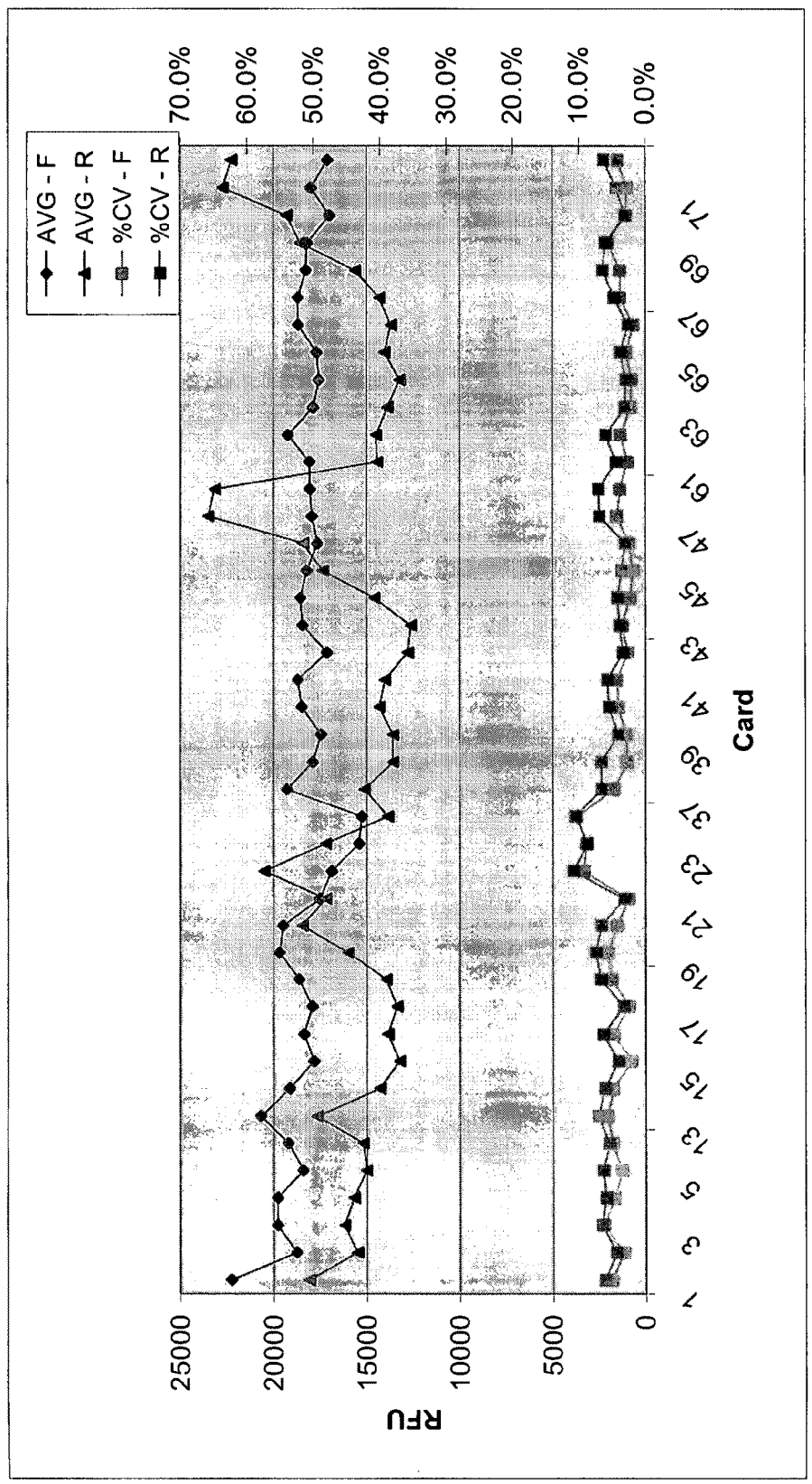

The contribution and minimum concentration of each nonionic detergent was subsequently tested. Both Tween-20 and NP40 worked equally well in this system. FIG. 11A shows a control using water; FIG. 11B shows the results using 0.25% TWEEN; FIG. 11C shows the results using 0.005% TWEEN;

and FIG. 11D shows the results using 0.0025% TWEEN. As shown in these figures, the minimum concentration of nonionic detergent required to provide consistent spotting performance was around 0.005%. These results demonstrate that the use of nonionic detergent in the oligonucleotide spotting mixture helps eliminate spotting variability problems associated with high throughput microfluidic device manufacturing.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in the relevant arts are intended to be within the scope of the following claims.

We claim:

1. A method of target nucleic acid dependent amplification of a non-target sequence in a sample comprising;
   a) incubating a sample with stem oligonucleotides, upstream oligonucleotides, primers, dNTPs, and a polymerase under conditions such that, if a target nucleic acid is present:
      i) a 3' target specific region of said stem oligonucleotides hybridizes to said target nucleic acid, and a stem region of said stem oligonucleotides remains available for hybridization to said upstream oligonucleotides,
      ii) a 5' target specific region of said upstream oligonucleotides hybridizes to said target nucleic acid, and a stem specific region of said upstream oligonucleotides hybridizes to a portion of said stem region of said stem oligonucleotides, and
      iii) said polymerase extends a 3' end of said upstream oligonucleotides using said stem region of said stem oligonucleotides as a template to generate extended upstream oligonucleotides that comprise an upstream oligonucleotide extended region;
   b) heating said sample to separate said extended upstream oligonucleotides from said stem oligonucleotides and said target nucleic acid;
   c) cooling said sample under conditions such that said primers hybridize to at least a portion of said upstream oligonucleotide extended region of said extended upstream oligonucleotides; and
   d) incubating said sample under conditions such that said primers are extended by said polymerase using said extended upstream oligonucleotides as templates such that stem amplicon sequences are generated.

2. The method of claim 1, further comprising the step of detecting the presence or absence of said target nucleic acid in said sample by determining if stem amplicon sequences are generated.

3. The method of claim 1, further comprising the step of performing one or more rounds of PCR using said stem amplicon sequences and said extended upstream oligonucleotides as templates, wherein said upstream oligonucleotides prime polymerization from said stem amplicon sequences, and wherein said primers prime polymerization from said extended upstream oligonucleotides.

4. The method of claim 3, further comprising a step of detecting the presence or absence of said target nucleic acid in said sample by detecting an accumulated PCR product.

5. The method of claim 1, further comprising incubating said sample with downstream probes and upstream oligonucleotides such that invasive cleavage structures are formed with said stem amplicon sequences, the downstream probes, and the upstream oligonucleotides.

6. A method comprising:
   1) incubating a sample with stem oligonucleotides, upstream oligonucleotides, primers, dNTPs, and a polymerase under conditions such that, if a target nucleic acid is present:
      A) a 3' target specific region of said stem oligonucleotides hybridizes to said target nucleic acid, and a stem region of said stem oligonucleotides remains available for hybridization to said upstream oligonucleotides,
      B) a 5' target specific region of said upstream oligonucleotides hybridizes to said target nucleic acid, and a stem specific region of said upstream oligonucleotides hybridizes to a portion of said stem region of said stem oligonucleotides, and
      C) said polymerase extends a 3' end of said upstream oligonucleotides using said stem region of said stem oligonucleotides as a template to generate extended upstream oligonucleotides that comprise an upstream oligonucleotide extended region;
   2) heating said sample to separate said extended upstream oligonucleotides from said stem oligonucleotides and said target nucleic acid; and
   3) cooling said sample under conditions such that said primers hybridize to at least a portion of said upstream oligonucleotide extended region of said extended upstream oligonucleotides.

7. The method of claim 6, further comprising the step of incubating said sample under conditions such that said primers are extended by said polymerase using said extended upstream oligonucleotides as templates such that stem amplicon sequences are generated.

8. The method of claim 7, further comprising the step of detecting the presence or absence of said target nucleic acid in said sample by determining if stem amplicon sequences are generated.

9. The method of claim 7, further comprising the step of performing one or more rounds of PCR using said stem amplicon sequences and said extended upstream oligonucleotides as templates, wherein said upstream oligonucleotides prime polymerization from said stem amplicon sequences, and wherein said primers prime polymerization from said extended upstream oligonucleotides.

10. The method of claim 9, further comprising a step of detecting the presence or absence of said target nucleic acid in said sample by detecting any accumulated PCR product.

11. The method of claim 7, further comprising incubating said sample with downstream probes and upstream oligonucleotides such that invasive cleavage structures are formed with said stem amplicon sequences, the downstream probes, and the upstream oligonucleotides.

* * * * *